(12) United States Patent
Liang et al.

(10) Patent No.: US 11,079,453 B2
(45) Date of Patent: Aug. 3, 2021

(54) SYSTEM AND METHOD FOR ULTRAFAST MAGNETIC RESONANCE SPECTROSCOPIC IMAGING USING LEARNED SPECTRAL FEATURES

(71) Applicant: THE BOARD OF TRUSTEES OF THE UNIVERSITY OF ILLINOIS, Urbana, IL (US)

(72) Inventors: Zhi-Pei Liang, Champaign, IL (US); Fan Lam, Urbana, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 0 days.

(21) Appl. No.: 16/643,239

(22) PCT Filed: Aug. 23, 2018

(86) PCT No.: PCT/US2018/047774
§ 371 (c)(1),
(2) Date: Feb. 28, 2020

(87) PCT Pub. No.: WO2019/046102
PCT Pub. Date: Mar. 7, 2019

(65) Prior Publication Data
US 2020/0408863 A1 Dec. 31, 2020

Related U.S. Application Data

(60) Provisional application No. 62/552,193, filed on Aug. 30, 2017.

(51) Int. Cl.
*G01R 33/485* (2006.01)
*A61B 5/00* (2006.01)
(Continued)

(52) U.S. Cl.
CPC .......... *G01R 33/485* (2013.01); *A61B 5/0042* (2013.01); *A61B 5/055* (2013.01);
(Continued)

(58) Field of Classification Search
CPC ............ G01R 33/246; G01R 33/34092; G01R 33/4625; G01R 33/465; G01R 33/4816;
(Continued)

(56) References Cited

U.S. PATENT DOCUMENTS

| | | |
|---|---|---|
| 7,592,808 B1 | 9/2009 | King |
| 8,148,979 B1 | 4/2012 | Du |

(Continued)

OTHER PUBLICATIONS

International Preliminary Report on Patentability for PCT/US2018/047774 dated Mar. 3, 2020.
(Continued)

*Primary Examiner* — Gregory H Curran
(74) *Attorney, Agent, or Firm* — Guntin & Gust, PLC; Matthew Tropper

(57) ABSTRACT

A new method is developed for ultrafast, high-resolution magnetic resonance spectroscopic imaging (MRSI) using learned spectral features. The method uses Free Induction Decay (FID) based ultrashort-TE and short-TR acquisition without any solvent suppression pulses to generate the desired spatiospectral encodings. The spectral features for the desired molecules are learned from specifically designed "training" data by taking into account the resonance structure of each compound generated by quantum mechanical simulations. A union-of-subspaces model that incorporates the learned spectral features is used to effectively separate the unsuppressed water/lipid signals, the metabolite signals, and the macromolecule signals. The unsuppressed water spectroscopic signals in the data can be used for various purposes, e.g., removing the need of additional auxiliary scans for calibration, and for generating high quality quan-
(Continued)

titative tissue susceptiability mapping etc. Simultaneous spatiospectral reconstructions of water, lipids, metabolite and macromolecule can be obtained using a single $^1$H-MRSI scan.

20 Claims, 27 Drawing Sheets

(51) Int. Cl.
    *A61B 5/055*     (2006.01)
    *G01R 33/24*     (2006.01)
    *G01R 33/34*     (2006.01)
    *G01R 33/46*     (2006.01)
    *G01R 33/465*     (2006.01)
    *G01R 33/48*     (2006.01)
    *G01R 33/56*     (2006.01)
    *G01R 33/561*     (2006.01)

(52) U.S. Cl.
    CPC ..... *G01R 33/246* (2013.01); *G01R 33/34092* (2013.01); *G01R 33/465* (2013.01); *G01R 33/4625* (2013.01); *G01R 33/4816* (2013.01); *G01R 33/4826* (2013.01); *G01R 33/4828* (2013.01); *G01R 33/5608* (2013.01); *G01R 33/5615* (2013.01)

(58) Field of Classification Search
    CPC ............ G01R 33/4826; G01R 33/4828; G01R 33/485; G01R 33/5608; G01R 33/5615; A61B 5/0042; A61B 5/055
    See application file for complete search history.

(56) References Cited

U.S. PATENT DOCUMENTS

| | | | |
|---|---|---|---|
| 8,965,487 B2 | 2/2015 | Bouma et al. | |
| 10,338,178 B2 | 7/2019 | Liang et al. | |
| 2004/0227512 A1 | 11/2004 | Twieg | |
| 2008/0009703 A1 | 1/2008 | Bito et al. | |
| 2009/0115413 A1 | 5/2009 | Senegas et al. | |
| 2010/0166604 A1 | 7/2010 | Lim et al. | |
| 2012/0274323 A1* | 11/2012 | He | G01R 33/5607 324/309 |
| 2013/0271140 A1 | 10/2013 | Griswold et al. | |
| 2015/0323631 A1 | 11/2015 | Asslaender et al. | |
| 2015/0331077 A1* | 11/2015 | Neji | G01R 33/5607 324/309 |
| 2016/0044439 A1 | 2/2016 | Mittal et al. | |
| 2016/0202336 A1 | 7/2016 | Liang et al. | |
| 2018/0329007 A1* | 11/2018 | Guo | G01R 33/485 |

OTHER PUBLICATIONS

International Search Report & Written Opinion for PCT/US18/047774 dated Dec. 11, 2018.
Adalsteinsson, E. et al., Volumetric Spectroscopic Imaging with Spiral-Based k-space Trajectories. Magn Reson Med; 1998; 39:889-898.
Barkhuijsen, H. et al., Improved Algorithm for Noniterative Time-Domain Model Fitting to Exponentially Damped Magnetic Resonance Signals; Journal of Magnetic Resonance; 1987; 73:553-557.
Brown, Tr et al., NMR chemical shift imaging in three dimensions. Proc. Natl. Acad. Sci. USA, Jun. 1982; 79:3523-3526.
Bydder, M. , Optimal Phased-array Combination for Spectroscopy; Magnetic Resonance Imaging 26 (2008) 847-850.
Chatnuntawech, Itthi et al., Undersampled Spectroscopic Imaging with Model-based Reconstruction; In Proceedings of the International Symposium on Magnetic Resonance in Medicine, Salt Lake City, Utah, USA, 2013. p. 3960.
Clifford, Bryan et al., Motion Correction for 1 H-MRSI of the Brain Using Unsuppressed Water Signals; Apr. 22, 2017; pp. 1-3.
Clifford, Bryan et al., Removal of Nuisance Signals from Limited and Sparse 3D H-MRSI Data of the Brain' May 30, 2015; 1 page.
Clifford, Bryan et al., SENSing-SPICE: Integrating Parallel Imaging with Subspace-Based 30 1H-MRSI; May 7, 2016; pp. 1-3.
Ebel, Andreas et al., Achieving Sufficient Spectral Bandwidth for Volumetric H Echo-Planar Spectroscopic Imaging at 4 Tesla. Magnetic Resonance in Medicine 2005; 54:697-701.
Eslami, Ramin et al., Robust Reconstruction of MRSI Data Using a Sparse Spectral Model and High Resolution MRI Priors; IEEE Transactions on Medical Imaging; 2010;29:1297-1309.
Fu, Maojing et al., High-frame-rate Multislice Speech Imaging with Sparse Samping of (k,t)-space; Proc. Intl. Soc. Mag. Reson. Med. 20 (2012).
Guimaraes, Ar et al., Echoplanar Chemical Shift Imaging. Magnetic Resonance in Medicine 41:877-882 (1999).
Haldar, Justin et al., Rank-Constrained Solutions to Linear Matrix Equations using PowerFactorization; IEEE Signal Processing Letters 2009;16:584-587.
Haldar, Justin et al., Spatiotemporal Imaging with Partially Separable Functions: A Matrix Recovery Approach. In IEEE International Symposium on Biomedical Imaging, Rotterdam, Netherlands, 2010. pp. 716-719.
Haldar, Justin P. et al., Anatomically Constrained Reconstruction from Noisy Data; Magnetic Resonance in Medicine 59:810-818 (2008).
Hu, Xiaoping et al., SLIM: Spectral Localization by Imaging; Magnetic Resonance in Medicine 8, 314-322 (1988).
Jacob, Mathews et al., Improved Model-Based Magnetic Resonance Spectroscopic Imaging; IEEE Transactions on Medical Imaging; 2007;26:1305-1318.
Kasten, J. et al., Data-driven MRSI Spectral Localization Via Low-rank Component Analysis. IEEE Transactions on Medical Imaging; 2013;32:1853-1863.
Kornak, John et al., Bayesian k-Space—Time Reconstruction of MR Spectroscopic Imaging for Enhanced Resolution; IEEE Transactions on Medical Imaging; vol. 29, No. 7, Jul. 2010.
Lam, Fan et al., A Subspace Approach to High-Resolution Spectroscopic Imaging; Feb. 4, 2014; pp. 1-9.
Lam, Fan et al., Achieving High Spatiotemporal Resolution for 1 H-MRSI of the Brain; May 7, 2016; pp. 1-3.
Lam, Fan , Denoising Diffusion-Weighted Magnitude MR Images Using Rank and Edge Constraints; Magnetic Resonance in Medicine 71:1272-1284 (2014).
Lam, Fan et al., High-Resolution H-MRSI of the Brain Using SPICE: Data Acquisition and Image Reconstruction; Oct. 28, 2015; pp. 1-11.
Lam, Fan et al., High-Resolution MR Spectroscopic Imaging; Aug. 26, 2014; 1 page.
Lam, Fan et al., Macromolecule Mapping of the Brain Using Ultrashort-TE Acquisition and Reference-Based Metabolite Removal; Sep. 3, 2017; pp. 1-30.
Lam, Fan et al., Macromolecule Mapping with Ultrashort-TE Acquisition and Metabolite Spectral Prior; Apr. 22, 2017; pp. 1-4.
Lam, Fan et al., Simultaneous Mapping of Brain Metabolites, Macromolecules and Tissue Susceptibility Using SPICE; Apr. 22, 2017; pp. 1-3.
Lam, Fan et al., Ultra-High Resolution 3D H-MRSI of the Brain: Subspace-Based Data Acquisitions and Processing; May 30, 2015; 1 page.
Lam, Fan et al., Ultrahigh-Resolution Metabolic Imaging at 9.4 Tesla; May 7, 2016; pp. 1-3.
Lauterbur, Pc , Zeugmatographic high resolution nuclear magnetic resonance spectroscopy: images of chemical inhomogeneity within macroscopic objects. Journal of the American Chemical Society; Nov. 12, 1975; 97:6866-6868.
Li, Yudu et al., A Subspace Approach to Spectral Quantification; Apr. 22, 2017; pp. 1-3.
Liang, Zhi_Pei , Spatiotemporal Imaging with Partially Separable Functions. In IEEE International Symposium on Biomedical Imaging, Arlington, VA, USA, 2007. pp. 988-991.

(56) References Cited

OTHER PUBLICATIONS

Liang, Zhi-Pei et al., "An Efficient Method for Dynamic Magnetic Resonance Imaging", IEEE Transactions on Medical Imaging, vol. 13, No. 4, Dec. 1994; pp. 1-10.
Liang, Zhi-Pei et al., A Generalized Series Approach to MR Spectroscopic Imaging; IEEE Transactions on Medical Imaging; 1991;10:132-137.
Lin, Fa-Hsuan et al., Sensitivity-Encoded (SENSE) Proton Echo-Planar Spectroscopic Imaging (PEPSI) in the Human Brain; Magnetic Resonance in Medicine 57:249-257 (2007).
Ma, Chao et al., A Subspace-Based Approach to High-Resolution 31 P-MRSI; May 7, 2016; pp. 1-3.
Ma, Chao et al., Accelerated High-Resolution Multidimensional 1 H-MRSI Using Low-Rank Tensors; May 7, 2016; pp. 1-3.
Ma, Chao et al., High-Resolution Dynamic 31 P-MRSI Using High-Order Partially Separable Functions; May 7, 2016; pp. 1-3.
Ma, Chao et al., High-Resolution H-MRSI of the Brain using Short-Echo-Time SPICE; Feb. 2, 2016; pp. 1-31.
Ma, Chao et al., High-Resolution H-MRSI of the Brain Using Short-TE SPICE; Feb. 2, 2016; pp. 1-13.
Ma, Chao et al., High-Resolution H-MRSI of the Brain using Short-TE SPICE; May 30, 2015; 1 page.
Ma, Chao et al., Removal of Nuisance Signals from Limited and Sparse H MRSI Data Using a Union-of-Subspaces Model; Mar. 11, 2015; pp. 1-30.
Ma, Chao et al., Removal of the Nuisance Signals from H MRSI Data of the Brain; Aug. 26, 2014; 1 page.
Mansfield, P., Spatial Mapping of the Chemical Shift in NMR. Magnetic Resonance in Medicine; 1984; 1:370-386.
Maudsley, A.A. et al., Mapping of Brain Metabolite Distributions by Volumetric Proton MR Spectroscopic Imaging (MRSI). Magnetic Resonance in Medicine 61:548-559 (2009).
Maudsley, AA et al., Spatially resolved high resolution spectroscopy by "four-dimensional" NMR. Journal of Magnetic Resonance; 1983; 51:147-152.
Minka, Thomas P., Automatic choice of dimensionality for PCA; Adv Neural Inf Process Syst 2001;13:598-604.
Mulkern, Robert V. et al., Echo Planar Spectroscopic Imaging. Concepts in Magnetic Resonance; 2001;13:213-237.
Nguyen, Hien M. et al., Denoising MR Spectroscopic Imaging Data With Low-Rank Approximations; IEEE Transactions on Biomedical Engineering; 2013;60:78-89.
Ning, Qiang et al., Removal of Nuisance Signal from Sparsely Sampled 1 H-MRSI Data Using Physics-based Spectral Bases; May 7, 2016; pp. 1-3.
Ning, Qiang et al., Spectral Quantification for High-Resolution MR Spectroscopic Imaging with Spatiospectral Constarints; Jul. 27, 2016; pp. 1-9.
Ning, Qiang et al., Spectral Quantification of MRSI Data Using Spatiospectral Constraints; May 7, 2016; pp. 1-3.

Noll, Douglas C. et al., Conjugate Phase MRI Reconstruction With Spatially Variant Sample Density Correction; IEEE Transactions on Medical Imaging; 2005;24:325-336.
Ogg, Robert et al., WET, a T1- and B1-Insensitive Water-Suppression Method for In Vivo Localized H NMR Spectroscopy. Journal of Magnetic Resonance, Series B 1994;104:1-10; abstract only.
Peng, Xi et al., Correction of Field Inhomogeneity Effects on Limited k-Space MRSI Data using Anatomical Constraints; Conf Proc IEEE Eng Med Biol Soc 2010; 2010:883-886.
Peng, Xi et al., Joint Quantitative Susceptibility Mapping and Metabolic Imaging with SPICE; Oct. 24, 2017; pp. 1-25.
Peng, Xi , Quantitative Susceptibility Mapping from Unsuppressed Water Signals in 1H MRSI Data; Apr. 22, 2017; pp. 1-3.
Pohlmann, R. et al., Theoretical evaluation and comparison of fast chemical shift imaging methods. Journal of Magnetic Resonance; 1997;129:145-160.
Posse, S. et al., Proton Echo-Planar Spectroscopic Imaging of J-coupled Resonances in Human Brain at 3 and 4 Tesla. Magnetic Resonance in Medicine; 2007; 58:236-244.
Posse, Stefan et al., High speed H Spectroscopic Imaging in Human Brain by Echo Planar Spatial-Spectral Encoding. Magn Reson Med; 1995; 33:34-40.
Posse, Stefan et al., MR spectroscopic imaging: Principles and Recent Advances. Journal of Magnetic Resonance Imaging; 2013; 37:1301-1325.
Provencher, Stephen W., "Estimation of Metabolite Concentrations from Localized in Vivo Proton NMR Spectra", Quantification of Localized In Vivo H Spectra, MRM 30:672-679, 1993.
Schirda, Cv et al., Rosette Spectroscopic Imaging: Optimal Parameters for Alias-Free, High Sensitivity Spectroscopic Imaging. Journal of Magnetic Resonance Imaging; 29:1375-1385 (2009).
Sheikh, Mohammed A. et al., Rapid, High-Resolution 3D 1 H-MRSI of the Brain based on FID Acquisitions; May 7, 2016; pp. 1-3.
Tsai, Shang-Yueh , Accelerated Proton Echo Planar Spectroscopic Imaging (PEPSI) Using GRAPPA with a 32-Channel Phased-Array Coil; Magnetic Resonance in Medicine 59:989-998 (2008).
Ulfarsson, Magnus O., Dimension Estimation in Noisy PCA With Sure and Random Matrix Theory; IEEE Transactions on Signal Processing; 2008;56:5804-5816.
Zhang, Yi et al., Magnetic resonance Spectroscopy with Linear Algebraic Modeling (SLAM) for higher speed and sensitivity; Journal of Magnetic Resonance; 2012;218:66-76.
Zhao, Bo et al., Highly accelerated parameter mapping with joint partial separability and sparsity constraints. In Proceedings of the International Symposium on Magnetic Resonance in Medicine, Melbourne, Australia, May 5, 2012. p. 2233.
Zhao, Bo et al., Image Reconstruction From Highly Undersampled (k,t) Space Data With Joint Partial Separability and Sparsity Constraints; IEEE Transactions on Medical Imaging; vol. 31, No. 9, Sep. 2012.

* cited by examiner

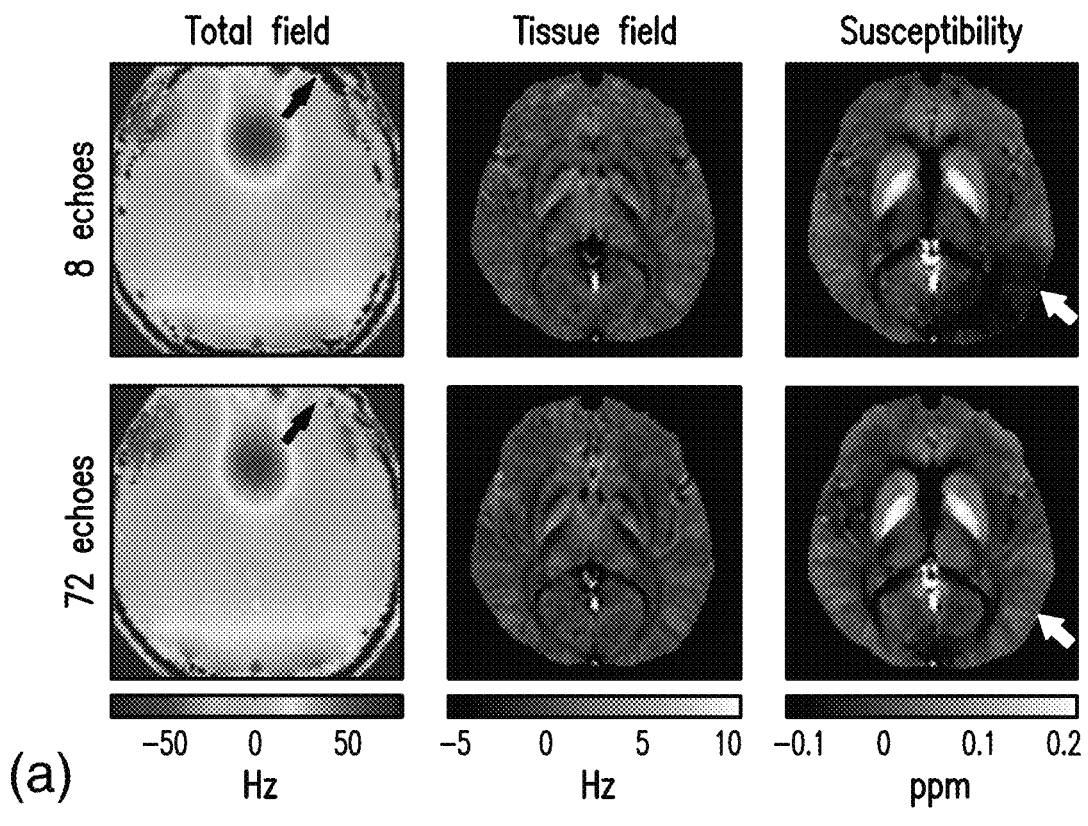
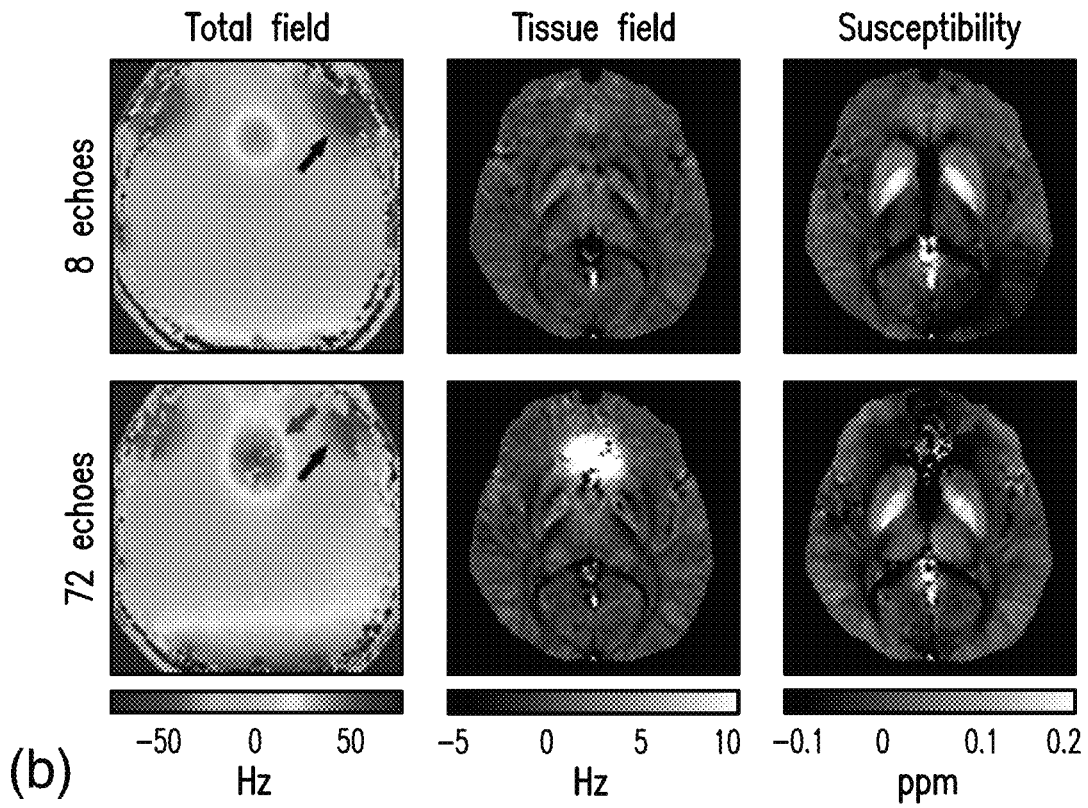
FIG. 10

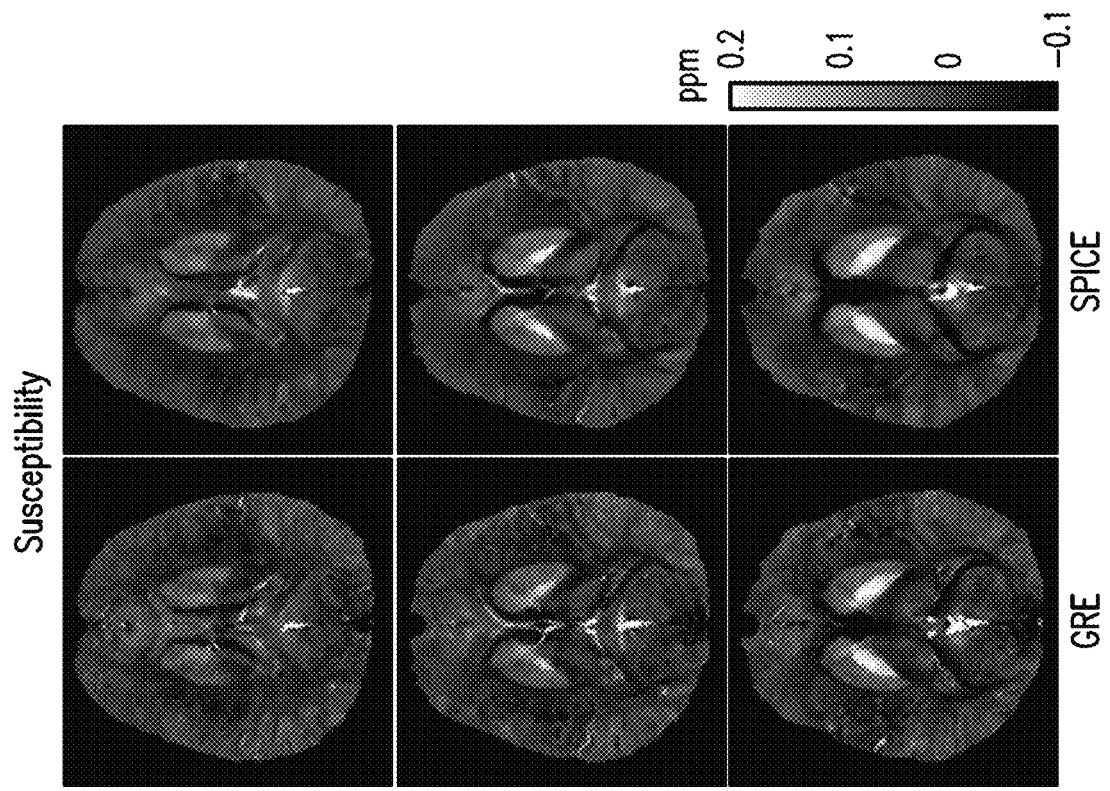
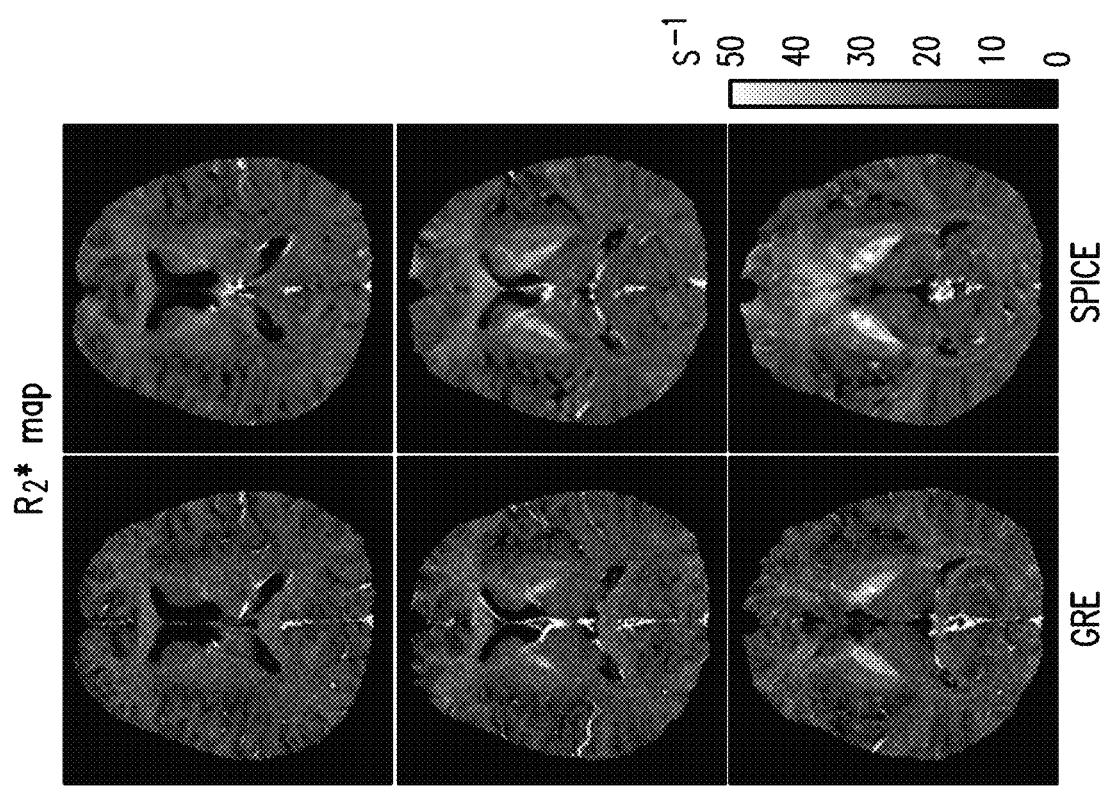
FIG. 12

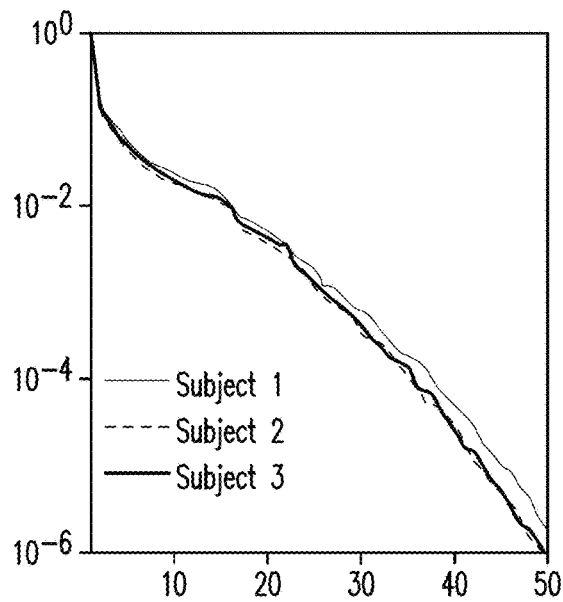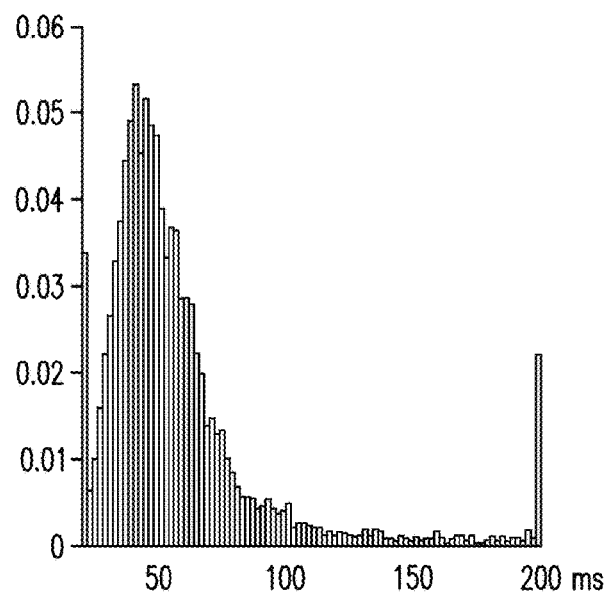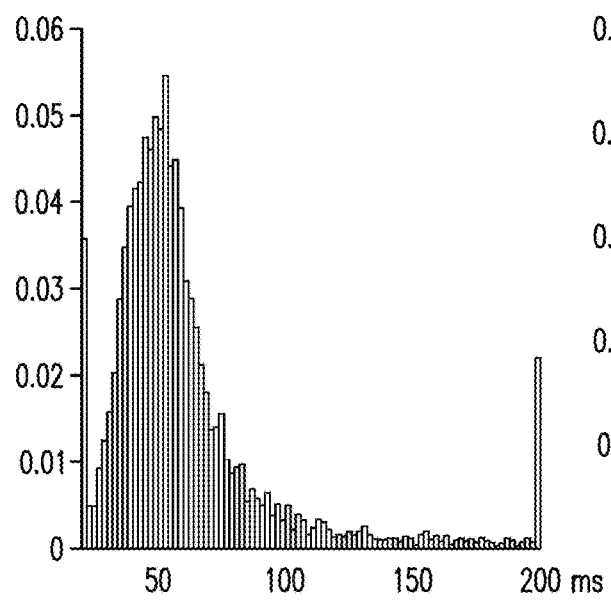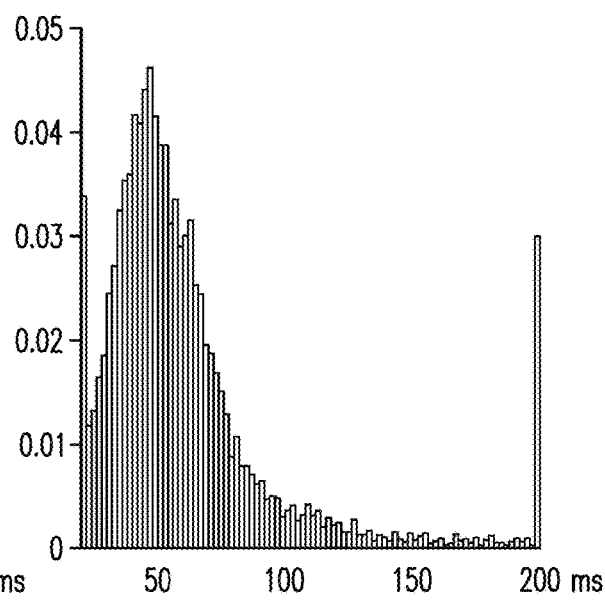
(a)  (b)  (c)  (d)
FIG. 15

Acquiring spatiospectrally encoded FID data covering (k, t)-space in variable density and variable SNR with ultrashort-TE and short-TR, without water and lipid suppression, suitable for image reconstruction using a union-of-subspaces model or a linear combination of low-rank matrix/tensor models  2102

Reconstructing a spatiospectral function from the spatiospectrally encoded FID data that is sparsely sampled using the union-of-subspaces model or the linear combination of low-rank matrix/tensor models  2104

SYSTEM AND METHOD FOR ULTRAFAST MAGNETIC RESONANCE SPECTROSCOPIC IMAGING USING LEARNED SPECTRAL FEATURES

CROSS-REFERENCE TO RELATED APPLICATION(S)

The present application is a U.S. National Stage of International Application No. PCT/US2018/047774, having an International Filing Date of Aug. 23, 2018, which claims the benefit of priority to U.S. Provisional Patent Application No. 62/552,193, filed on Aug. 30, 2017, the disclosure of which is incorporated by reference herein in its entirety (including each appendix, if any, thereof).

International Application No. PCT/US2018/047774 (of which the present application is a U.S. National Stage) is related to U.S. patent application Ser. No. 14/992,498, filed Jan. 11, 2016 (published as U.S. Patent Application Publication No. 2016/0202336), the disclosure of which is incorporated by reference herein in its entirety (including each appendix, if any, thereof).

STATEMENT AS TO FEDERALLY SPONSORED RESEARCH

This invention was made with government support under contract number R21-EB021013 awarded by the National Institutes of Health. The government has certain rights in the invention.

FIELD OF THE DISCLOSURE

The present disclosure generally relates to magnetic resonance spectroscopic imaging.

BACKGROUND

This disclosure relates generally to diagnostic imaging and, more particularly, to an apparatus and method for ultrafast magnetic resonance spectroscopic imaging (MRSI) using learned spectral features of molecules to be imaged and ultra-short TE (Echo Time) and short TR (Repetition Time) acquisition without solvent suppression.

When a substance, such as human tissue, is subject to a uniform magnetic field (such as a polarizing field $B_0$), the individual magnetic moments of the spins in the tissue attempt to align with this polarizing field, but preccess about it in random order at their characteristic Larmor frequency. If the substance, or tissue, is subject to a time-varying magnetic field (excitation field $B_1$) in the x-y plane and which is near the Larmor frequency, the net aligned moment, or "longitudinal magnetization", $M_z$, may be rotated or "tipped" onto the x-y plane to produce a net transverse magnetic moment M. An electrical signal (called MR signal) is produced by the "excited" spins after the excitation field $B_1$ is terminated and the MR signal may be received and processed to form an image.

When the MR signals are used to produce images (or spatial maps of tissue structures) as is done in conventional Magnetic Resonance Imaging (MRI), magnetic field gradients ($G_x$, $G_y$, and $G_z$) are employed for spatial encodings. Typically, the region to be imaged is excited periodically and in each excitation period (or cycle), the spatial encoding gradients vary according to the particular localization method used. The resulting set of encoded signals are received, digitized and processed to reconstruct the image using one of many known reconstruction (or decoding) techniques.

Magnetic resonance spectroscopic imaging (MRSI) is a noninvasive imaging method that provides spectral information in addition to the spatial information that is generated by magnetic resonance imaging (MRI) alone. Traditional MRI generates gray-scale images in which brightness is determined primarily by the water molecule concentrations weighted by water relaxation effects, diffusion effects, etc. The molecular spectral information obtained by MRSI provides additional information about the physiological states of tissues. MRSI can be performed on a standard MRI scanner, and has broad applications in medicine, oncology, and general physiological studies. And, when hydrogen is the target element, MRSI is also called $^1$H-MRSI or proton MRSI. Similarly, there are 31P MRSI and 13C MRSI.

MRSI has been recognized as a powerful tool for noninvasive metabolic studies, but clinical and research applications of this technology have been developing slowly. Reasons for the slow acceptance of the technology for clinical applications include but are not limited to long data acquisition time, poor spatial resolution, and low signal-to-noise ratio (SNR), as examples.

As such, there is a need for improving MRSI to enhance its practical utility and impact.

BRIEF DESCRIPTION OF THE DRAWINGS

Reference will now be made to the accompanying drawings, which are not necessarily drawn to scale, and wherein:

FIG. 2B show a representative FID-based excitation and acquisition scheme developed for FID-SPICE (according to an embodiment) without any solvent suppression. Note the significantly shorter TR, fewer spectral encodings, and ultrashort TE compared to FIG. 2A. FIG. 2C is an illustration of the variable-density sampling pattern along two phase encoding directions (i.e., $k_y$ and k for 3D MRSI), with a fully sampled central k-space and sparsely sampled outer k-space, which achieves extended k-space coverage for high spatial resolution. FIG. 2D shows a further comparison between the (k,t)-space trajectories within each TR for the method according to an embodiment and conventional EPSI acquisitions. The method according to an embodiment has much extended k-space coverage and sparser temporal sampling, both enabled by the subspace model and the methods of various embodiments.

FIG. 10 shows total field inhomogeneity (left), tissue field (middle), and susceptibility maps (right) obtained from SPICE data with 8 and 72 echoes using: portion (a) of FIG. 10—complex exponential fitting without phase unwrapping, and portion (b) of FIG. 10—standard linear fitting with phase unwrapping. The estimated susceptibility maps from more echoes show improved SNR, reduced ringing artifacts and clearer delineation of gray matter and white matter (highlighted by white arrows in rightmost column of portion (a) of FIG. 10), for the complex exponential fitting method. The linear fitting method yielded poor fitting in regions of large field inhomogeneity (highlighted by red arrows in middle and rightmost columns of portion (b) of FIG. 10) when a large number of echoes were used.

FIG. 12 shows $R_2$* and susceptibility maps obtained from the GRE and SPICE data for three representative slices. The results from both data sets clearly delineate iron rich subcortical GM regions including globus pallidus, caudate nucleus, and putamen. The results from the SPICE data have higher SNR (especially for the $R_2$* maps) as a result of a combination of more echoes and lower resolution.

FIG. 15 shows fitting results for training data from three subjects acquired for spectral feature learning. Portion (a) of FIG. 15 shows singular value distributions for the Casorati matrices formed from the three fitted spatiospectral distributions; the rapid decays clearly validate the accuracy of low-dimensional subspace representation of the molecular spectral variations; portions (b-d) of FIG. 15 show the empirical distributions of estimated $T_2^*$ for the three training data sets. Similar distributions can be observed, supporting the concept of using training data to determine a subject-independent distribution. Note that the heightened bar for the $T_2^*$ values greater than 200 ms was due to poorly fitted voxels which were excluded for subspace estimation.

FIG. 21 shows an illustrative method according to an embodiment.

DETAILED DESCRIPTION

Figure 1:
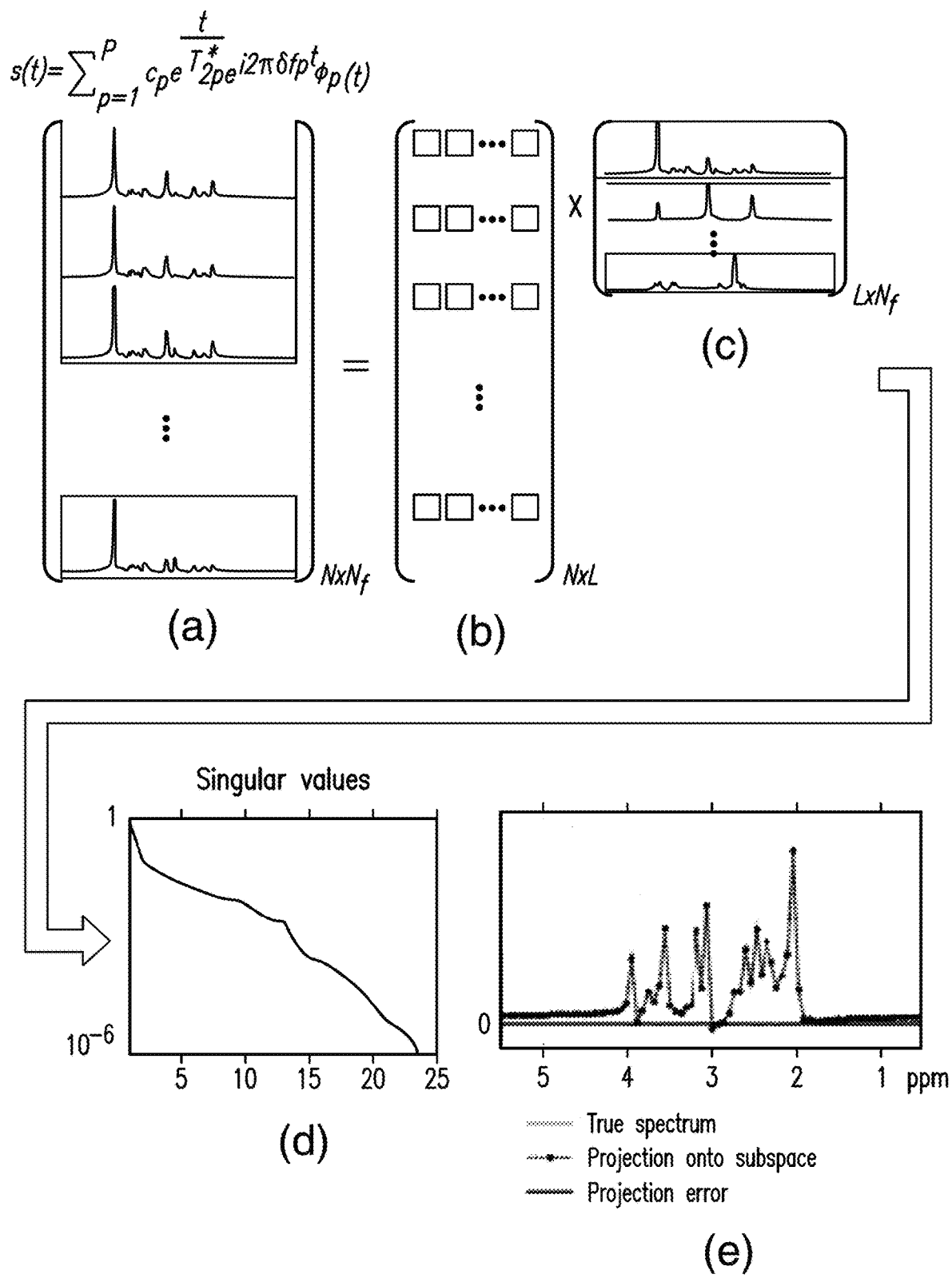
FIG. 1 shows an illustration of a subspace representation for generic spectral variations and the resulting reduction of dimensionality according to an embodiment. A large number of metabolite spectra were synthesized based on the known resonance structures (φ(t) determined using quantum simulation, for example) and the empirical distributions of the spectral shape parameters metabolite (for example $T_2$, δf, determined based on in vivo "training" data). These spectra were arranged into a Casorati matrix [see portion (a) of FIG. 1]. Each of these spectra can be accurately modeled by a linear combination of a small number of basis spectra [see portions (b,c) of FIG. 1], indicating that all the spectra reside in a low-dimensional subspace. This low-dimensional representation implies that the matrix in portion (a) is low-rank, as supported by its rapid singular value decay shown in portion (d) of FIG. 1. A new metabolite spectra (not among those used for basis determination) was generated and projected onto a rank-8 subspace extracted from portion (a). The plots in portion (e) of FIG. 1 compare the original, projected spectra and the corresponding residual. As can be seen, the projection error is negligible compared to the original spectra, further validating the subspace model for representing spectra.

Embodiments are directed toward a method and apparatus to enable ultrafast, high-resolution MRSI.

In one or more embodiments, spectral features of MR-detectable molecules (e.g., N-Acetylaspartate, Creatine, Choline, Glutamate, Glutamine, Myo-inositol, Glutathione, GABA, Lactate, Taurine, Aspartate in $^1$H-MRSI experiments or Phosphocreatine, ATPs, Inorganic phosphate, NADH, Phosphomonoesters, Phosphodiesters in 31P MRSI experiments) are predetermined (or learned) and used to calculate the spatiospectral distributions from measured MRSI data.

In one or more embodiments, spectral features of MR-detectable molecules will be learned from a set of "training" data acquired a priori, taking into account the resonance structure of each compound, which can be predetermined based on MR physics (using quantum simulation, for example) and the data acquisition scheme used.

In one or more embodiments, "training" data for metabolites can be obtained using, single-voxel (SV) scans, CSI scans, and/or EPSI scans with high spectral bandwidth.

In one or more embodiments, "training" data for metabolites can be obtained from different tissue types and tissues of different physiological and pathological conditions. These training data/spectra can then be used to determine a set of spectral basis functions to represent the spectral variations of all the metabolites under all the physiological conditions of interest for a general MRSI experiment.

In one or more embodiments, training data can be acquired for individual molecules or different groups of molecules, i.e., water and lipids, metabolites, neurotransmitters and macromolecules in the brain.

In one or more embodiments, training data for J-coupled metabolites, especially those with relatively low concentrations and/or strongly overlapping peaks, e.g., glutamate, glutamine, glutathione and GABA can be acquired using reference spectra acquired using single-voxel or MRSI methods with multiple TEs and using samples on both sides of the echoes to improve the quantification of these metabolites.

In one or more embodiments, lineshape discrepancy between the individual voxel spectra in the ultrashort-TE, short-TR MRSI data and the reference spectra can be corrected by measuring $B_0$ inhomogeneity and incorporating the lineshape distortion functions derived from this measurement during spectral processing.

In one or more embodiments, a subspace mathematical framework can be used to represent the spectral features of each molecule learning from training data and spin physics.

In one or more embodiments, a union of subspaces model can be used to represent the desired spatiospectral function for a specific experiment, with the spatiospectral distribution of each molecule being represented by a subspace whose spectral basis functions are determined from the learned spectral features.

In one or more embodiments, a technique for simultaneous metabolite and macromolecule mapping (e.g., of the brain) is provided that integrates an FID-based, ultrashort-TE acquisition and predetermined metabolite and macromolecule spectral bases. A time-segmented reconstruction strategy can be used to separate the metabolite spatiospectral distribution and the macromolecule spatiospectral distribution from a single $^1$H-MRSI scan.

In one or more embodiments, an FID-based phase-encoded chemical-shift imaging or echo-planar spectroscopic imaging acquisition can be used to acquire ultrashort-TE (e.g., <4 ms) MRSI data that simultaneously capture spectroscopic signals of water, metabolites and macromolecules with high signal-to-noise-ratio (SNR) efficiency.

In one or more embodiments, a very-short-TR (e.g., <300 ms) acquisition without solvent suppression pulses can be used.

In one or more embodiments, the data space, i.e., the (k,t)-space, is sparsely sampled and covered in variable densities. In particular, a central k-space is covered with Nyquist density and the outer k-space is below the Nyquist density. The temporal dimension (t) is undersampled, i.e., the time interval between different echoes is larger than what is required by the spectral Nyquist criterion. Ramp sampling can also be applied along the frequency encoding direction (e.g., $k_x$ direction).

In one or more embodiments, a method is provided that can track head motion and correct for its effects on MRSI techniques, such as $^1$H-MRSI data acquired without water suppression. Specifically, interleaved motion navigators can be collected in circular and linear trajectories. A specialized data processing scheme can be employed for processing the navigator data along with the unsuppressed spectroscopic water signals to determine the motion parameters. The estimated parameters can be used to correct the effects of motion in the data. In one or more embodiments, the data acquisition scheme can include insertion of two sets of navigators (a) three perpendicular orbital navigators, and (b) three perpendicular linear navigators into a $^1$H-MRSI acquisition.

In one or more embodiments, a technique for joint metabolite and tissue susceptibility mapping (e.g., of the brain) is provided, such as through using a single $^1$H-MRSI acquisition without water suppression. In one or more embodiments, SPectroscopic Imaging by exploiting spatio-spectral CorrElation (SPICE) can be utilized in order to provide ultrashort-TE, short-TR (e.g., $^1$H-MRSI) without water suppression. This acquisition can simultaneously encode both the chemical shift information from the metabolites and the tissue susceptibility induced phase variations in the spectroscopic signals. A variable density sparse sampling scheme and/or ramp sampling can be used to cover a further extended k-space to achieve the spatial resolution desired by Quantitative susceptibility mapping (QSM), while maintaining a sufficient number of spatiospectral encodings for metabolite reconstruction. For data processing, high quality QSM can be produced from the unsuppressed water signals due to the larger number of echoes and anatomical prior. Metabolite spatiospectral distributions can be obtained using a union-of-subspaces model described by the SPICE reconstruction method.

In one or more embodiments, parallel imaging reconstruction can be employed. For example, auto calibration data in the central k-space of early echoes can be used for an initial GRAPPA reconstruction (i.e., a "sliding window" scheme employed to take advantage of neighboring echoes for improved kernel calculation). The GRAPPA reconstructions at these echoes can then be used to derive high-SNR sensitivity maps, with which a constrained reconstruction can be performed by integrating SENSE, sparsity and a rank constraint.

In one or more embodiments, total field inhomogeneity can be estimated from the reconstructed water images using a complex exponential fitting procedure using all the echoes. The background field from external susceptibility sources out of the ROI can be removed and tissue susceptibility can be reconstructed from the remaining tissue field using morphology enabled dipole inversion. A high-resolution anatomical reference image (e.g., a $T_1$-weighted or a $T_2^*$-weighted scan) can be used to derive the morphological information.

In one or more embodiments, SPICE reconstruction can be used to obtain metabolite spatiospectral distributions from the same data, by integrating a union-of-subspaces model, field inhomogeneity correction, and spatial regularization functionals. The union-of-subspaces model can include predetermined subspaces for water, lipids, metabolites and macromolecules. Water and fat signals can also be removed during the reconstruction.

Reference will now be made to ultrafast MRSI according to various embodiments. As described herein, the capability of MRSI in simultaneously mapping different molecules in the human body noninvasively promises to enormously enhance the ability to detect and characterize disease, to monitor the efficacy of therapy, and to increase understanding of the body's basic physiology. However, even after four decades of development, the existing MRSI methods are still far behind in providing the signal-to-noise ratio (SNR), resolution and speed desired for practical applications. As described herein is a new imaging technology that enables MRSI of the brain with a nominal isotropic 3 mm resolution in 5-7 minutes. This unprecedented capability is achieved by a set of unconventional signal encoding and decoding strategies developed within a subspace imaging framework. Moreover, the subspace model allows for effective separation of different signal components encoded in the spectroscopic data with large dynamic range differences, enabling the capability of joint tissue susceptibility, metabolite and macromolecule mapping using a single scan.

MRI has revolutionized medicine and biology by providing clinicians and scientists the ability to visualize detailed anatomical organizations of the human body noninvasively. To enable better understanding and characterization of the underlying molecular basis of various physiological functions and disease processes, the ability to obtain molecule-specific information is strongly desired (1A, 2A) [references 1A-79A below are referred to herein by a number followed by the letter "A", e.g., 1A, 2A, etc.]. MRSI addresses this need by producing spatially-resolved spectra differentiating MR signals from different molecules, without the requirement of injecting exogenous contrast agents or radioactive tracers (3A-6A). For example, proton ($^1$H) MRSI, allows the detection and quantification of about 15 physiologically important molecules (including neurotransmitters such as GABA and glutamate, and metabolites such as NAA, creatine and choline), providing the capability to study a range of basic science questions related to in vivo metabolism 7A, neurotransmission 8A, and brain energetics 9A, and to address many clinical problems such as diagnosis and characterization of neurodegenerative diseases 10A, cancers 11A, 12A, and assessment of therapeutic efficacy 13A, 14A.

The unique power of MRSI as a label-free molecular imaging modality has long been recognized 4A, 15A, but its research and clinical applications have been developing slowly due to a number of fundamental technical hurdles. Specifically, MRSI adds one or more spectral dimensions to the image function of interest, making the imaging problem higher dimensional. Accordingly, the number of spatiospectral encodings required in the conventional Nyquist sampling paradigm grows exponentially as the resolution increases, which leads to the slow imaging speed. In the meantime, the molecules of interest for MRSI have very low concentrations (three to four orders of magnitude lower than water), which leads to the inherently low signal-to-noise ratio (SNR). Many techniques have been developed to address these challenges, including fast scanning strategies that accelerate data acquisition by using oscillating gradients to simultaneously encode both the spatial and spectral dimensions after each excitation 16A-22A, sophisticated signal processing methods that aim to improve SNR or resolution of the spatiospectral reconstruction by making use of various kinds of prior information 23A-28A, and advanced instrumentations (such as phased-array coils and ultrahighfield systems) that try to offer better tradeoffs among speed, resolution and SNR 29A-36A. However, even with all these efforts, state-of-the-art MRSI methods are still limited to a centimeter-level resolution, around half an hour imaging time, and very limited organ coverage 37A. Furthermore, for $^1$H-MRSI in particular, effective separating the three to four orders of magnitude stronger water and lipid signals from the metabolite signals of interest is also a long-standing challenge. A common practice to address this is to incorporate special water and lipid signal suppression modules into the MRSI pulse sequences 38A-40A, which strongly limit the acquisition design yet complete suppression is impossible. Additional processing is still required to remove the residual water/lipid signals 41A, 42A.

Presented herein is a new imaging technology that enabled millimeter-level resolution MRSI of the brain (e.g., isotropic 3 mm voxel size) with almost whole organ coverage and without any solvent suppression in just several minutes (e.g., five to seven minutes), which is more than an order of magnitude improvement over state-of-the-art MRSI methods in terms of the combination of speed, resolution and SNR. This unprecedented technology was built on the SPICE (SPectroscopic Imaging by exploiting spatiospectral CorrElation) subspace imaging approach. SPICE exploits the property that each spatially-resolved spectrum in the high-dimensional spatiospectral function of interest can be accurately represented as a linear combination of a small number of basis functions 43A-45A. This representation transforms the imaging problem into recovering a significantly smaller set of coefficients instead of treating all the spectral points and spatial voxels as independent unknowns, reducing the dimensionality of the imaging problem and making better tradeoffs among speed, resolution and SNR possible. Based on this subspace framework, an ultrafast MRSI technology was developed that entails a set of unconventional acquisition and processing strategies. Specifically, integrated are an ultrashort-TE, short-TR excitation scheme without solvent suppression and a rapid, sparse spatiospectral encoding strategy that can generate ultrahigh-resolution MRSI data in a short period with high SNR efficiency. By recognizing that the molecular-dependent spectral variations can be learned from training data to predetermine the signal subspaces, a union-of-subspaces (UoSS) model-based approach was developed to effectively separate different signal components, i.e., water/lipids, metabolites and macromolecules, and to produce high-SNR spatiospectral reconstructions from the rapidly acquired noisy data. By removing solvent suppression, advantages are also taken of the companion water signals to extract valuable information for data processing (e.g., $B_0$ inhomogeneity maps, frequency drifts and coil sensitivity maps), eliminating the need of acquiring extra auxiliary scans, and to develop a brand-new capability for simultaneous mapping of tissue susceptibility, metabolites and macromolecules in the brain, using a single $^1$H-MRSI scan. This exciting information-rich imaging capability can have many potential applications in various neuroscience and clinical studies.

An embodiment of the subspace imaging framework described herein is built on the assumption that the signal evolution at each voxel, although complex, is fundamentally governed by a well-defined physical process and a few parameters. The low-dimensional subspace model can be viewed as a different mathematical representation for the ensemble of these signal evolutions. Therefore, the imaging framework of various embodiments also extends beyond the context of MRSI to other high-dimensional imaging problems where signal evolutions can be well-characterized by spin physics and a particular physiological process, and where these evolutions yield low-dimensional representations that can be predetermined from specially designed training data, thus presenting new opportunities to incorporate learning into the imaging process.

Reference will now be made to certain Results (SPICE: Subspace Imaging for MRSI). In the standard MRSI encoding and decoding paradigm, the high-dimensional spatiospectral function of interest is typically modeled as (assuming spatially support limited and spectrally bandlimited (17A))

$$\rho(r, f) = \sum_{n=1}^{N_r} \sum_{m=1}^{N_f} c_{nm} e^{i2\pi n \Delta k r} e^{i2\pi m \Delta t f}, \quad \text{[Equation 1A]}$$

where $\Delta k$ and $\Delta t$ are determined by the Nyquist criterion for the spatial and spectral dimensions (i.e., by the spatial field-of-view and spectral bandwidth, respectively) (48A). Fourier encodings are acquired in a corresponding (k,t)-space and $\rho(r, f)$ is reconstructed using a Fourier transform. Constrained by the Nyquist sampling theorem, as the required spatiospectral resolution increases, the number of encodings required grows exponentially ($N_r \times N_f$). Furthermore, each of these encodings is required to have high SNR due to the low molecular concentrations of the metabolites of interest embedded in $\rho(r, f)$, thus the very slow imaging speed and low resolution (large voxel size) commonly observed in MRSI experiments. Compressed sensing (CS), a new signal encoding and decoding paradigm, uses different sets of bases to represent the functions of interest and exploit the sparsity of the coefficients to enable image reconstruction from sub-Nyquist samples (49A-52A). Several CS-based methods were successfully applied to a number of MR imaging problems (53A-55A). However, due to the requirement of high-SNR data (56A, 57A), the applications of CS to MRSI have been limited, e.g., to accelerate hyperpolarized (13A) C-MRSI (58A) or very low-resolution acquisitions (59A-61A).

An embodiment of SPICE is a subspace imaging approach to accelerate MRSI, by using the following low-dimensional subspace model to represent the high-dimensional spatiospectral function $\rho(r, f)$ 45A, 62A, 63A $$\rho(r, f) = \sum_{l=1}^{L} c_l(r)\phi_l(f), \quad \text{[Equation 2A]}$$

where $\{\phi_l(f)\}_{l=1}^{L}$ is a set of basis functions capturing the spectral variations of different molecules and $\{c_l(r)\}_{l=1}^{L}$ are the corresponding coefficients, with $L \ll N_f$. This subspace model is a mathematical consequence of the fact that each voxel spectrum can be viewed as a combination of signals originating from a limited number of molecules, each of which has a well-defined spectral structure determined by spin physics and a set of experiment-dependent parameters (e.g., exponential decaying parameters $\{T_2^*\}$ and chemical shift variations $\delta f$. Accordingly, it leads to a low-rank model of $\rho(r, f)$ if a voxel representation is used (i.e., specify $\rho(r, f)$ by determining its values over a point set $\{r_n, f_m\}_{n,m=1}^{N_r,N_f}$) (43A), implying a significantly reduced number of degrees of-freedom, making fast MRSI using sub-Nyquist sampling possible (45A). FIG. 1 illustrates this low-rank representation and resulting reduction of degrees of freedom. Specifically, representative metabolite spectra were synthesized based on the known resonance structures (determined using quantum simulation) and the empirical distributions of the spectral shape parameters metabolite (determined based on in vivo "training" data). It has been shown that the Casorati matrix with each row being a specific spectrum (portion (a) of FIG. 1) has a very low rank (rapidly decaying singular values in portion (d) of FIG. 1), indicating that each row can be accurately approximated by a linear combination pf a small number of basis (portion (c) of FIG. 1). Using acquisition and reconstruction methods developed within this framework, millimeter-resolution, volumetric MRSI can be achieved.

Figure 2A:
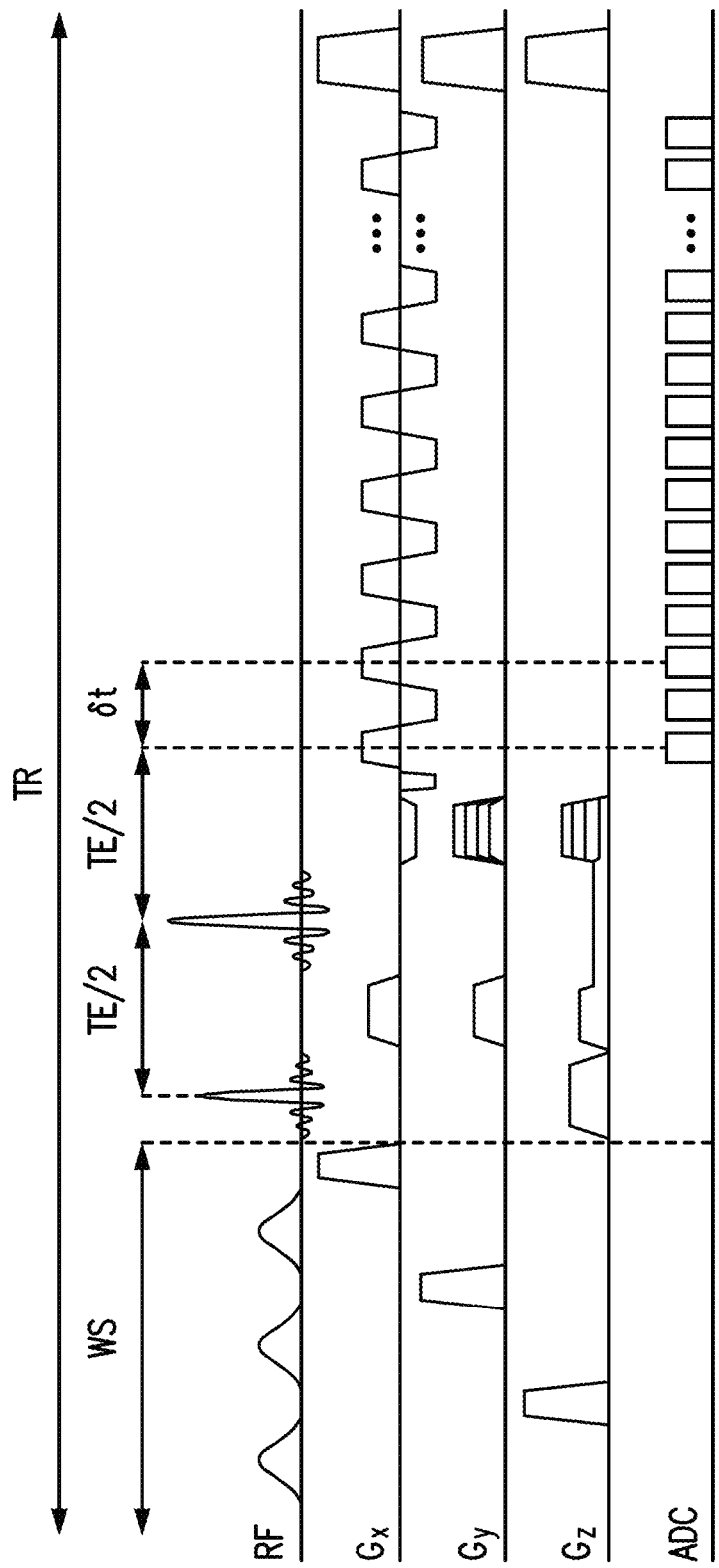
FIGS. 2A-2D relate to a FID-SPICE acquisition strategy according to an embodiment. A spin-echo-based EPSI sequence (a state-of-the-art acquisition technique) with solvent suppression is shown in FIG. 2A to highlight the key differences in the method of an embodiment.
Figure 2B:
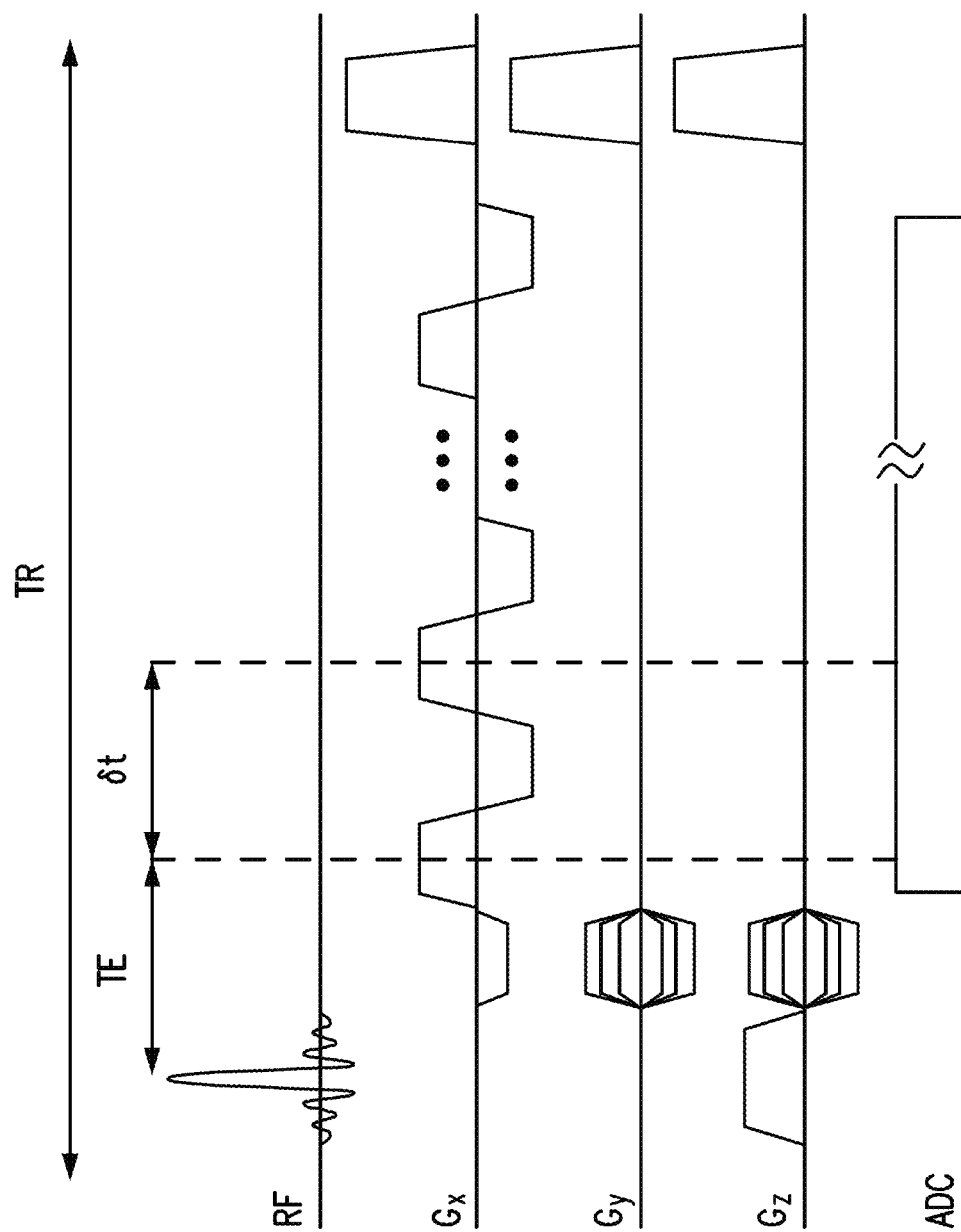
Figure 2C:
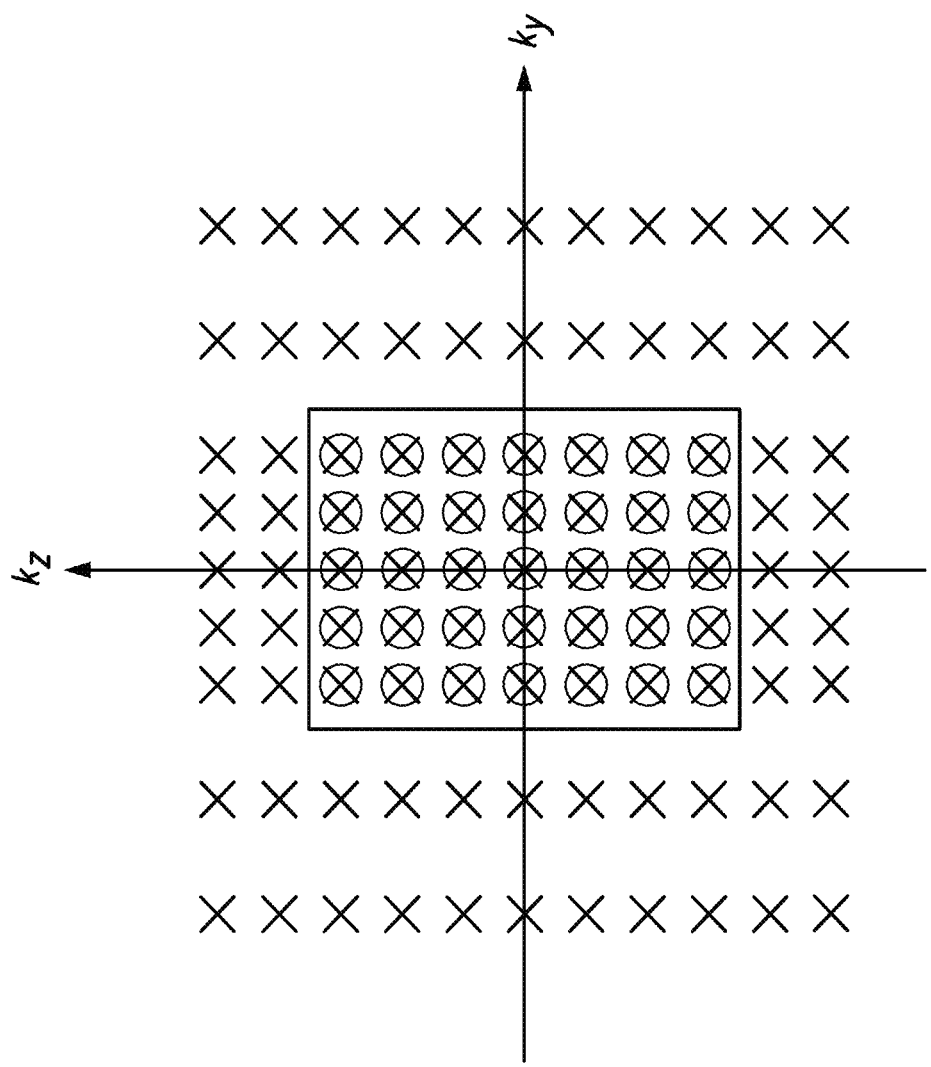
Figure 2D:
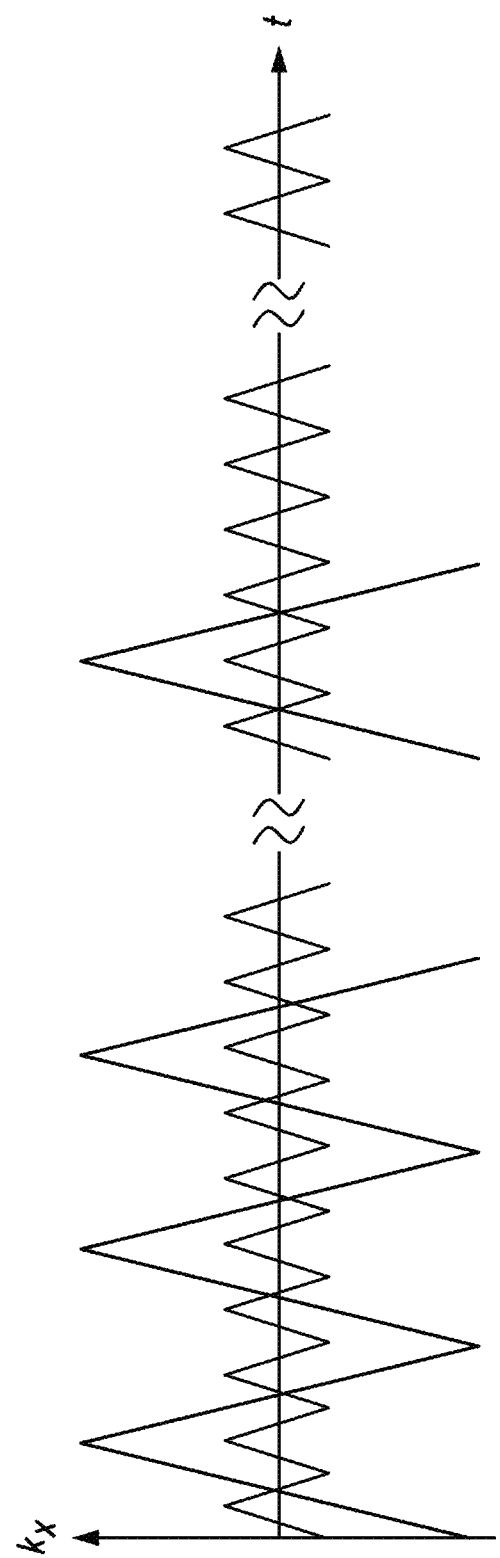

Reference will now be made to certain Results (FID-SPICE: Ultrafast $^1$H-MRSI). One approach to further accelerate the data acquisition is k-space undersampling by using either parallel imaging or CS-based sparse sampling. However, such undersampling alone is still limited to the inherent SNR efficiency of SE-based acquisition and does not fully take advantage of the power of the subspace model in reducing spectral sampling (i.e., still requiring longer TRs to maintain SNR efficiency (65A)). Moreover, the level of undersampling is constrained by the very low SNR of the MRSI data. As described herein is a rapid encoding strategy that differs from the existing MRSI acquisition methods with five integrative features: 1) an FID pulse-acquire excitation scheme that allows achievement of ultrashort-TE for improved SNR; 2) small numbers of spectral encodings required for each k-space location (e.g., approximately 60-100) that enabled very short TRs with optimized SNR efficiency and traded spectral encoding for spatial encoding (taking advantage of the fact that key spectral features have been specified by the spectral basis $\phi_l(f)$; 3) a special gradient waveform for rapid spatiospectral encoding after each excitation that can produce (k,t)-space trajectories with extended k-space coverage and sub-Nyquist spectral sampling; 4) a variable density k-space sparse sampling strategy that extends the coverage along the phase encoding directions (e.g., $k_y$ and $k_z$) for high resolution while keeping a center k-space region fully sampled to maintain a sufficient SNR for metabolite and MM reconstructions; and 5) no solvent suppression modules, which not only further shortened the TR but also allowed maximization of the utility of the unsuppressed water signals by designing special data processing strategies. The integration of these features leads to an ultrashort-TE, very-short-TR, rapid acquisition scheme that can produce ultrahigh-resolution MRSI data in several minutes, e.g., a nominal voxel size of 2:5×2:5×3 mm$^3$ in about 5 minutes. The complete acquisition scheme is illustrated in FIGS. 2B-D with a comparison (see FIG. 2A) to a standard EPSI sequence (a standard fast-scanning method to accelerate MRSI) (17A, 19A), which is required to satisfy both spatial and spectral Nyquist sampling criteria. Note that the differential emphasis on the spatial and spectral encoding for the acquisition according to this embodiment.

Such a special acquisition strategy imposes unique challenges for spatiospectral processing. In particular, the effective usage of the unsuppressed water signals, the separation of different signal components with a large dynamic range differences (e.g., the strong water and lipid signals versus metabolite signal of interest), and the reconstruction of metabolite spatiospectral distributions from the rapidly acquired noisy data. To address these challenges, the subspace model in Eq. (2A) has been extended to a union-of-subspaces (UoSS) model, i.e., $$\rho(r,f) = \sum_{l_m=1}^{L_m} c_{l_m}(r)\phi_{l_m}(f) + \sum_{l_w=1}^{L_w} c_{l_w}(r)\phi_{l_w}(f) + \sum_{l_f=1}^{L_f} c_{l_f}(r)\phi_{l_f}(f) + \sum_{l_{MM}=1}^{L_{MM}} c_{l_{MM}}(r)\phi_{l_{MM}}(f),$$ [Equation 3A]

where $\{\phi_{l_m}(f)\}_{l_m=1}^{L_m}$, $\{\phi_{l_w}(f)\}_{l_w=1}^{L_w}$, $\{\phi_{l_f}(f)\}_{l_f=1}^{L_f}$ and $\{\phi_{l_{MM}}(f)\}_{l_{MM}=1}^{L_{MM}}$ are bases spanning the low dimensional subspaces where the signals of individual molecular groups reside, i.e., metabolites, water, lipids and macromolecules. With such a model, the key issues are the determination of the subspaces (i.e., $\{\phi_{l_x}(f)\}_{l_x=1}^{L_x}$) and the use of these subspace for effective separation of different signal components and high-SNR metabolite reconstruction from noisy data. Recognizing that a general metabolite spectrum can be decomposed into key components such as resonance structures which can be predicted by quantum simulations, molecule-dependent spectral variations which can be captured by a few spectral parameters, and experiment-dependent lineshape distortions, a machine learning based strategy can be used to pre-estimate the metabolite signal subspace from training data and can be used for general MRSI experiment. With the learned subspace, spatiospectral reconstruction can be formulated as a regularized least-squares estimation of the spatial coefficients $\{c_{l_x}(r)\}$ under Gaussian noise assumption (see the discussion herein of Methods). In the following sections, an embodiment of an ultrafast MRSI technology using above described integrative subspace-based acquisition and processing strategies will sometimes be referred to as FID-SPICE.

Figure 3:
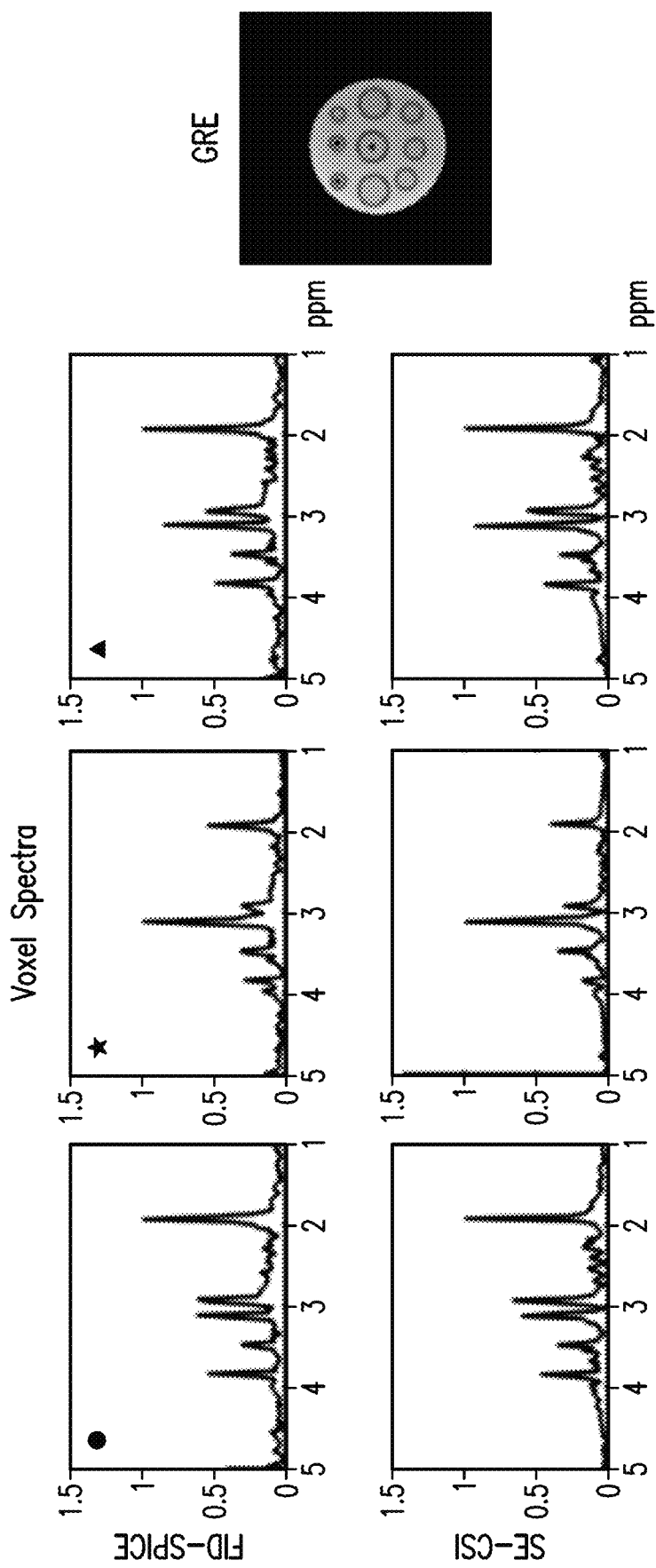
FIG. 3 relates to experimental results from a phantom with brain metabolite solutions at physiological concentrations, produced by a 22 min standard spin-echo CSI acquisition (SE-CSI) and a 1 min FID-SPICE acquisition according to an embodiment. The reconstructed spectral distributions from three different 6.6×6.6×10 $mm^3$ voxels are shown in the first three columns. The results for the SE-CSI were obtained by Fourier transform reconstruction followed by $B_0$ inhomogeneity correction. The voxel locations were indicated by the different shapes shown in the structural image on the most right, which was obtained by a standard gradient echo scan (GRE). The 1 min FID-SPICE acquisition produced similar results as the 22 min long SE-CSI scan.

With reference now to certain Phantom Studies, an embodiment of FID-SPICE has been implemented on clinical 3T MRI systems. Studies on a physical phantom that contains vials of various sizes (to demonstrate resolution capability) filled with brain metabolite solutions at physiological concentrations were carried out. FIG. 3 shows a set of single-slice 2D MRSI results obtained on a Siemens Prisma 3T scanner (Siemens, Erlangen, Germany). Spatial distributions of the Choline molecule (Cho) and localized spectra corresponding to 6.6×6.6×10 mm$^3$ voxels produced by a standard 22 min SE-CSI acquisition (with 1.5 s TR) and a 1 min FID-SPICE acquisition (with 0.25 s TR) are compared. High-SNR Cho map and high-resolution metabolite spectra were reconstructed from the CSI data, as expected, but FID-SPICE produced very similar results using only 1/22th of the scanning time, demonstrating its impressive capability in achieving rapid MRSI.

Figure 4:
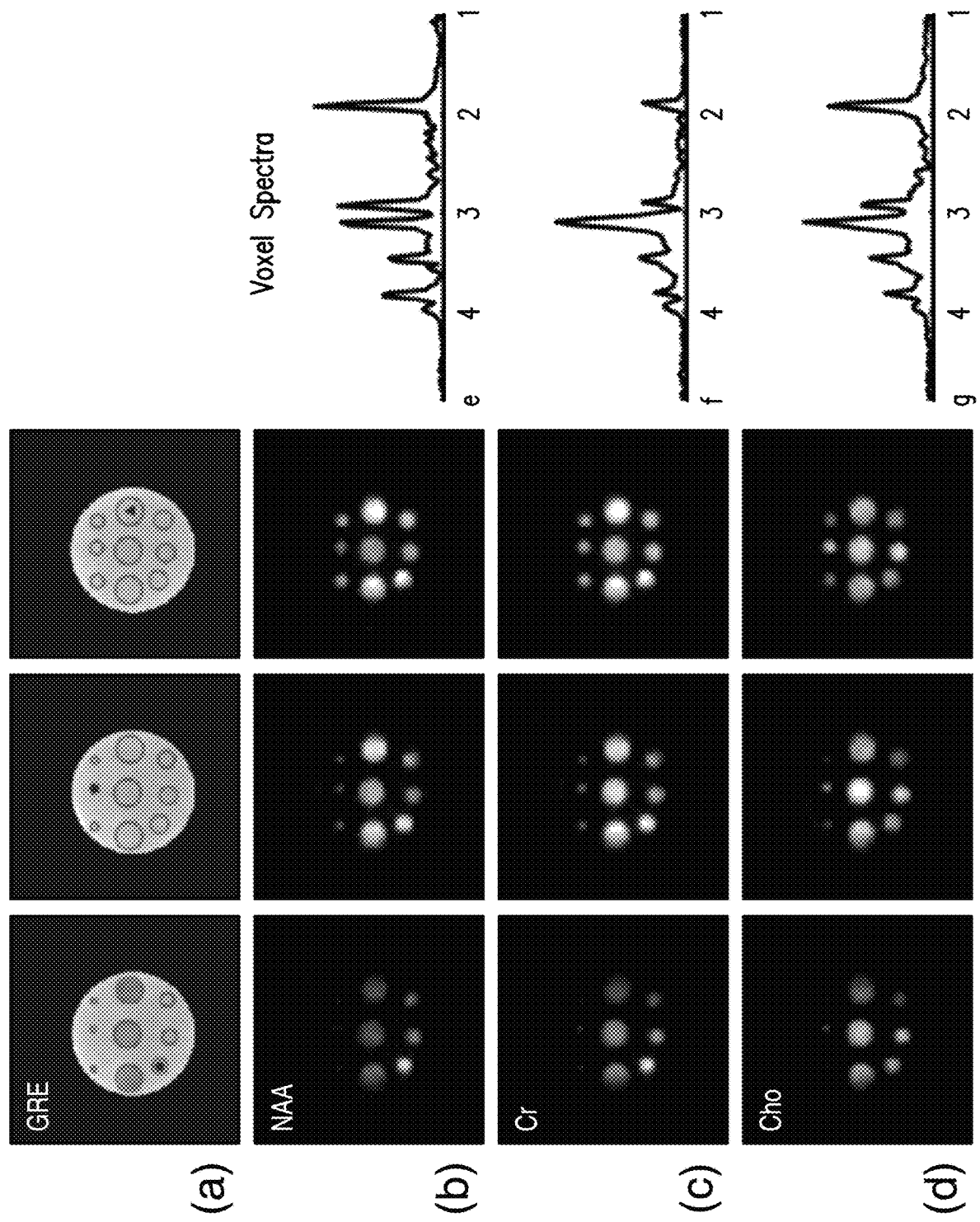
FIG. 4 shows fast, high-resolution 3D $^4$H-MRSI results from the phantom in FIG. 3. Portion (a) of FIG. 4 shows $T_1$-weighted water images illustrating the structural arrangement of the phantom (notice the changing size of the top and bottom row vials; the length of the center vials is shorter thus the changed intensity in the top slice); portions (b-d) of FIG. 4 show metabolite maps, i.e., NAA, Cr and Cho for the corresponding slices in portion (a) produced by a 7 min FID-SPICE acquisition; and portions (e-g) of FIG. 4 show representative spectra from different 3×3×3 mm voxels, whose locations were indicated by the different shapes in portion (a). As can be seen, the FID-SPICE method of an embodiment produced high-resolution, high-SNR spatiospectral distributions, allowing visualization of even the smallest vials.

High-resolution 3D MRSI reconstruction were also produced from the phantom. A set of representative results obtained from a 7 min acquisition with TR/TE=280/3.3 ms are shown in FIG. 4. The 3D structural arrangement of the phantom is shown in portion (a) of FIG. 4, NAA maps with a nominal voxel size of 3×3×3 mm$^3$ for the corresponding slices in portion (b) of FIG. 4, Cr and Cho maps are shown in portions (c) and (d) of FIG. 4, respectively. Even the smallest vials can be visualized in the reconstructed metabolite maps, and the variations along the third spatial dimension can be resolved as well. In addition, high-SNR spatially localized spectra from 3×3-voxel ROIs are shown in portions (e)-(g) of FIG. 4, demonstrating the combination of speed, resolution and SNR achieved by the method of this embodiment.

Figure 5:
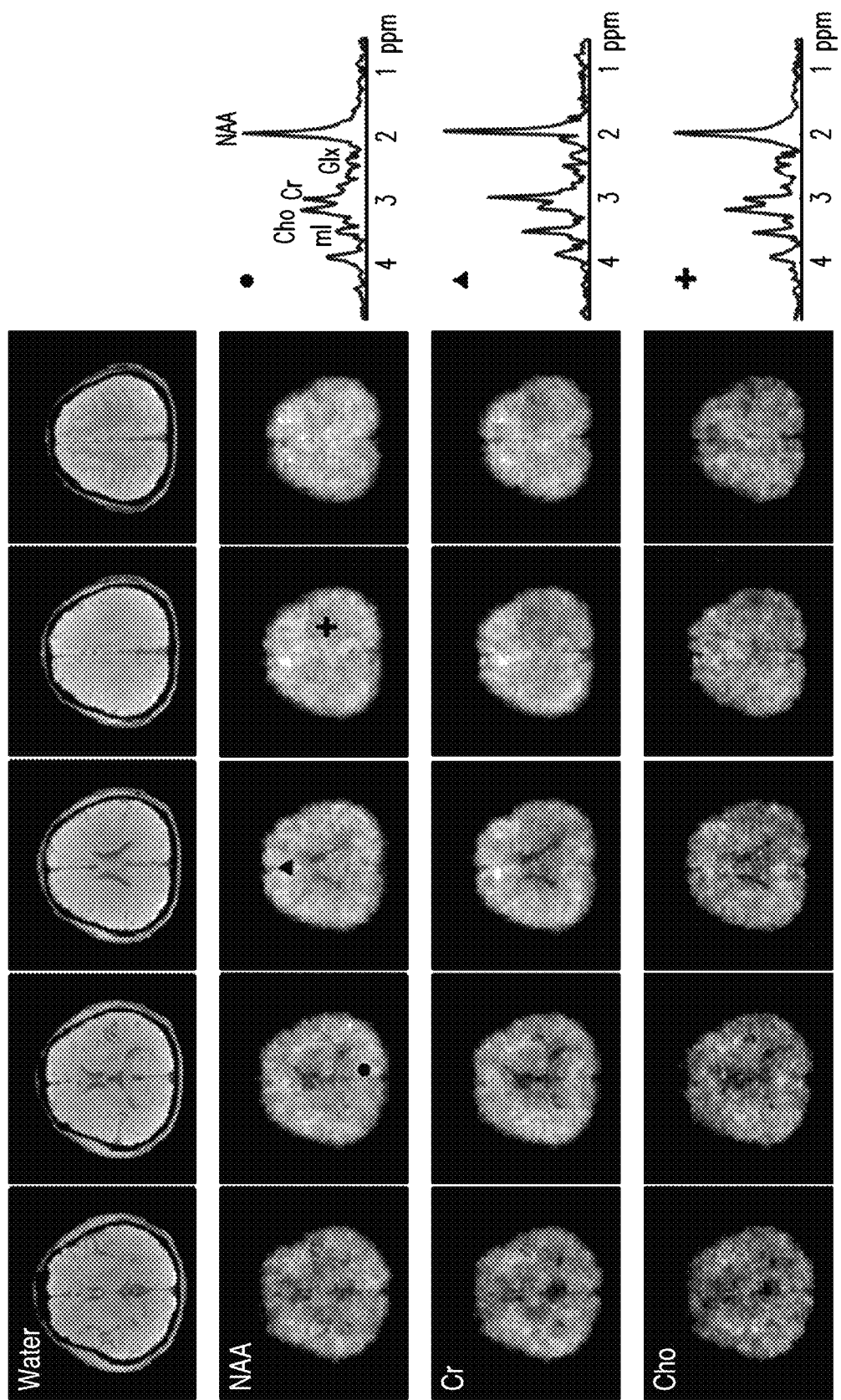
FIG. 5 shows ultrafast $^1$H-MRSI without water suppression from a human brain according to an embodiment. The first row on the left panel shows the water images (the 5th echo in the MRSI data) at different 3D slices. The second to fourth rows show the maps of NAA, Cr and Cho for the corresponding slices. The right panel shows three representative localized spectra (from 2.5×2.5×3 $mm^3$ voxels). The voxel locations are marked by the symbols in the water images and the left corners of the spectrum plots.

Reference will now be made to certain In Vivo Brain Studies. Rapid $^1$H-MRSI with almost whole brain coverage can be achieved using the acquisition and processing strategies of an embodiment (see FIG. 5). High-resolution brain metabolite maps with a nominal spatial resolution of 3×3×3 mm$^3$ (or 0.027 cc) were obtained from a healthy volunteer (FIG. 5, left panel), along with high-SNR spatially resolved spectra (FIG. 5, right panel), using a 5 min scan with TR/TE=210/3 ms. The spatial variations of the NAA molecules across different slices in the brain exhibit features matching very well with anatomical structures (observed in the water images shown in the first row of FIG. 5). The gray matter shows higher level of NAA and Cr, and the ventricles and cortical sulci (with negligible metabolite levels) are clearly delineated. The spatially localized spectra from voxels in different brain structures also show very good SNR with well resolved metabolite peaks. Meanwhile, negligible water/lipid residuals and clear separation from the macromolecule baseline can be observed.

Figure 6:
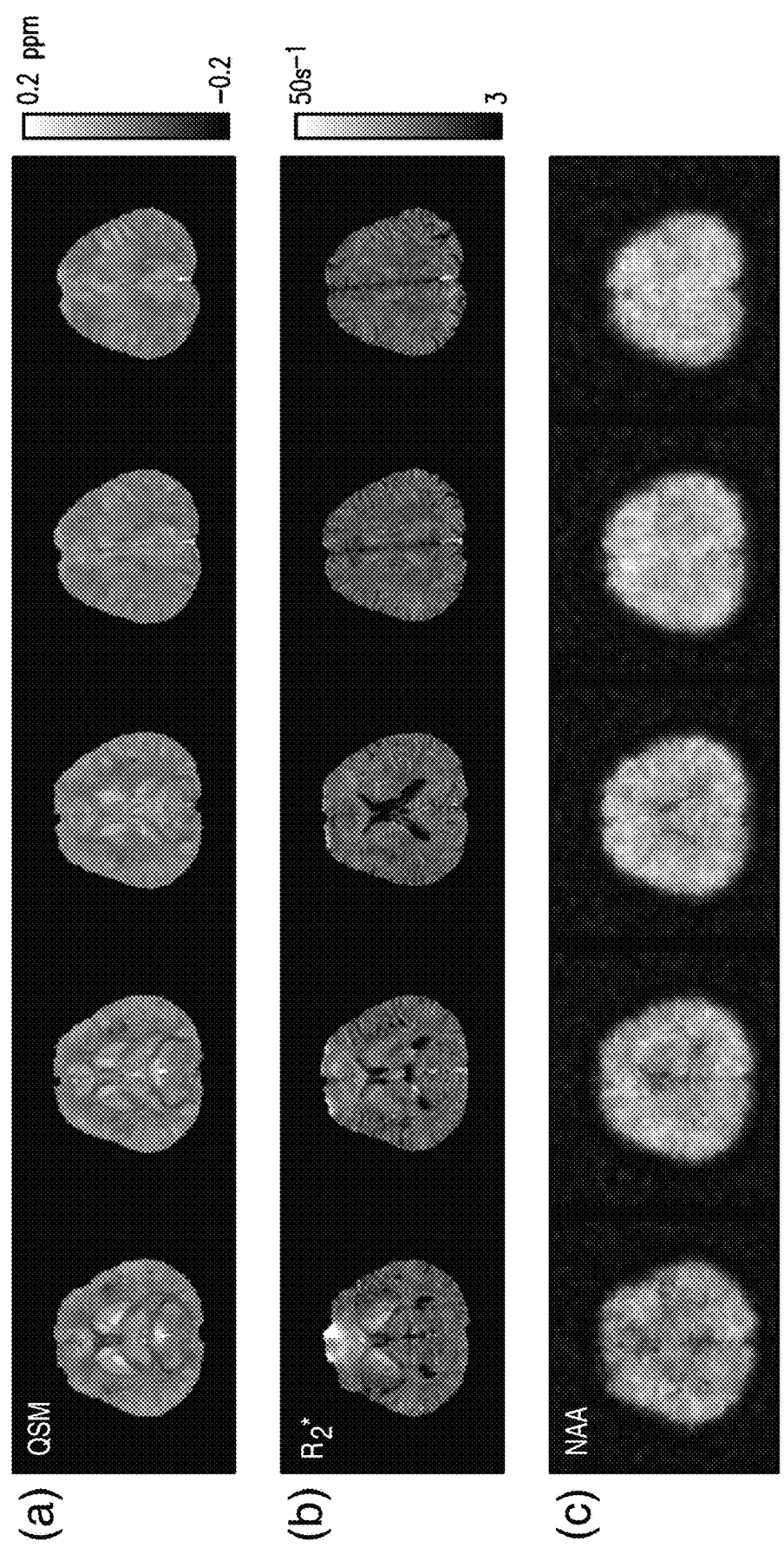
FIG. 6 shows a set of representative results from a healthy volunteer demonstrating the capability of simultaneous QSM and metabolite mapping using a single $^1$H-MRSI scan according to an embodiment. Rows (ab) show tissue susceptibility and $R_2$* maps for different 3D slices across the brain, reconstructed at a 1×1×2 $mm^3$ resolution; row (c) shows 3D metabolite maps (i.e., NAA molecule) for the corresponding slices, reconstructed at a 3×3×3 $mm^3$ resolution.

Since ultrashort-TE excitation without any water suppression is used, the acquisition of this embodiment also encodes much richer information than conventional water-suppressed, medium-to-long-TE MRSI acquisitions. In particular, it offers unique self-calibrating capability and enables the extraction of various kinds of valuable information from the water spectroscopic signals. Specifically, structural information, $B_0$ field inhomogeneity maps, and coil sensitivity maps can all be obtained from the unsuppressed water signals. Using interleaved water navigators, $B_0$ field drift and head motion can be tracked and corrected for. This not only eliminates the need for additional auxiliary scans required in standard MRSI acquisitions 6A, improves the consistency between the MRSI data and the calibration data, but also minimizes the effects of water saturation on the metabolite signals (66A). Furthermore, using the UoSS-based processing and reconstruction described herein, a brand-new capability has been developed of simultaneous mapping brain metabolites, macromolecules (only observed in ultrashort/short-TE data) and neural tissue magnetic susceptibility using a single FID-SPICE scan. As previously established (67A), tissue susceptibility is inherently encoded in the phase variations of the water signals across different echo times, which are attainable from the non-water-suppressed spectroscopic data. More specifically, the tissue relaxation constants and the total field inhomogeneity maps were obtained by performing a least-squares fitting of the multi-echo water signals, which were then followed by background field removal and dipole inversion to generate the quantitative tissue susceptibility maps (QSM) (68A). After the QSM processing, the water/lipid signals were removed for the metabolite spatiospectral reconstruction. A set of representative QSM, $T_2$*, and metabolite maps, all obtained from a single 7 min FID-SPICE scan of a healthy volunteer, are shown in FIG. 6, which would require separate lengthy scans in conventional imaging paradigms. It is believed that this is the first time such a joint imaging experiment has ever been attempted.

Figure 7:
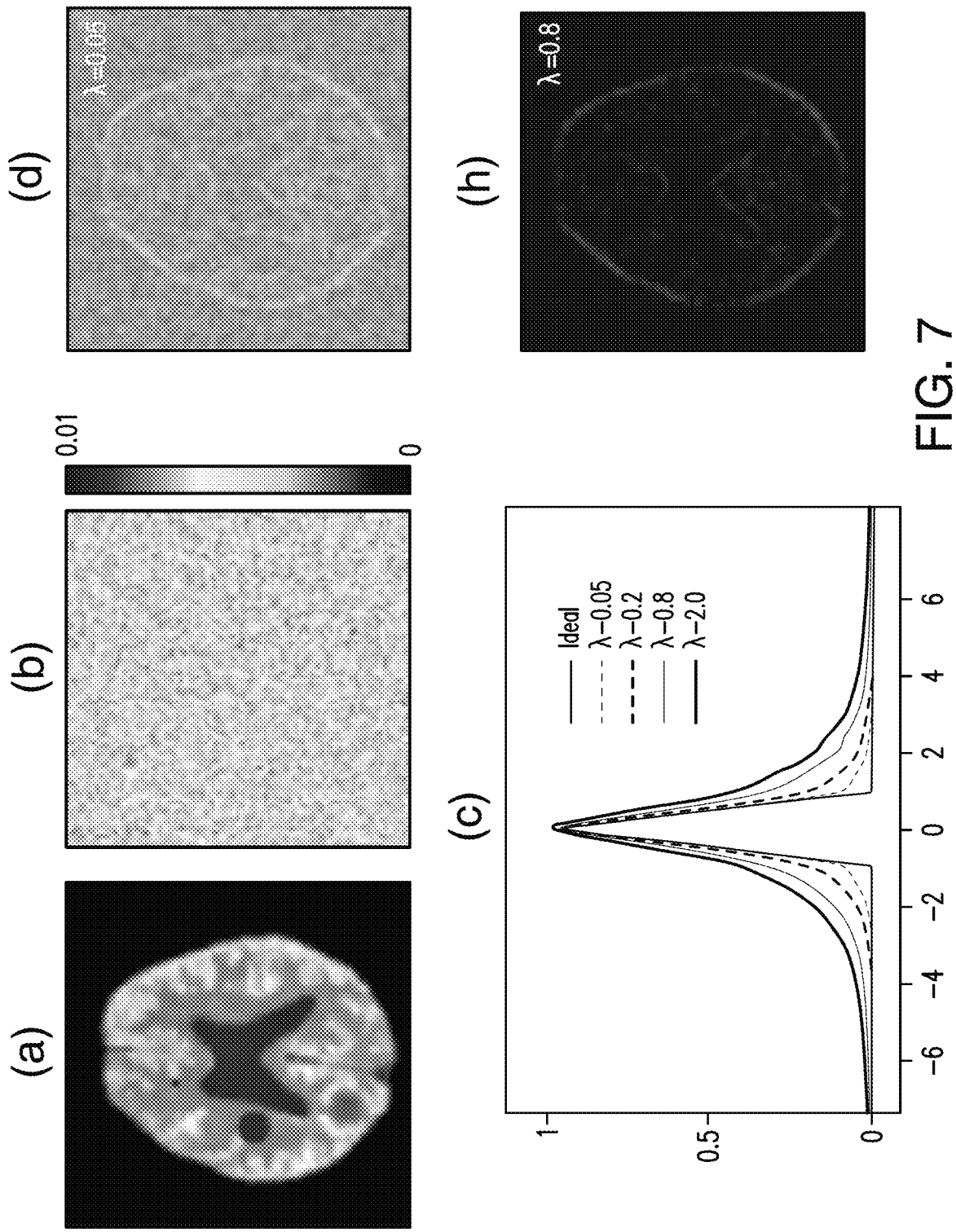
FIG. 7 shows Monte-Carlo simulation results demonstrating the balance between SNR improvements and resolution offered by the method according to an embodiment. Portion (a) of FIG. 7 shows the true spatial map for the dominant resonance frequency component of NAA, notice the artificial features created for evaluating PSF; portion (b) of FIG. 7 shows the maps of variances (all the voxels) from 100 simulated EPSI scans with independent noise realizations; portion (c) of FIG. 7 shows the PSFs for the SPICE reconstructions obtained with a model order of 10 and different values for the regularization parameters ($\lambda_1$); portions (d,f,h,j) of FIG. 7 show the variance maps for SPICE reconstructions from 100 independent trials with the same noise levels as in the EPSI scans used to generate portion (b). The different regularization parameter values used are shown in the top right corners of portion (d),(f),(h) and (j), respectively; portions (e,g,i,k) show the reconstructed value for a particular voxel (in GM) at the first echo across different realizations, for both the EPSI scan (black cross) and the method according to an embodiment (circle). Significantly reduced variations, thus improved reproducibility, can be observed.
Figure 7:
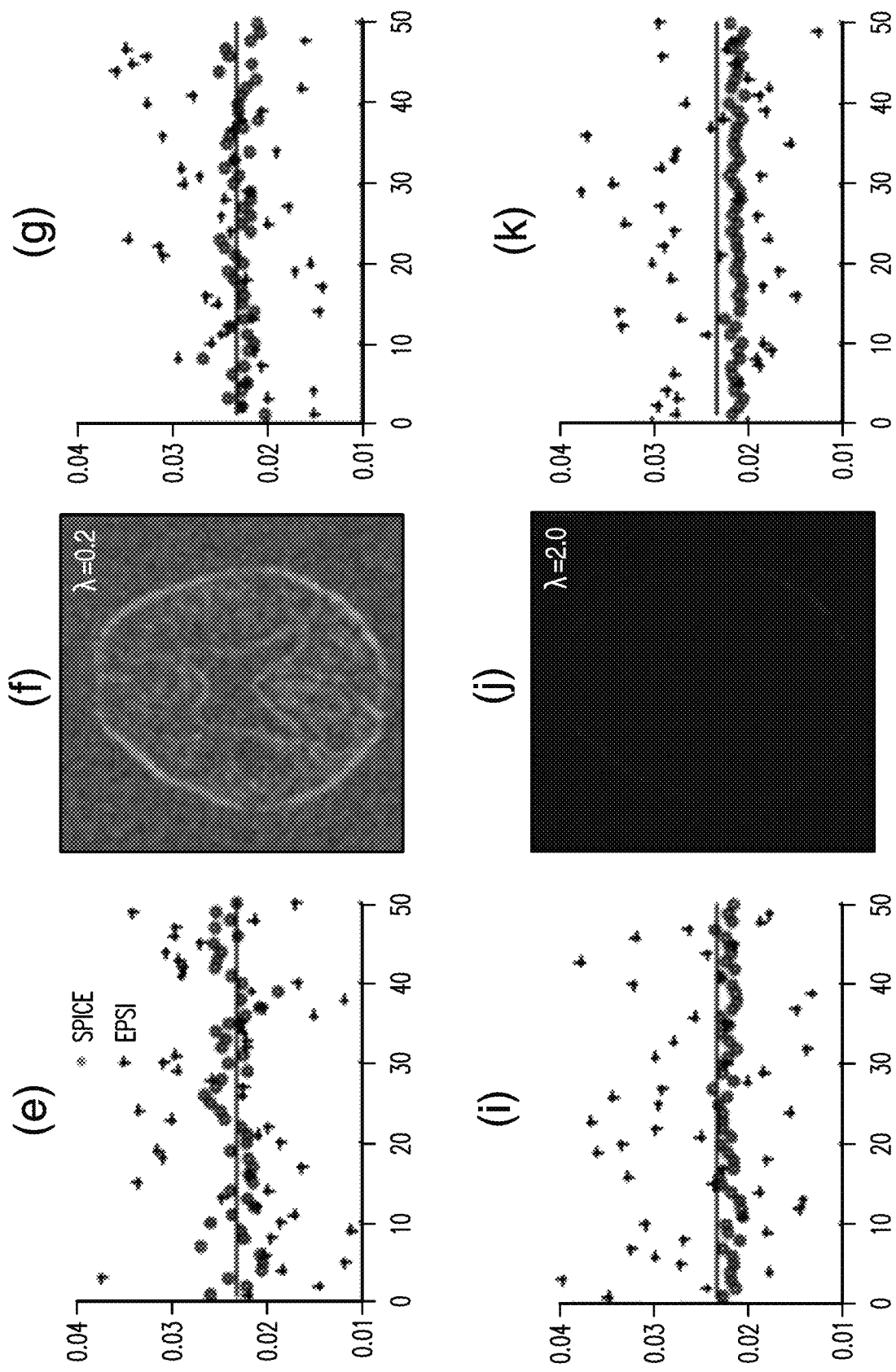

Reference will now be made to certain Validation. To further demonstrate the combination of speed, resolution and SNR achieved by the ultrafast MRSI technology of an embodiment, simulations were performed to validate the SNR improvement offered by the subspace constraint and spatial regularization, and the resolution variations for different regularization levels. A numerical phantom was synthesized with spatially varying metabolite spectra. The true NAA distribution is shown in portion (a) of FIG. 7. Fully-sampled EPSI scans with a realistic noise level were simulated and portion (b) of FIG. 7 shows the variance map for the NAA peak values from 100 independent Fourier reconstructions. The significant variance reduction (SNR improvement) can be clearly observed in the variance maps for reconstructions produced from equivalent-time, short-TR acquisitions by the spatially-regularized, subspace-based reconstruction (portions (d), (f), (h), (j) of FIG. 7. The NAA peak values for a selected voxels are also shown to further illustrate the variance reduction (portions (e), (g), (i), (k) of FIG. 7). As expected, the larger the regularization parameter, the more variance reduction can be achieved, with increased bias and broadened point spread function (PSF). However, note that the regularization level needs not be very strong (only slightly broadened PSF as shown in portion (c) of FIG. 7) to produce a dramatic noise reduction, owing to the low dimensionality of the subspace model.

As described herein, an unprecedented technology has been presented that enables rapid, ultrahigh-resolution MRSI of the whole brain, with the capability to simultaneously map magnetic susceptibility, metabolite, and macromolecule profiles in neural tissues. Table 1 below summarizes the key technical features of the method of this embodiment (coined FID-SPICE) with comparison to several state-of-the-art MRSI methods, to highlight the impressive capability. Such capability, it is believed, can help pave the way for the practical applications of high-resolution MRSI, opening up new opportunities for in vivo metabolic studies of the brain in various neuroscience and clinical investigations. Note that while impressive 2D MRSI results have recently been produced on ultrahigh-field scanners (e.g., 7 and 9.4 T scanners) (35A, 36A), the subspace-based acquisition and processing strategies can be readily extended to these systems and achieve even better performance by taking advantage of the improved sensitivity and higher frequency dispersion.

TABLE 1

| Methods | Resolution (mm$^3$) | Scan time | Field strength | Other features |
| --- | --- | --- | --- | --- |
| FID-SPICE | 2.5 × 2.5 × 3 (3D) | 12 sec/slice | 3 T | No suppression |
| EPSI[69] | 5.6 × 5.6 × 10 (3D) | 80 sec/slice | 3 T | Water/lipid suppressed |
| PCSI[73] | 6.25 × 6.25 × 15 (2D) | 4.5 min/slice | 3 T | Frequency sweep |
| FID-CSI[79] | 2.2 × 2.2 × 8 (2D) | 4.2 min/slice | 7 T | Water suppressed |
| FID-CSI[36] | 3 × 3 × 3 (3D) | 1.4 min/slice | 9.4 T | Water/lipid suppressed |

$^1$H-MRSI experiments have been simplified according to various embodiments by eliminating the need for sophisticated water and lipid suppression modules. Besides allowing for more flexible experimental designs by 1) reducing the burden or complexity in optimizing the RF pulses and gradients for saturation, and 2) alleviating the SAR issue especially when translating the acquisition to higher fields, it also allows all the valuable information to be retained from the water protons. The reference information extracted from the unsuppressed water signals offers improved consistency to the MRSI data compared to the conventional approach where the MRSI data and water referencing data are acquired separately. For signal encoding, the spatiospectral encoding scheme shown herein is just one of the many options to implement the subspace-based acquisition strategy with differential emphasis on spatial and spectral dimensions. Chosen were the echo-planar-based trajectories due to its high efficiency in traversing the (k,t)-space, ease of implementation, lower susceptibility to trajectory errors (due to gradient imperfection), and less computation burden for data processing. But other non-Cartesian trajectories such as radial (70A), spiral (18A) and concentric rings (71A) that offer higher efficiency in covering the (k,t)-space with the potential of further acceleration and/or extended k-space coverage can be considered.

While only the spatiospectral functions that spatially resolve the frequency signatures of different molecules were shown herein, the subspace-based MRSI framework of various embodiments can be extended to consider different contrast mechanisms that have been exploited in water imaging. For example, diffusion encoding can be included to probe the diffusion properties of different metabolites in the brain, which allows for the investigation of intracellular/extracellular compartment specific metabolic processes or microstructural changes under various physiological conditions (72A, 73A). With further optimizations in time-interleaved sampling and data processing, dynamic MRSI experiments are within reach, which should provide an additional dimension of information for studying in vivo metabolism of healthy and diseased tissues (74A) and better understanding of connections between metabolism and brain functions (7A). Moreover, dynamic joint $T_2^*$-weighted functional imaging, susceptibility mapping, and metabolic imaging can also become feasible, which may enable an even broader range of in vivo applications by providing new kinds of comprehensive and efficient imaging exams.

Reference will now be made to certain Methods (Sequence design). There is a lot of flexibility in designing the pulse sequences to implement the subspace-based acquisition strategy. For simplicity, the spoiled steady state design has been adopted in this work, using an α-pulse for excitation and a series of gradient echoes for spatiospectral encoding after each excitation. The slice rephasing gradient was merged with the phase encoding gradients to minimize the acquisition delay (referred to as TE). Given a repetition time (TR), the flip angle, α, was calculated to optimize the SNR efficiency using the following averaged steady-state magnetization formula, considering the range of $T_1$ values for metabolites as between 1000 ms and 2000 ms.

$$A_{FID}(T_R, \alpha, \tau) = \frac{1}{\sqrt{T_R}} \sum_{\omega \in \Omega} \rho(\omega) e^{-TE/T_2^*} \frac{1 - e^{-T_R/T_1(\omega)}}{1 - \cos\alpha e^{-T_R/T_1(\omega)}} \sin\alpha,$$ [Equation 4A]

where ω denotes the frequency component of different metabolites, and Ω↑ the frequency range of interest. $\rho(\omega)$ and $T_1(\omega)$ denote the spin densities and $T_1$ values of individual metabolites, respectively. Within each TR, the EPSI-like trajectories simultaneously cover the frequency encoding dimension ($k_x$) and the chemical shift/spectral dimension, generating between 90 to 100 echoes per excitation, a number significantly smaller than those in typical EPSI scans. Furthermore, because of the extended k-space coverage along $k_x$ to achieve the desired resolution, the spacing between gradient echoes does not satisfy the spectral Nyquist (16A, 17A). The spoiler gradients immediately follow the echo trains so that the TR is minimized. The entire acquisition period composes of five to six segments, each of which covers a portion of the phase encoding dimensions ($k_y$, $k_z$) and takes about 1 minute to acquire. The data segments follow a center-out version, i.e., the k-space locations closer to the origin of the ($k_y$, $k_z$)-plane are sampled earlier in time. This sampling scheme is more robust to motion and other time-dependent system instabilities. A set of navigators, including one FID at the central k-space and three orbital readouts, were interleaved into the acquisition period to track $B_0$ inhomogeneity drift and subject head motion.

Reference will now be made to certain Phantom construction and experiments The brain metabolite phantom is a polymethylpentene cylindrical jar fully filled with sodium chloride doped water and contains nine vials glued to the cap with three different diameters (see portion (a) of FIG. 4). The vials were filled with solutions of N-acetylaspartate (NAA), creatine (Cr), glycerophosphocholine (Cho), myo-inositol (mI), glutamate (Glu) and γ-aminobutyric acid (GAB A) at physiological concentrations (6A). More specifically, four different concentration ratios were designed: (group 1) 16 mM NAA, 14 mM Cr, 5 mM Cho, 8 mM mI, 15 mM Glu, 3 mM GABA; (group 2) 14 mM NAA, 12 mM Cr, 4 mM Cho, 7 mM mI, 8 mI Glu, 3 mI GABA; (group 3) 10 mM NAA, 10 mM Cr, 5 mM Cho, 5 mM mI, 10 mM Glu, 3 mM GABA; (group 4) 8 mM NAA, 8 mM Cr, 10 mM Cho, 10 mM mI, 8 mM Glu, 1 mM GABA. The pH value for all the solutions was adjusted to approximately 7.2 using concentrated NaOH and HCL. The phantom was sealed with teflon tapes to avoid leaking and air getting into the jar.

All the experiments were conducted on a Siemens Prisma 3T scanner equipped with a 20-channel head coil (Siemens Healthineers, Erlangen, Germany). The CSI data were acquired with the following parameters: TR/TE=510/2.3 ms, FOV (field-of-view)=210×210×10 mm³, matrix size=64×64 (approximately 3.3×3.3×10 mm³ voxel size), 60 Hz WET water suppression, and 512 FID samples with 2000 Hz spectral bandwidth (BW). The FID-SPICE data were acquired with the same FOV and matrix size, TR/TE=210/2.3 ms, flip angle (FA)=31°, readout BW=167 kHz, and the number of echo pairs (for each train)=90. A dual-echo GRE scan was performed with matched geometry and a matrix size of 128×128 to provide both high-resolution structural information and the B0field inhomogeneity.

Reference will now be made to certain In Vivo experiments. Brain ¹H-MRSI data were acquired from healthy volunteers, with local institutional review board approval and participants' consent. The high-resolution 3D MRSI data were acquired using the following parameters: TR/TE=210/4 ms, flip angle=31°, FOV=240×240×72 mm³, matrix size=110×96×24 ($k_x$×$k_y$×$k_z$), readout BW=167 kHz, and number of echo pairs=92 with an echospacing of 1780 us. Two saturation bands on the top and bottom of the FOV were included to minimize the signals coming from outside of the excitation volume. The total acquisition time is 5 min with the central 36×24 ($k_y$, $k_z$)-plane fully sampled and a factor of two undersampling in the outer region. For some data used for simultaneous susceptibility and metabolite mapping, the acquisition time is around 7 min for a matrix size of 124×120×32. An MPRAGE (magnetization prepared rapid gradient-echo) image is acquired before the MRSI scan, with the following parameters: TR/TE/TI=1900/2.29/900 ms, flip angle=9°, FOV=240×240×192 mm³, matrix size=256×256×192, bandwidth/pixel=200 Hz and 4.5 min acquisition time. The MPRAGE data were used for better localization of the MRSI volume, and obtaining the spatial supports of the brain-only region and the subcutaneous layer for subsequent data processing (e.g., water and lipid removal) (63A). The segmentation was done using the SPM12 software package (http://www.fil.ion.ucLac.uk/spm/software/spm12/). $T_2$-weighted images were also acquired using a fast spin echo (FSE) sequence in the end with matching geometry to the MRSI scan, 24 slices, matrix size=128×128, TR/TE=4000/88 ms, flip angle=120°, turbo factor=11, number of echoes per echo train=7, echo spacing=8.82 ms, bandwidth/pixel=222 Hz, and acquisition time=30 seconds. Image voxel coordinates were extracted from these images for interpolating the segmented images to the coordinates of the MRSI grids.

Reference will now be made to certain Image reconstruction The multiple-channel coil used for data acquisition generates multiple measurements for each k-space location which can be used to interpolate the missing samples in the undersampled k-space. To this end, an initial GRAPPA interpolation of first 32 echoes is performed (31A). The GRAPPA reconstruction were then used to estimate a set of high-SNR and high-resolution sensitivity maps, which were subsequently included in a data-consistent SENSE reconstruction from the original data (29A). All subsequent spatiospectral processing is applied to this coil-combined data.

Reference will now be made to certain Quantitative susceptibility mapping. To extract the susceptibility information, the initial spatiotemporal reconstruction was modeled as follows (the metabolite signal is ignored at this stage because it is negligible compared to the unsuppressed water/lipid signals)

$$\rho(r;t_m)=[\rho_w(r)+\rho_l(r)\phi_l(t_m)]e^{-R^*_2(r)t_m}e^{i2\pi\Delta f(r)t_m}+\in(r,t_m),\quad \text{[Equation 5A]}$$

where $\rho_w(r)$ and $\rho_l(r)$ denote the concentrations of water and lipids (with weighting), $\phi_l(t_m)=\Sigma_j\alpha_j\in^{-2\pi f_j t_m}$ the lipid spectral structural, $R^*_2(r)$ the apparent relaxation constant, $\Delta f(r)$ the total field inhomogeneity which composes of the background field $f_b(r)$ and the tissue susceptibility-induced frequency offset $f_t(r)$, and $\in(r, t_m)$ the noise term. Using this model, a voxel-by-voxel nonlinear least-squares fitting was performed to jointly estimate $R^*_2(r)$ and $\Delta f(r)$ utilizing all the echoes available. The background field was removed from $\Delta f(r)$ by solving a Laplacian boundary value problem (75A) to extract $f_t(r)$. A dipole inversion with a weighted-$\ell_1$ regularization was then solved to estimate the susceptibility map, $\chi(r)$, from $f_t(r)$ (67A). The reconstructed images in Eq. (5A) were zero-padded to a resolution of 1×1×1 mm³ before fitting, and the weighting coefficients for the regularized dipole inversion were calculated from the MPRAGE image. The estimated total field $\Delta f(r)$ was also saved for subsequent metabolite processing.

Reference will now be made to certain Metabolite spatiospectral reconstruction. After extracting the information needed, the water and lipid signals need to be removed for metabolite reconstruction. To this end, the water and lipid signal subspaces were determined by performing a voxel-by-voxel fitting to the coil-combined data using a more relaxed model than Eq. (5A) (i.e., use multiple peaks for water and allow the relative coefficients for different lipid peaks to vary). The lipid distribution was further modified by performing a support-constrained data extrapolation (42A), for which the subcutaneous lipid layer segmented previously from the MPRAGE was used. The estimated water and lipid distributions were arranged into Casorati matrices (45A) to which SVD analysis was applied to extract the singular vectors as the their temporal bases. The UoSS fitting described in (63A) were then applied to re-estimate the water and lipid spatiotemporal distributions with higher accuracy, whose contributions were subsequently subtracted from the data. This subspace-based scheme offers significantly cleaner removal compared to the conventional voxel-by-voxel water removal (e.g., HSVD (41A)), which is susceptible to modeling errors due to inter and intra-voxel field inhomogeneity, partial volume and noise effects, and also prevents the removal of metabolite signals with the spatiospectral constraints incorporated.

After water/lipid removal, a joint spatiospectral reconstruction of the metabolite and macromolecule components is done by solving the following optimization problem:

$$\hat{C}_m, \hat{C}_{MM} = \underset{C_m, C_{MM}}{\arg\min} \|d - \Omega\{FB \odot (C_m\Phi_m + C_{MM}\Phi_{MM})\}\|_2^2 + \lambda_1\|D_w C_m\|_F^2 + \lambda_2\|C_{MM}\|_F^2 \quad \text{[Equation 6A]}$$

where the first term enforces data consistency incorporating the subspace model and field inhomogeneity correction, and the next two terms impose spatial regularization. $\Phi_m \in \mathcal{C}^{L_m \times N_f}$ and $\Phi_{MM} \in \mathcal{C}^{L_{MM} \times N_f}$ are matrix representations of the metabolite and macromolecule bases, respectively, with $C_m \in \mathcal{C}^{N \times L_m}$ and $C_{MM} \in \mathcal{C}^{N \times L_{MM}}$ the corresponding spatial coefficients. B is a matrix, with $B_{nm}=e^{i2\pi\Delta f(r_n)t_m}$, modeling the field inhomogeneity effects, F denotes the Fourier encoding operator, $\Omega$ is a general (k,t)-space sampling operator, and the vector d, contains the water/lipid-removed data. A weighted-$\ell_2$ regularization is employed for the metabolite spatial coefficients, with weights derived from the water images using the Laplacian operator (62A), while a standard $\ell_2$ regularization is employed for the macromolecule coefficients. Quadratic regularization is chosen for demonstrating imaging capability (according to various embodiments) based on the considerations for computation speed and resolution characterization, although nonquadratic/sparsity-promoting regularization can be used for further improved reconstruction (62A).

Reference will now be made to certain Metabolite subspace estimation. Training data were acquired from multiple subjects to predetermine the subspaces for metabolite and macromolecule components. For each subject, a 3D low-resolution EPSI acquisition was performed to capture metabolite spectra variations and a 2D CSI acquisition with an inversion recovery based metabolite nulling module was performed to capture the MM spectral variations (76A, 77A). The metabolite training data had 310/4 ms TR/TE, 16×16×12 matrix size, 220×220×72 mm³ FOV, 68 kHz readout BW, 1.56 kHz spectral BW, 320 echoes and two signal averages, while the MM training data had 1500/3 ms TR/TE, 520 ms TI (recovery time), 26×26 matrix size, 220×220 mm² FOV, 10 mm slice thickness, 2 kHz spectral BW, and 480 FID samples. Both data were acquired with water suppression and carefully placed outer volume suppression bands to reduce the subcutaneous lipid signals. The residual water and lipid signals were removed using the method described in (63A). $B_0$ inhomogeneity correction was performed (62A) after water/lipid removal. The metabolite and MM spectra from different subjects were pooled together to estimate the subspaces for individual components, respectively.

References 1A-79A

1A. Massoud, T. F. & Gambhir, S. S. Molecular imaging in living subjects: seeing fundamental biological processes in a new light. Genes Dev. 17, 545-580 (2003).

2. A. Weissleder, R., Ross, B. D., Rehemtulla, A. & Gambhir, S. S. Molecular Imaging: Principles and Practice (Shelton, Conn.: PMPH-USA, Limited, 2010).
3. A. Brown, T. R., Kincaid, B. M. & Ugurbil, K. NMR chemical shift imaging in three dimensions. Proc. Natl. Acad. Sci. 79, 3523-3526 (1982).
4. A. Lauterbur, P. C., Kramer, D. M., House, W. V. & Chen, C.-N. Zeugmatographic high resolution nuclear magnetic resonance spectroscopy: Images of chemical inhomogeneity within macroscopic objects. J. Amer. Chem. Soc. 97, 6866-6868 (1975).
5. A. Maudsley, A. A., Hilal, S. K., Perman,W. H. & Simon, H. E. Spatially resolved high resolution spectroscopy by "four-dimensional" NMR. J. Magn. Reson. 51, 147-152 (1983).
6. A. de Graaf, R. A. In Vivo NMR Spectroscopy: Principles and Techniques (Hoboken, N.J.: John Wiley and Sons, 2007).
7. A. Mangia, S. et al. Sustained neuronal activation raises oxidative metabolism to a new steadystate level: Evidence from 1H NMR spectroscopy in the human visual cortex. J. Cereb. Blood Flow Metab. 27, 1055-1063 (2007).
8. A. Novotny, E. J., Fulbright, R. K., Pearl, P. L., Gibson, K. M. & Rothman, D. L. Magnetic resonance spectroscopy of neurotransmitters in human brain. Ann. Neurol. 54, S25-S31 (2003).
9. A. Shulman, R. G., Rothman, D. L., Behar, K. L. & Hyder, F. Energetic basis of brain activity: implications for neuroimaging. Trends Neurosci. 27, 489-495 (2004).
10. A. Martin, W. R. W. MR spectroscopy in neurodegenerative disease. Mol. Imaging Biol. 9, 196-203 (2007).
11. A. Kurhanewicz, J., Vigneron, D. B. & Nelson, S. J. Three-dimensional magnetic resonance spectroscopic imaging of brain and prostate cancer. Neoplasia 2, 166-189 (2000).
12. A. Choi, C. et al. 2-hydroxyglutarate detection by magnetic resonance spectroscopy in IDHmutated patients with gliomas. Nat Med 18, 624-629 (2012).
13. A. Shim, H. et al. Use of high-resolution volumetric MR spectroscopic imaging in assessing treatment response of glioblastoma to an HDAC inhibitor. Am. J. Roentgenol. 203, W158-W165 (2014).
14. A. Bizzi, A. et al. Response of non-Hodgkin lymphoma to radiation therapy: early and long-term assessment with H-1 MR spectroscopic imaging. Radiology 194, 271-276 (1995).
15. A. Luyten, P. R. et al. Metabolic imaging of patients with intracranial tumors: H-1 MR spectroscopic imaging and PET. Radiology 176, 791-799 (1990).
16. A. Mansfield, P. Spatial mapping of the chemical shift in NMR. Magn. Reson. Med. 1, 370-386 (1984).
17. A. Posse, S., Tedeschi, G., Risinger, R., Ogg, R. & Le Bihan, D. High speed 1H spectroscopic imaging in human brain by echo planar spatial-spectral encoding. Magn. Reson. Med. 33, 34-40 (1995).
18. A. Adalsteinsson, E. et al. Volumetric spectroscopic imaging with spiral-based k-space trajectories. Magn. Reson. Med. 39, 889-898 (1998).
19. A. Maudsley, A. A. et al. Mapping of brain metabolite distributions by volumetric proton MR spectroscopic imaging (MRSI). Magn. Reson. Med. 61, 548-559 (2009).
20. A. Schirda, C. V., Tanase, C. & Boada, F. E. Rosette spectroscopic imaging: Optimal parameters for alias-free, high sensitivity spectroscopic imaging. J. Magn. Reson. Imag. 29, 1375-1385 (2009).
21. A. Pohmann, R., von Kienlin, M. & Haase, A. Theoretical evaluation and comparison of fast chemical shift imaging methods. J. Magn. Reson. 129, 145-160 (1997).
22. A. Andronesi, O. C., Gagoski, B. A. & Sorensen, A. G. Neurologic 3D MR spectroscopic imaging with low-power adiabatic pulses and fast spiral acquisition. Radiology 262, 647-661 (2012).
23. A. Hu, X., Levin, D. N., Lauterbur, P. C. & Spraggins, T. SLIM: Spectral localization by imaging. Magn. Reson. Med. 8, 314-322 (1988).
24. A. Liang, Z.-P. & Lauterbur, P. C. A generalized series approach to MR spectroscopic imaging. IEEE Trans. Med. Imag. 10, 132-137 (1991).
25. A. Haldar, J. P., Hernando, D., Song, S. K. & Liang, Z.-P. Anatomically constrained reconstruction from noisy data. Magn. Reson. Med. 59, 810-818 (2008).
26. A. Zhang, Y., Gabr, R. E., Schar, M., Weiss, R. G. & Bottomley, P. A. Magnetic resonance spectroscopy with linear algebraic modeling (SLAM) for higher speed and sensitivity. J. Magn. Reson. 218, 66-76 (2012).
27. A. Eslami, R. & Jacob, M. Robust reconstruction of MRSI data using a sparse spectral model and high resolution MRI priors. IEEE Trans. Med. Imag. 29, 1297-1309 (2010).
28. A. Kasten, J., Klauser, A., Lazeyras, F. & Ville, D. V. D. Magnetic resonance spectroscopic imaging at superresolution: Overview and perspectives. J. Magn. Reson. 263, 193-208 (2016).
29. A. Dydak, U., Weiger, M., Pruessmann, K. P., Meier, D. & Boesiger, P. Sensitivity-encoded spectroscopic imaging. Magn. Reson. Med. 46, 713-722 (2001).
30. A. Lin, F.-H. et al. Sensitivity-encoded (SENSE) proton echo-planar spectroscopic imaging (PEPSI) in the human brain. Magn. Reson. Med. 57, 249-257 (2007).
31. A. Tsai, S.-Y. et al. Accelerated proton echo planar spectroscopic imaging (PEPSI) using GRAPPA with a 32-channel phased-array coil. Magn. Reson. Med. 59, 989-998 (2008).
32. A. Henning, A., Fuchs, A., Murdoch, J. B. & Boesiger, P. Slice-selective FID acquisition, localized by outer volume suppression (FIDLOVS) for 1H-MRSI of the human brain at 7T with minimal signal loss. NMR Biomed. 22, 683-696 (2009).
33. A. Bogner, W., Gruber, S., Trattnig, S. & Chmelik, M. High-resolution mapping of human brain metabolites by free induction decay 1H MRSI at 7T. NMR Biomed. 25, 873-882 (2012).
34. A. Povazan, M. et al. Mapping of brain macromolecules and their use for spectral processing of 1H-MRSI data with an ultra-short acquisition delay at 7 T. Neurolmage 121, 126-135 (2015).
35. A. Strasser, B. et al. (2+1)D-CAIPIRINHA accelerated MR spectroscopic imaging of the brain at 7T. Magn Reson Med (2016). DOI: 10.1002/mrm.26386.
36. A. Chadzynski, G. L. et al. Fast and efficient free induction decay MR spectroscopic imaging of the human brain at 9.4 Tesla. Magn. Reson. Med. (2016). Doi: 10.1002/mrm.26539.
37. A. Posse, S., Otazo, R., Dager, S. R. & Alger, J. MR spectroscopic imaging: Principles and recent advances. J. Magn. Reson. Imag. 37, 1301-1325 (2013).
38. A. Haase, A., Frahm, J., Hanicke, W. & Matthaei, D. 1H NMR chemical shift selective (CHESS) imaging. Phys. Med. Biol. 30, 341 (1985).

39. A. Ogg, R. J., Kingsley, R. B. & Taylor, J. S. WET, a T1- and B1-insensitive water-suppression method for in vivo localized 1H NMR spectroscopy. J. Magn. Reson. 104, 1-10 (1994).
40. A. Duyn, J. H., Gillen, J., Sobering, G., van Zijl, P. C. & Moonen, C. T. Multisection proton MR spectroscopic imaging of the brain. Radiology 188, 277-282 (1993).
41. A. Barkhuysen, H., de Beer, R. & van Ormondt, D. Improved algorithm for noniterative time domain model fitting to exponentially damped magnetic resonance signals. J. Magn. Reson. 73, 553-557 (1987).
42. A. Haupt, C. I., Schuff, N., Weiner, M. W. & Maudsley, A. A. Removal of lipid artifacts in 1H spectroscopic imaging by data extrapolation. Magn. Reson. Med. 35, 678-687 (1996).
43. A. Liang, Z.-P. Spatiotemporal imaging with partially separable functions. In Proc. IEEE Int. Symp. on Biomed. Imag., 988-991 (Arlington, Va., USA, 2007).
44. A. Nguyen, H. M., Peng, X., Do, M. N. & Liang, Z.-P. Denoising MR spectroscopic imaging data with low-rank approximations. IEEE Trans. Biomed. Eng. 60, 78-89 (2013).
45. A. Lam, F. & Liang, Z.-P. A subspace approach to high-resolution spectroscopic imaging. Magn. Reson. Med. 71, 1349-1357 (2014).
46. A. Ma, D. et al. Magnetic resonance fingerprinting. Nature 495, 187-192 (2013).
47. A. Cloos, M. A. et al. Multiparametric imaging with heterogeneous radiofrequency fields. Nat. Commun. 7, 12445 EP (2016).
48. A. Liang, Z.-P. & Lauterbur, P. C. Principles of Magnetic Resonance Imaging: A Signal Processing Perspective (IEEE Press, New York, 2000).
49. A. Lustig, M., Donoho, D. L. & Pauly, J. M. Sparse MRI: The application of compressed sensing for rapid MR imaging. Magn. Reson. Med. 1182-1195 (2007).
50. A. Zhu, L., Zhang, W., Elnatan, D. & Huang, B. Faster STORM using compressed sensing. Nat. Meth. 9, 721-723 (2012).
51. A. Gao, L., Liang, J., Li, C. & Wang, L. V. Single-shot compressed ultrafast photography at one hundred billion frames per second. Nature 516, 74-77 (2014).
52. A. Haldar, J. P., Hernando, D. & Liang, Z.-P. Compressed-sensing MRI with random encoding. IEEE Trans. Med. Imag. 30, 893-903 (2011).
53. A. Jung, H., Sung, K., Nayak, K. S., Kim, E. Y. & Ye, J. C. k-t FOCUSS: A general compressed sensing framework for high resolution dynamic MRI. Magn. Reson. Med. 61, 103-116 (2009).
54. A. Liang, D., Liu, B., Wang, J. & Ying, L. Accelerating SENSE using compressed sensing. Magn. Reson. Med. 62, 1574-1584 (2009).
55. A. Otazo, R., Kim, D., Axel, L. & Sodickson, D. K. Combination of compressed sensing and parallel imaging for highly accelerated first-pass cardiac perfusion MRI. Magn. Reson. Med. 64, 767-776 (2010).
56. A. Cand'es, E., Romberg, J. & Tao, T. Robust uncertainty principles: Exact signal reconstruction from highly incomplete frequency information. IEEE Trans. Inf. Theory 52, 489-509 (2006).
57. A. Donoho, D. L., Maleki, A. & Montanari, A. The noise-sensitivity phase transition in compressed sensing. IEEE Trans. Inf. Theory 57, 6920-6941 (2011).
58. A. Larson, P. E. Z. et al. Fast dynamic 3D MR spectroscopic imaging with compressed sensing and multiband excitation pulses for hyperpolarized 13C studies. Magn. Reson. Med. 65, 610-619 (2011).
59. A. Cao, P. & Wu, E. X. Accelerating phase-encoded proton MR spectroscopic imaging by compressed sensing. J. Magn. Reson. Imag. 41, 487-495 (2015).
60. A. Chatnuntawech, I. et al. Accelerated 1H MRSI using randomly undersampled spiral-based k-space trajectories. Magn. Reson. Med. 74, 13-24 (2014).
61. A. Wilson, N. E., Iqbal, Z., Burns, B. L., Keller, M. & Thomas, M. A. Accelerated five dimensional echo planar J-resolved spectroscopic imaging: Implementation and pilot validation in human brain. Magn. Reson. Med. 75, 42-51 (2016).
62. A. Lam, F., Ma, C., Clifford, B., Johnson, C. L. & Liang, Z.-P. High-resolution 1H-MRSI of the brain using SPICE: Data acquisition and image reconstruction. Magn. Reson. Med. 76, 1059-1070 (2016).
63. A. Ma, C., Lam, F., Johnson, C. L. & Liang, Z.-P. Removal of nuisance signals from limited and sparse 1H MRSI data using a union-of-subspaces model. Magn. Reson. Med. 75, 488-497 (2016).
64. A. Ma, C., Lam, F., Ning, Q., Johnson, C. L. & Liang, Z.-P. High-resolution 1H-MRSI of the brain using short-TE SPICE. Magn. Reson. Med. 77, 467-479 (2017).
65. A. Pohmann, R., von Kienlin, M. & Haase, A. Theoretical evaluation and comparison of fast chemical shift imaging methods. J. Magn. Reson. 129, 145-160 (1997).
66. A. Dong, Z. Proton MRS and MRSI of the brain without water suppression. Prog. Nucl. Magn. Reson. Spectrosc. 86-87, 65-79 (2015).
67. A. Wang, Y. & Liu, T. Quantitative susceptibility mapping (QSM): Decoding MRI data for a tissue magnetic biomarker. Magn. Reson. Med. 73, 82-101 (2015).
68. A. Peng, X., Lam, F., Li, Y., Clifford, B. & Liang, Z.-P. Simultaneous QSM and metabolic imaging of the brain using SPICE. Magn. Reson. Med. 79, 13-21 (2018).
69. A. Maudsley, A. A., Domenig, C. & Sheriff, S. Reproducibility of serial whole-brain MR spectroscopic imaging. NMR Biomed. 23, 251-256 (2010).
70. A. Silva, A. C., Barbier, E. L., Lowe, I. J. & Koretsky, A. P. Radial echo-planar imaging. J. Magn. Reson. 135, 242-247 (1998).
71. A. Chiew, M. et al. Density-weighted concentric rings k-space trajectory for 1H magnetic resonance spectroscopic imaging at 7 T. NMR Biomed. 31, e3838 (2018).
72. A. Van Zijl, P. C. et al. Complete separation of intracellular and extracellular information in NMR spectra of perfused cells by diffusion-weighted spectroscopy. Proc. Natl. Acad. Sci. U.S.A. 88, 3228-3232 (1991).
73. A. Ercan, A. E., Techawiboonwong, A., Versluis, M. J., Webb, A. G. & Ronen, I. Diffusion weighted chemical shift imaging of human brain metabolites at 7T. Magn. Reson. Med. 73, 2053-2061 (2015).
74. A. Taylor, J. M., Zhu, X.-H., Zhang, Y. & Chen, W. Dynamic correlations between hemodynamic, metabolic, and neuronal responses to acute whole-brain ischemia. NMR Biomed. 28, 1357-1365 (2015).
75. A. Zhou, D., Liu, T., Spincemaille, P. & Wang, Y. Background field removal by solving the Laplacian boundary value problem. NMR Biomed. 27, 312-319 (2014).
76. A. Behar, K. L., Rothman, D. L., Spencer, D. D. & Petroff, O. A. C. Analysis of macromolecule resonances in 1H NMR spectra of human brain. Magn. Reson. Med. 32, 294-302 (1994).
77. A. Lam, F., Li, Y., Clifford, B. & Liang, Z. Macromolecule mapping of the brain using ultrashort TE acquisition and reference based metabolite removal. Magn. Reson. Med. 79, 2460-2469 (2018).

78A. Guo, J., Patay, Z. & Reddick, W. E. Fast frequency-sweep spectroscopic imaging with an ultra-low flip angle. Scientific Reports 6, 30066 (2016).

79A. Hangel, G. et al. Ultra-high resolution brain metabolite mapping at 7T by short-TR Hadamard encoded FID-MRSI. NeuroImage (2016). Https://doi.org/10.1016/j.neuroimage.2016.10.043.

Reference will now be made to various embodiments directed to Simultaneous QSM and Metabolic Imaging of the Brain Using SPICE. Various embodiments described herein provide for mapping brain metabolites and tissue magnetic susceptibility simultaneously using a single three-dimensional $^1$HMRSI acquisition without water suppression.

Various embodiments described herein provide a technique that builds on a subspace imaging method called spectroscopic imaging by exploiting spatiospectral correlation (SPICE), which enables ultrashort echo time (TE)/short pulse repetition time (TR) acquisitions for $^1$H-MRSI without water suppression. This data acquisition scheme simultaneously captures both the spectral information of brain metabolites and the phase information of the water signals that is directly related to tissue magnetic susceptibility variations. In extending this scheme for simultaneous QSM and metabolic imaging, k-space coverage is increased by using dual density sparse sampling and ramp sampling to achieve spatial resolution often required by QSM, while maintaining a reasonable signal-to-noise ratio (SNR) for the spatiospectral data used for metabolite mapping. In data processing, high-quality QSM is obtained from the unsuppressed water signals by taking advantage of the larger number of echoes acquired and any available anatomical priors; metabolite spatiospectral distributions are reconstructed using a union-of-subspaces model.

In vivo experimental results demonstrate that the method of an embodiment can produce susceptibility maps at a resolution higher than 1.8×1.8×2.4 mm$^3$ along with metabolite spatiospectral distributions at a nominal spatial resolution of 2.4×2.4×2.4 mm$^3$ from a single 7-min MRSI scan. The estimated susceptibility values are consistent with those obtained using the conventional QSM method with 3D multi-echo gradient echo acquisitions.

As described herein is a new capability for simultaneous susceptibility mapping and metabolic imaging of the brain from a single $^1$H-MRSI scan, which has potential for a wide range of applications.

Quantitative susceptibility mapping (QSM) has been widely used in recent years for in vivo mapping of tissue magnetic susceptibility (1B) [references 1B-38B below are referred to herein by a number followed by the letter "B", e.g., 1B, 2B, etc.], a biomarker useful for detecting intracranial hemorrhages (2B, 3B), quantifying blood vessel oxygenation (4B-6B), and examining iron accumulation in the deep gray matter (GM) (7B). MR spectroscopic imaging (MRSI) has also been recognized as a unique tool to obtain molecule-specific information, allowing in vivo characterization of biochemical properties of tissues (8B). QSM and MRSI, therefore, provide complementary information useful for many research and clinical applications, such as study of brain metabolism (9B-14B), diagnosis and characterization of neurological disorders (15B-18B), and assessment of therapeutic efficacy (19C).

Currently, QSM and MRSI are carried out in separate scans, both of which often require long data acquisition times, limiting their practical use in clinical and research applications. Conventional QSM methods acquire a series of $T_2^*$-weighted images using a high-resolution multi-echo gradient echo (GRE) sequence, which typically takes 5-10 min to cover the whole brain. MRSI scans usually take even longer (e.g., a conventional chemical shift imaging scan can take up to 30 min to cover a single 2D slice with an in-plane resolution of approximately 4×4 mm$^2$). Although a number of methods have been proposed to accelerate QSM and MRSI scans (21B, 22B), it is believed that no simultaneous QSM and MRSI acquisitions have been attempted yet.

Figure 9:
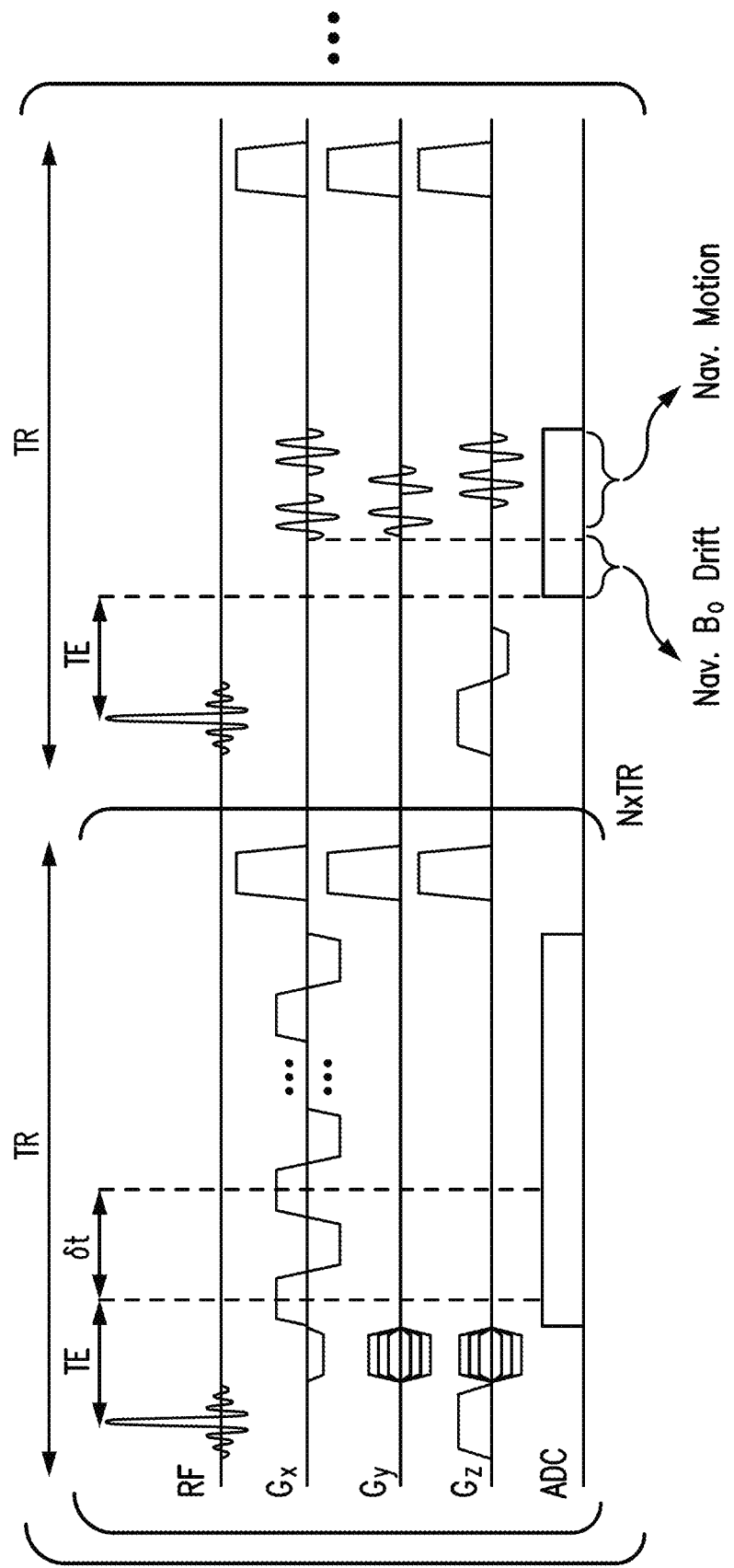
FIG. 9 shows pulse sequence for an embodiment using FID-based acquisitions with ultrashort TE, short TR, no water suppression, bipolar acquisition, and ramp sampling, for simultaneous QSM and metabolic imaging. Navigators are acquired after every N repetitions (e.g., N=50) for field drift and motion tracking.

Described herein is the feasibility of simultaneous QSM and high-resolution metabolite mapping from a single $^1$H-MRSI scan using a new MRSI technique known as spectroscopic imaging by exploiting spatiospectral correlation (SPICE) (23B,24B). This capability is made possible by exploiting the fact that tissue susceptibility information is naturally encoded in the water spectroscopic signals from an MRSI scan if no water suppression is applied (FIG. 9). Conventional MRSI acquisitions usually apply several RF pulses to suppress the water and lipid signals, almost completely eliminating the susceptibility information. This problem is nicely overcome with SPICE, which uses ultrashort echo time (TE)/short pulse repetition time (TR) acquisitions without water suppression (23B,24B). Although SPICE has been used mainly for metabolic imaging, its data acquisition and processing scheme is extended to make it more suitable for simultaneous QSM and metabolic imaging. More specifically, in data acquisition, dual-density sparse sampling and ramp sampling are used to extend k-space coverage to the level often required by QSM, while maintaining a reasonable SNR for the spatiospectral encodings used for metabolic imaging. In data processing, advantage is taken of the larger number of echoes generated by the SPICE sequence (and any readily available anatomical priors) to produce high quality QSM; a union-of-subspaces model is used to reconstruct the metabolite spatiospectral distributions. These features together allow the obtaining of tissue susceptibility maps of the brain at a voxel size of 1.8×1.8×2.4 mm3 (or slightly smaller if the effect of the anatomical constraints is also taken into account) and metabolite maps at a nominal voxel size of 2.4×2.4×2.4 mm from a single 7-min scan. A more detailed description of the acquisition and processing schemes of various embodiments is given subsequently, which is followed by some representative experimental results to demonstrate the performance of the method.

With reference now to Data Acquisition according to an embodiment, this data acquisition scheme retains the main features of the FID-based SPICE sequence illustrated in FIG. 9. First, it uses ultrashort TE/short TR (3 ms/210 ms) acquisitions without water and lipid suppression pulses. Second, EPSI readout is used for rapid spatiospectral encoding with bipolar acquisitions; the EPSI trajectories used here have larger k-space coverage and, for each k-space location, longer echo spacing and much fewer spectral encodings than conventional EPSI trajectories, which are enabled by the SPICE subspace imaging framework. Third, interleaved navigator signals are collected for detection and correction of field drifts and head motion. Fourth, ramp sampling is used in the readout direction (denoted as $k_x$) to increase k-space coverage, while maintaining the desired echo spacing and spectral bandwidth (BW) for MRSI given the practical ADC and gradient limits. Fifth, a sparse sampling scheme is used to increase k-space coverage along the phase encoding directions (i.e., $k_y$, $k_z$). More specifically, a dual density sparse sampling scheme is used with a fully sampled region (denoted as $\Omega_1$) around k-space center and an undersampled region (denoted as $\Omega_2$) in outer k-space. These sampling strategies with the (k, t)-space trajectories are aimed at achieving enough spatial resolution for QSM while maintaining a sufficient number of spatiospectral encodings (with a large fully sampled central k-space) to ensure SNR for metabolic imaging. In short, the data acquisition scheme of this embodiment has two distinct features as compared to conventional QSM and MRSI data acquisitions: (1) it uses ultrashort TE/short TR with no water and lipid suppression, larger k-space coverage, larger echo spacing, and fewer echoes (spectral encodings) compared with conventional EPSI acquisitions, and (2) it has a much longer echo train (i.e., more encodings for susceptibility changes) but smaller k-space coverage as compared with conventional GRE-based multiecho QSM acquisitions. Preliminary implementation of these data acquisition features has enabled QSM at a nominal in-plane resolution of 1.8×1.8 mm$^2$ and a through-plane resolution of 2.4 mm, and metabolic imaging at a 2.4×2.4×2.4 mm$^3$ nominal min. resolution in ~7 min. Further improvement of the data acquisition scheme and its implementation can result in better spatial resolutions and shorter data acquisition times.

With reference now to Data Processing according to an embodiment, the (k,t)-space measurements over $\Omega_1$, and $\Omega_2$ using the data acquisition can be expressed as:

$$d_l(k,t_n) = \int s_l(r)\rho(r,f)e^{-i2\pi\Delta f(r)t_n}e^{-i2\pi kr}e^{-i2\pi f t_n}dfdr + \eta_l(k,t_n),$$
$$n=1,2,\ldots,N_E,$$ [Equation 1B]

where $\rho(r,f)$ denotes the spatiospectral distribution of all the molecular components (e.g., water, lipids, metabolites, etc.), $s_l(r)$ the sensitivity map of the 1-th channel, $\{t_n\}$ the echo times, $N_E$ the total number of echoes (i.e., number of time points or spectral encodings for each k-space location), and $\Delta f(r)$ the field inhomogeneity containing the susceptibility information. The vector $r=(x,y,z)$ is used to denote the spatial coordinates and $k=(k_x,k_y,k_z)$ is used to represent the sampled k-space locations. The measurement noise $\eta_l(k,t_n)$ is assumed to be complex white Gaussian. There are three key data processing problems in deriving the susceptibility and metabolite maps from the measured data: (1) reconstruction of the spatiospectral/spatiotemporal function from the sparsely sampled (k,t)-space data, (2) estimation of the susceptibility maps from the reconstructed spectroscopic signals, and (3) reconstruction of the metabolite signals. A brief description of various solutions to these problems follows in the subsequent sections.

Reference will now be made to Interpolation of Sparse (k,t)-Space Data. With a data acquisition scheme according to an embodiment, the MRSI data are measured over a set of (k, t)-space points, divided into two disjoint sets $\Omega_1$ and $\Omega_2$, one for the fully covered central k-space and the other for undersampled outer k-space respectively, and the time axis was slightly undersampled (with respect to the proton spectral BW). Temporal undersampling is not an issue for QSM because it is dependent on the water signals only; for metabolic imaging, temporal undersampling is taken care of in SPICE by using a subspace model (25B,26B). Further discussion of this issue will not be made here. To address the issue of sparse sampling in k-space, multichannel sensitivity encoding is used. More specifically, the (k, t)-space signals are interpolated along the $k_y$ and $k_z$ axes (i.e., the phase encoding directions along which sparse sampling is used) using a hybrid GRAPPA/SENSE method that exploits the special sampling pattern used. More specifically, a set of GRAPPA kernels $\{H_n\}$ are first determined from the k-space samples for $k \in \Omega_1$, for the "early" echoes (e.g., echo times $t_n$ for n=1, 2, . . . , 32; ~60 ms for an echo spacing of 1.78 ms). A simple sliding-window scheme is used to make use of the data from adjacent echoes to improve the estimation of $\{H_n\}$ (i.e., using $d_l(k,t_n)$ for $k \in \Omega_1$, and n=m-2, m-1, m, m+1, m+2 to estimate $H_m$). After the $\{H_n\}$ are determined, GRAPPA interpolation is applied to generate the missing data in $\Omega_2$ for n=1, 2, . . . , 32. These interpolated k-space data are then Fourier reconstructed for each echo time $t_n$ and each receiver channel. These reconstructions are then processed using an SVD-based scheme to extract the coil sensitivity maps $s_l(r)$, assuming that $s_l(r)$ is independent of the echo time $t_n$ (27B). After the $s_l(r)$ are known, SENSE reconstruction is applied to the original undersampled data $(d_l(k,t_n)$ for n=1, 2, . . . , $N_E$). Because the SENSE reconstructions with spatial regularization may not be data-consistent, data consistency is re-enforced by using the SENSE reconstructions and the coil sensitivity maps $s_l(r)$ to generate the missing data in $\Omega_2$ so that k-space is covered at the Nyquist rate with both measured and generated data for each time point. This hybrid GRAPPA/SENSE interpolation scheme seems to work better than GRAPPA interpolation especially for the late noisy echoes. However, a full analysis of its performance is needed, which is beyond the scope of the discussion herein.

With reference now to Quantitative Susceptibility Mapping, the interpolated SPICE (k,t)-space data can be Fourier transformed for each TE to give a sequence of images from which quantitative susceptibility information can be extracted. For clarity, in connection with this embodiment, these are called SPICE images and the method to derive the QSM from them SPICY-QSM. Note that the SPICE data contain signals from water, lipids, and metabolites but the metabolite signals are negligible as far as QSM is concerned, because the unsuppressed water and lipid signals are 3-4 orders of magnitude stronger. Therefore, for QSM calculations, the SPICE images are expressed as $$\rho(r;t_n) = [\rho_w(r) + \rho_l(r)\phi_l(r;t_n)]e^{-t_n^*T^*_2(r)}e^{-i2\pi\Delta f(r)t_n},$$
$$n=1,2,\ldots,N_E$$ [Equation 2B]

where $\rho_w(r)$ and $\rho_l(r)$ denote the proton density of water and lipids (with $T_1$-weighting) respectively, $\phi_l(r, t_n) = \Sigma_j\alpha_j(r)e^{-i2\pi f_j t_n}$ the predetermined spectral structures for lipids (with $\alpha_j$ being relative amplitudes of the lipid peaks), $T^*_2(r)$ the transverse relaxation times, and $\Delta f(r)$ the total frequency offsets because of both the background field inhomogeneity $f_0(r)$ and the tissue susceptibility-induced field inhomogeneity $f_s(r)$. Note that for demonstrating the feasibility of the joint QSM and metabolite mapping technique of this embodiment, healthy subjects were scanned in this work, therefore the lipid component was ignored for the signal model within the brain. Many methods have been proposed for estimating $\Delta f(r)$, extracting $f_s(r)$ from $\Delta f(r)$, and solving the field-to-susceptibility inverse problem (3B,28B). These methods are built upon and take into account specific data acquisition features according to various embodiments to improve the estimation of the susceptibility map, denoted $\chi(r)$ as described below.

First, to take advantage of the larger number of echoes available in SPICE (90-100 vs. 6-8 in conventional QSM), $\Delta f(r)$ is estimated by directly fitting the SPICE images to the complex exponential model in Eq. [2B] using a nonlinear least-squares formulation (29B). This scheme is optimal in the maximum likelihood sense for Gaussian noise and, perhaps even more importantly, it eliminates the need for phase unwrapping used in the conventional linear phase fitting schemes (that can be a difficult problem for low SNR data). Second, SPICE has a relatively smaller k-space coverage than conventional QSM methods. To improve spatial resolution for the susceptibility map beyond the k-space coverage, the susceptibility estimation is constrained using high-resolution anatomical constraints (3B). These constraints can be obtained from the high-resolution anatomical scans typically acquired in standard neuroimaging protocols (e.g., MPRAGE scans). More specifically, the following regularized dipole inversion is solved (3B):

$$\hat{\chi} = \underset{\chi}{\mathrm{argmin}} \|M_{hr}G_\chi\|_1 \text{ s.t. } \|W(D_\chi - f_s)\|_2^2 \le \varepsilon, \quad \text{[Equation 3B]}$$

where $M_{hr}$ contains edge weights obtained from a high resolution anatomical image, G is the gradient operator, $\chi$ the vector representation of the desired tissue susceptibility, and D is the matrix operator for the physical dipole convolution model. W contains weighting coefficients used to account for noise variation in the tissue field $f_s$ as is done in (3B), and $\varepsilon$ is proportional to the noise level. The associated optimization problem is solved using a fixed point algorithm (3B)

Figure 8:
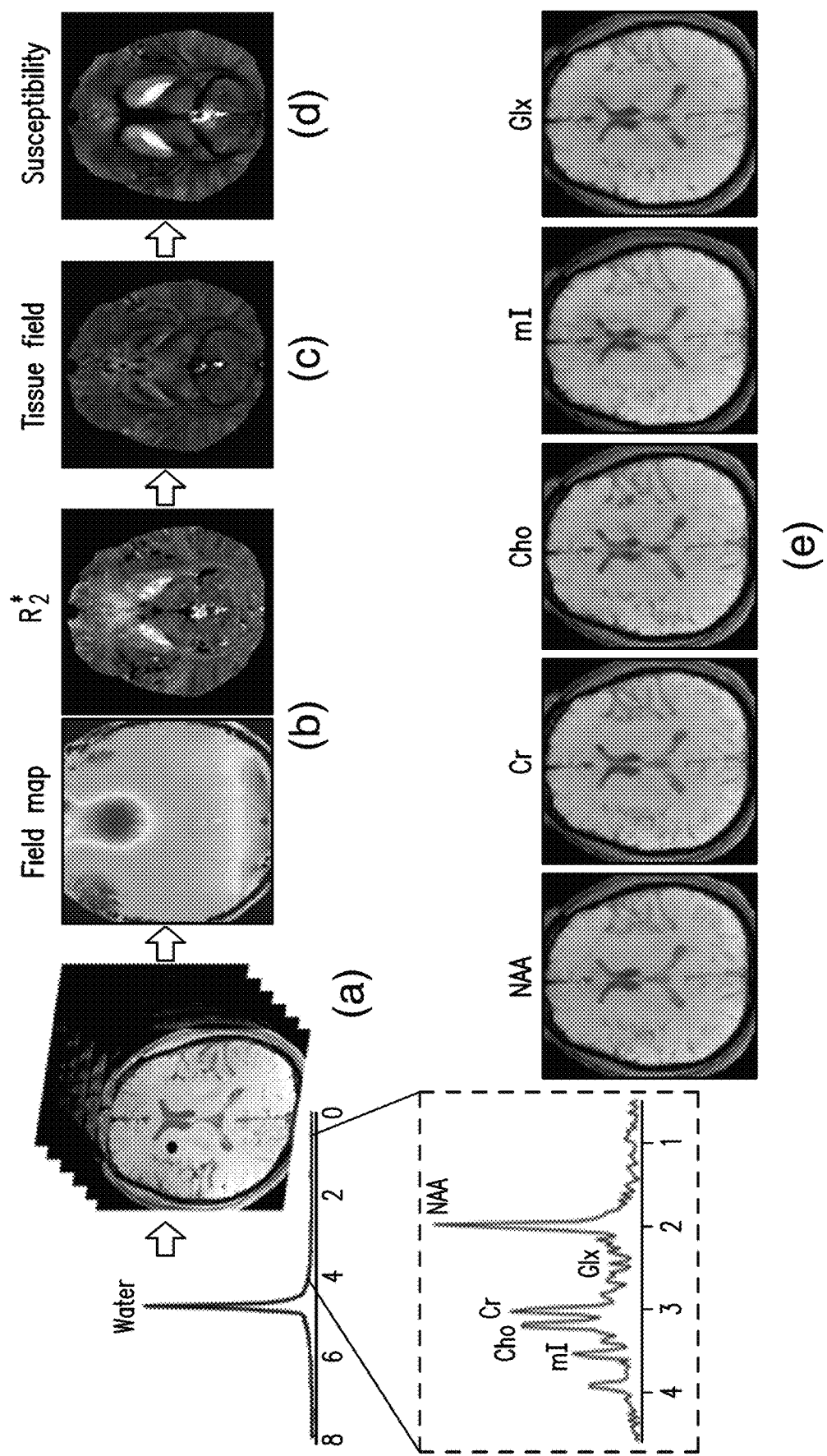
FIG. 8 shows illustration of an embodiment for simultaneous QSM and metabolic imaging using $^1$H-MRSI signals enabled by the invention, and the relevant data processing steps.

The overall data processing scheme for SPICY-QSM according to an embodiment is illustrated in FIG. 8. More specifically, after $\Delta f$ (total field inhomogeneity) is determined (portion (b) of FIG. 8), the background field (because of imperfect shimming and susceptibility sources outside the region of interest such as air-tissue interface) is removed by solving a Laplacian boundary value problem (28B), producing the tissue field $f_s(r)$ (portion (c) of FIG. 8). Finally, tissue susceptibility (portion (d) of FIG. 8) is reconstructed by solving the problem in Eq. [3B].

Reference will now be made to Reconstruction of the Metabolite Spatiospectral Functions. Determination of the metabolite spatiospectral functions from the measured data can be done using the SPICE method for metabolic imaging (25B,26B). More specifically, a union-of-subspaces model is used to represent the spatiotemporal function $\rho(r,t)$ in Eq. [1B] as:

$$\rho(r, t) = \rho_m(r, t) + \rho_w(r, t) + \rho_f(r, t) + \rho_{MM}(r, t) \quad \text{[Equation 4B]}$$

$$= \sum_{p_m=1}^{R_m} u_{p_m}(r)v_{p_m}(t) + \sum_{p_w=1}^{R_w} u_{p_w}(r)v_{p_w}(t) +$$

$$\sum_{p_f=1}^{R_f} u_{p_f}(r)v_{p_f}(t) + \sum_{p_{MM}=1}^{R_{MM}} u_{p_{MM}}(r)v_{p_{MM}}(t),$$

where $\rho_m(r,t)$, $\rho_w(r,t)$, $\rho_f(r,t)$, $\rho_{MM}(r,t)$ denote the signals of metabolites, water, lipids, and macromolecules, respectively. This model assumes that each of the signal components resides in a low-dimensional subspace spanned by the bases $\{V_{p*}(t)\}$ with spatial coefficients $\{U_{p*}(r)\}$, where "m", "MM", "w", "f", respectively. The subspace model significantly reduces the degrees of freedom of the spatiotemporal function. Separating the dominating water/lipid signals (after QSM) from the metabolite signals is done using a method similar to the one in (30B). After water/lipid removal, the metabolite signals are reconstructed from the noisy residuals by solving the following optimization problem:

$$\{\hat{U}_m, \hat{U}_{MM}\} = \quad \text{[Equation 5B]}$$

$$\underset{U_m, U_{MM}}{\arg\min} \|d_{rm} - \Omega\{FB \odot (U_m V_m + U_{MM} V_{MM})\}\|_2^2 +$$

$$\lambda_1 \Psi_1(U_m) + \lambda_2 \Psi_2(U_{MM}),$$

where $d_{rm}$ is a vector containing the nuisance-removed (k,t)-space data, $\Omega$ is the sampling operator, F is the Fourier encoding operator, and B models the field inhomogeneity-related phase terms (estimated from the companion water signals as described in QSM estimation). $V_m$ and $V_{MM}$ are matrix representations of the metabolite and macromolecule bases, both predetermined from training data (25B,26B). $\Psi_1$ and $\Psi_2$ are regularization functionals for metabolite and macromolecule components, respectively. In this work, $\Psi_1$ imposes edge-weighted spatial regularization, and $\Psi_2$ is simply an $I_2$ penalty to improve conditioning. Solution of the problem in Eq. [5B] has been discussed in (26B).

Reference will now be made to certain In Vivo Experiments. Proton MRSI data without water suppression were collected using the SPICE sequence (FIG. 9) from healthy volunteers on a 3T Siemens scanner with IRB approval using a 20-channel head-neck coil. Two outer volume suppression bands (head-to-foot direction) were used to eliminate signal contamination from voxels outside the imaging volume. Other data acquisition parameters are: TR=210 ms, TE=3 ms, flip angle=31°, number of spectral encodings=92, echo spacing=1.78 ms, BW=167 kHz, field of view=230×230×72 mm$^3$, and matrix size=124×128×30 ($k_x$, $k_y$, $k_z$). The center $k_y \times k_z$ (36×30) space was fully sampled, whereas the outer region along $k_y$ is undersampled by a factor of 2, therefore leading to a 7-min scan (corresponding to an "effective" acceleration factor of 1.9 with elliptical sampling). Ramp sampling enabled a 13% resolution gain along the frequency encoding direction. To validate the susceptibility values generated from the method, a corresponding 3D multi-echo GRE acquisition with flow compensation in both the slice and readout directions was carried out over the same volume and field of view with a matrix size of 256×256×30 (spatial resolution=0.9×0.9×2.4 mm$^3$, flip angle 20°, TR=50 ms, TE=4.55 ms, echo spacing=3.65 ms, number of echoes=8, BW/pixel=700 Hz). The same outer volume saturation bands were used for consistency. The Laplacian boundary method (28B) and MEDI (3B) were used to generate the QSM maps from the GRE data. To compare the QSM results from both the SPICE and GRE data sets, anatomical images obtained from experiments were registered using an affine transformation with 12 degrees of freedom in the FMRIB Software Library (31B). The coordinate transformation parameters were then used to align the susceptibility maps estimated from both data sets. To ensure similar regularization effects on solving the field-to-susceptibility inverse problem, the images from both the SPICE and GRE data were scaled to have the same noise level so that an identical regularization parameter can be used.

Figure 11:
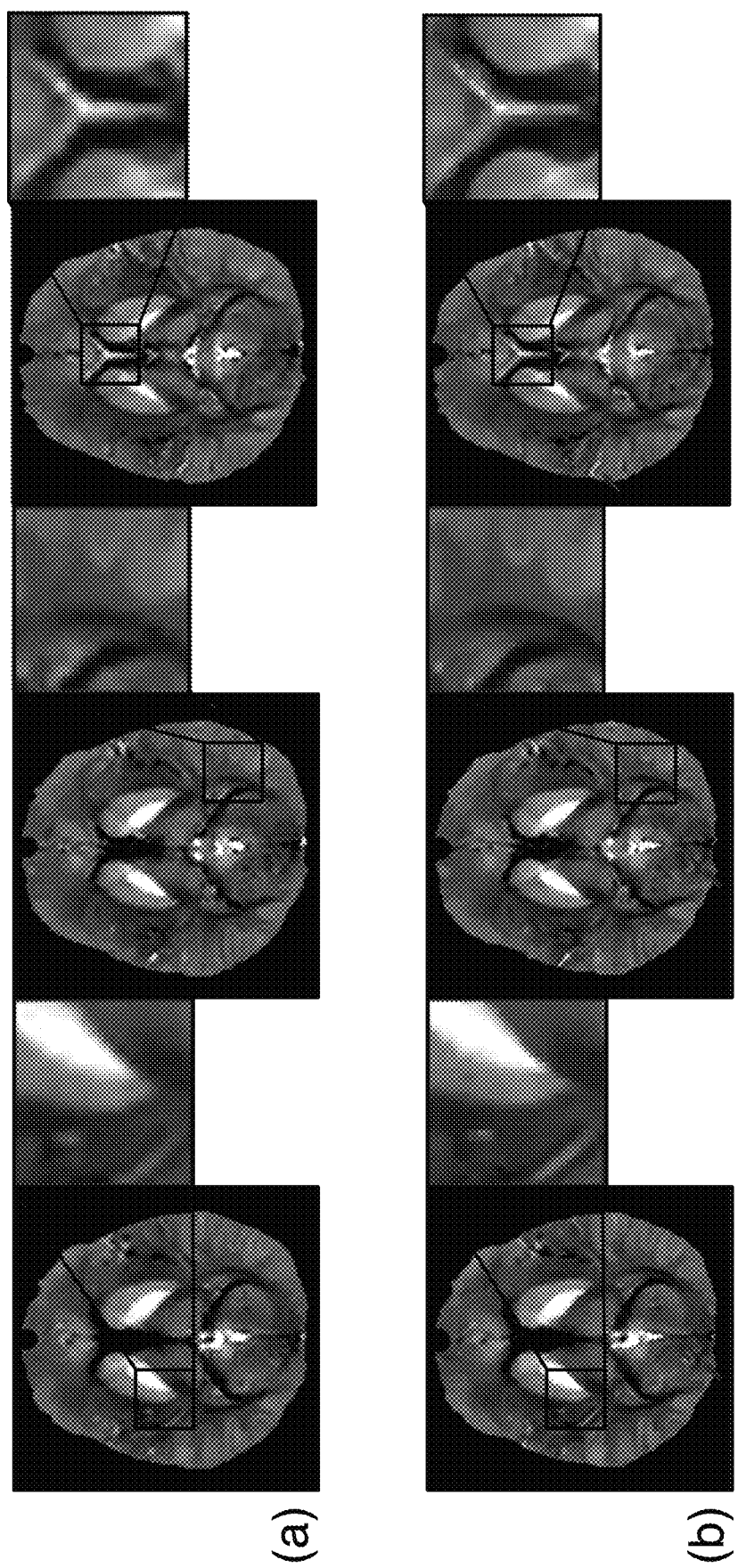
FIG. 11 shows tissue susceptibility estimated from the SPICE data for three consecutive slices using dipole inversion with [see portion (a) of FIG. 11] edge weights derived from the magnitude images of the MRSI data itself, and [see portion (b) of FIG. 11] edge weights derived from a high-resolution anatomical MPRAGE scan. Improved delineation of the subcortical GM regions and finer structures (indicated by red arrows) can be observed in the susceptibility maps generated by the scheme of portion (b).

Reference will now be made to certain results. FIG. 10 shows a set of representative QSM results from in vivo data. The effects of the number of echoes for the processing method according to an embodiment are also shown, in comparison with the results produced by the conventional QSM processing method (i.e., phase unwrapping followed by linear phase fitting). As can be seen, the field maps estimated using complex exponential fitting improve as the number of echoes increases (see the areas highlighted by arrows). Note also that the linear phase method yielded some "bad" fitting points (red arrows in portion (b) of FIG. 10) in regions with large field inhomogeneity, especially when a large number of echoes was used (because of unreliable phase unwrapping for noisy data at long echo times). The errors at these locations were carried over to the subsequently estimated tissue fields and susceptibility maps. Furthermore, with more echoes, ringing artifacts caused by low spatial resolution were reduced in the tissue field and susceptibility maps because of the physical constraints from the complex signal model and the dipole model. An improvement in SNR and a clearer delineation of the gray matter and white matter can also be observed with more echoes (highlighted by the white arrows in portion (a) of FIG. 10). The effects of using high-resolution anatomical information to constrain the dipole inversion is demonstrated in FIG. 11. As can be seen, compared to the susceptibility maps from the SPICE data produced using edge information from the SPICE data itself (portion (a) of FIG. 11), those produced by using edge information from high-resolution MPRAGE images (portion (b) of FIG. 11) exhibit improved delineation of subcortical GM regions (e.g., the transition between globus pallidus and putamen, boundaries between the caudate heads and the ventricles) and better definition of finer structures (as indicated by red arrows).

FIG. 12 shows a set of representatives and susceptibility maps for three slices obtained from both the GRE and SPICE data. The anatomical images (not shown here) from the two scans exhibit slightly different $T_1$ contrast because of the different TRs and flip angles used. The $R^*_2$. and susceptibility maps show very similar iron content-dependent tissue contrast. Although the GRE data have higher spatial resolution, the $R^*_2$ and susceptibility maps produced by the method of an embodiment show better SNR (especially for the $R^*_2$ map) because of the larger number of echoes collected and the lower resolution. Note the susceptibility maps from both the GRE and SPICE scans are able to clearly resolve the major subcortical structures (e.g., globus pallidus [GP], caudate nucleus [CN], and putamen [PU]).

Figure 13:
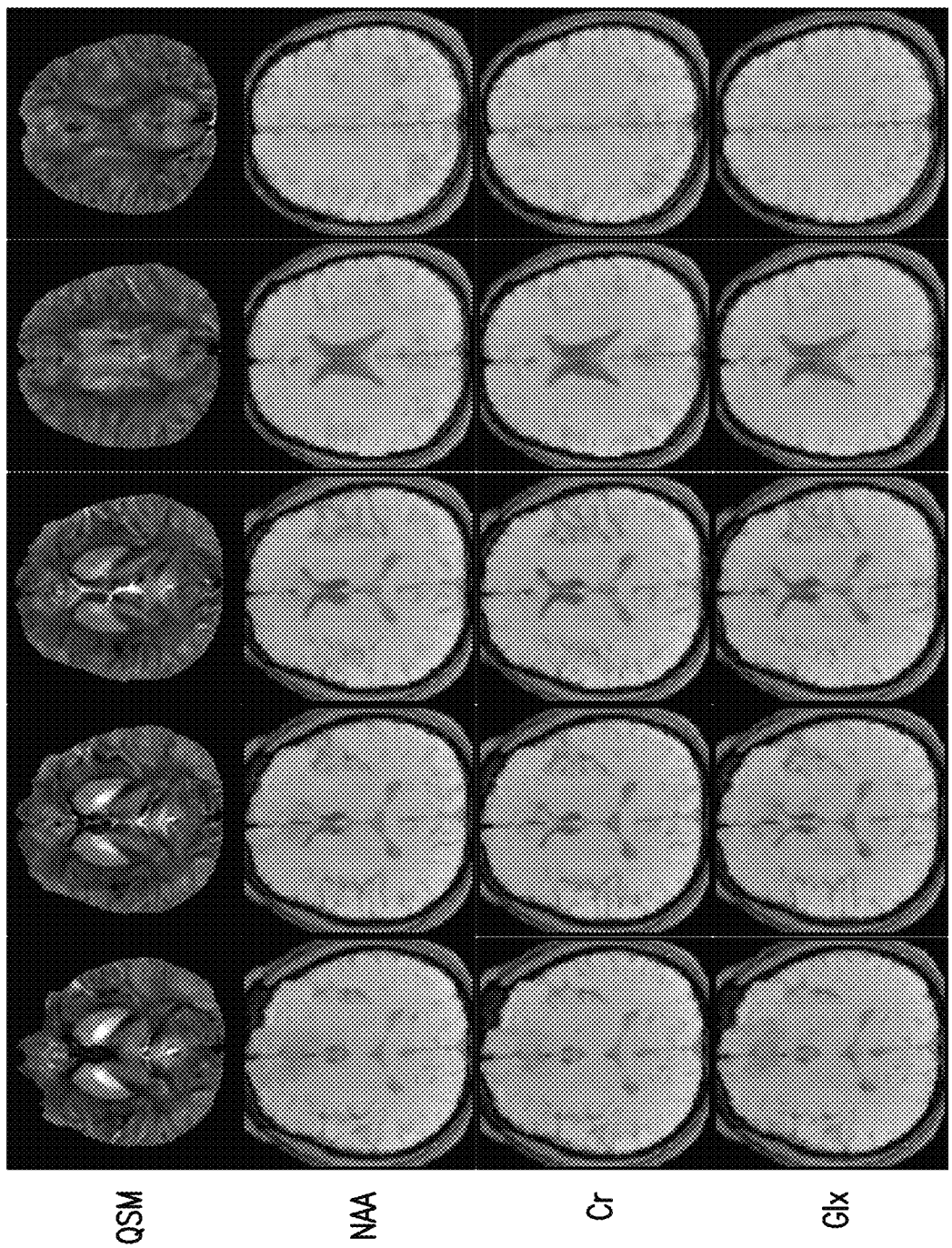
FIG. 13 shows quantitative susceptibility and metabolite maps for five representative slices across the brain obtained from a single 7-min SPICE acquisition. From top to bottom they are: susceptibility maps, NAA, Cr, and Glx maps, respectively. The metabolite maps are normalized individually and shown in color overlaid on the anatomical images.
Figure 14:
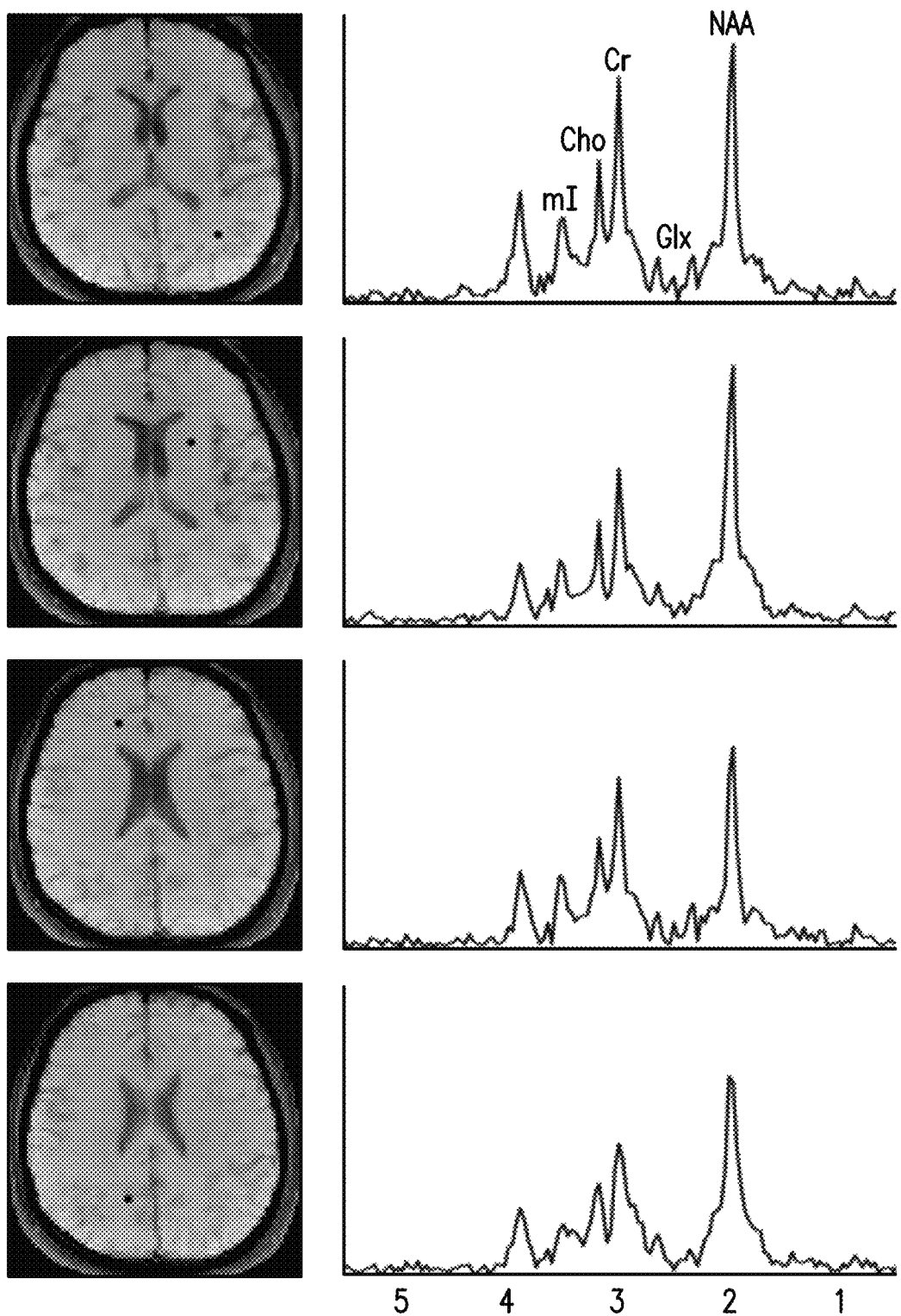
FIG. 14 shows localized spectra from four representative voxels (marked by reddots on the NAA maps on the left) obtained from the same data used to generate FIG. 13. The spectral SNR of the NAA peaks are 78.1, 78.4, 61.0, and 63.6, respectively. Note that the spectral resolution is determined by the spectral subspace rather than the echo spacing in SPICE data.

The susceptibility and metabolite maps (e.g., NAA, creatine [Cr], and glutamate þ glutamine [Glx]) at five different slices across the 3D volume, obtained from a 7-min SPICE scan, are shown in FIG. 13. Spatially resolved metabolite spectra with a spectral resolution of 0.038 ppm (or 4.68 Hz at 3T) from four representative voxels are shown in FIG. 14. The SNRs defined as the ratio between the spectral peaks and the noise standard deviation in the frequency domain for the NAA components at these voxels are 78.1, 78.4, 61.0, and 63.6, respectively. As can be seen, high-SNR metabolite spatiospectral distributions can be produced.

Reference will now be made to a discussion of various embodiments. As described herein, the feasibility has been demonstrated of SPICE for simultaneous mapping of brain tissue susceptibility (directly related to iron deposition [35B]) and metabolites using a single $^1$H-MRSI scan. The $R^*_2$ map, another useful biomarker for iron deposition in the brain (7B), can also be derived from the data acquisition according to an embodiment as shown in FIG. 12. The unique data acquisition features of SPICE (i.e., long echo train for metabolite mapping) were exploited for QSM (e.g., eliminating the need for phase unwrapping used in conventional QSM methods).Specifically, acquiring more echoes helped reduce the errors in the estimated tissue field significantly, therefore reducing the potential error propagation from the estimated tissue field to the final susceptibility reconstruction. Moreover, the acquisition of many echoes is also expected to be beneficial when complex signal models are used to account for nonlinear phase variations such as those described in (36B,37B).

To generate a sufficient number of spectral encodings for metabolite mapping, the SPICE acquisition uses longer TR than standard QSM therefore covering a smaller region of k-space given the same acquisition time. This issue was addressed in this work by a combination of the dipole convolution physical model and the use of morphological information from high-resolution anatomical images (e.g., MPRAGE scan). This allowed improvement of the spatial resolution beyond what was offered by the nominal k-space coverage (~~1.8×1.8×2.4 mm$^3$) of SPICE data. Preliminary results show a clear delineation of iron-rich subcortical GM structures (e.g., GP, CN, and PU) that possess super-intensive bulk susceptibility, which are consistent with the existing QSM data (25B,26B). It is worth noting that acquisition according to an embodiment can also achieve higher resolution for QSM at the expense of longer acquisition time. Note that because of the multiple nonlinear processing steps involved, a full characterization of the SNR and resolution of the final QSM maps is challenging.

Several aspects of the acquisition and processing methods of various embodiments can be further improved. For example, parallel imaging can be better integrated into the data acquisition and processing schemes to enhance resolution and/or data acquisition speed. For example, a better sparse sampling pattern design for the outer k-space region combined with more advanced reconstruction methods can enable larger acceleration factors. Methods taking advantage of the sparse and low-rank structures present in the desired spatiotemporal distributions can be explored to improve the reconstruction of the SPICE images used for QSM processing. The coil sensitivities are currently estimated from the EPSI data itself in this work. However, the methods described herein do not prevent the use of sensitivity determined from auxiliary high-resolution anatomical scans as long as data registration is properly done.

An embodiment of the method uses the MPRAGE data to extract the edge weights used in solving the problem in Eq. [3B]. Other high resolution scans or even a pre-determined high-resolution atlas with different contrast (such as $T^*_2$-weighting) can also be used. Furthermore, enforcing the edge prior through the weighted $L_1$ regularization has been shown to tolerate edge mismatch between anatomical images and susceptibility maps (3B). Sparsity-promoting regularizations other than weighted $L_1$ or $L_2$ can also be used (38B). The intra-volume flow has been shown to have an effect on the QSM results. Flow compensation using first-order moment nulling gradients, as described in (37B), can be included into the SPICE acquisition to address this issue (i.e., before the spatiospectral encoding echo trains and during the even echoes). This would lead to slightly longer echo times and reduce the number of echoes available for spatiospectral reconstruction. These tradeoffs should be considered in the context of particular applications.

As described herein, the feasibility of simultaneous QSM and metabolic imaging of the brain using SPICE has been demonstrated. An embodiment of the data acquisition scheme is built on the SPICE sequence, integrating ultra-short TE/short TR acquisitions with no water suppression and sparse sampling. An embodiment of the processing scheme uses model-based processing to obtain both the susceptibility and metabolite maps. This new imaging capability, when fully developed, may prove useful for a wide range of applications including the study of brain metabolism and neurodegenerative diseases.

References 1B-38B

1B. Wang Y, Liu T. Quantitative susceptibility mapping (QSM): decoding MRI data for a tissue magnetic biomarker. Magn Reson Med 2015; 73: 82-101.
2B. Liu T, Wisnieff C, Lou M, Chen W, Spincemaille P, Wang Y. Nonlinear formulation of the magnetic field to source relationship for robust quantitative susceptibility mapping. Magn Reson Med 2013; 69:467-476.
3B. Liu J, Liu T, de Rochefort L, et al. Morphology enabled dipole inversion for quantitative susceptibility mapping using structural consistency between the magnitude image and the susceptibility map. Neuroimage 2012; 59:2560-2568.
4B. Xu B, Liu T, Spincemaille P, Prince M, Wang Y. Flow compensated quantitative susceptibility mapping for venous oxygenation imaging. Magn Reson Med 2014; 72:438-445.
5B. Haacke E M, Tang J, Neelavalli J, Cheng Y C N. Susceptibility mapping as a means to visualize veins and quantify oxygen saturation. J Magn Reson Imaging 2010; 32:663-676.
6B. Fan A P, Bilgic B, Gagnon L, Witzel T, Bhat H, Rosen B R, Adalsteinsson E. Quantitative oxygenation venography from MRI phase. Magn Reson Med 2014; 72:149-159.
7B. Barbosa J H, Santos A C, Tumas V, Liu M, Zheng W, Haacke E M, Salmon C E. Quantifying brain iron deposition in patients with Parkinson's disease using quantitative susceptibility mapping, R2 and Magn Reson Imaging 2015; 33:559-565.
8B. de Graaf R A. In vivo NMR spectroscopy: principles and techniques. 2nd Edition. New York: John Wiley & Sons; 2007.
9B. Davison J E, Davies N P, Wilson M, Sun Y, Chakrapani A, McKiernan P J, Walter J H, Gissen P, Peet A C. MR spectroscopy-based brain metabolite profiling in propionic acidaemia: metabolic changes in the basal ganglia during acute decompensation and effect of liver transplantation. Orphanet J Rare Dis 2011; 6:19.
10B. Oz G, Alger J R, Barker P B, et al. Clinical proton MR spectroscopy in central nervous system disorders. Radiology 2014; 270:658-679.
11B. Wilson M, Cummins C L, Macpherson L, Sun Y. Magnetic resonance spectroscopy metabolite profiles predict survival in pediatric brain tumors. Eur J Cancer 2013; 49:457-464.
12B. Preul M C, Caramanos Z, Collins D L, Villemure J G, Leblanc R, Olivier A, Pokrupa R, Arnold D L. Accurate, noninvasive diagnosis of human brain tumors by using proton magnetic resonance spectroscopy. Nat Med 1996; 2:323-325.
13B. Astrakas L G, Zurakowski D, Tzika A A, Zarifi M K, Anthony D C, DeGirolami U, Tarbell N J, Black P M. Noninvasive magnetic resonance spectroscopic imaging biomarkers to predict the clinical grade of pediatric brain tumors. Clin Cancer Res 2004; 10:8220-8228.
14B. Sorensen A G. Magnetic resonance as a cancer imaging biomarker. J Clin Oncol 2006; 24:3274-3281.
15B. Acosta-Cabronero J, Williams G B, Cardenas-Blanco A, Arnold R J, Lupson V, Nestor P J. In vivo quantitative susceptibility mapping (QSM) in Alzheimer's disease. PLoS One 2013; 8:e81093.
16B. Colla M, Ende G, Bohrer M, Deuschle M, Kronenberg G, Henn F, Heuser I. MR spectroscopy in Alzheimer's disease: gender differences in probabilistic learning capacity. Neurobiol Aging 2003; 24:545-552.
17B. Langkammer C, Liu T, Khalil M, Enzinger C, Jehna M, Fuchs S, Fazekas F, Wang Y, Ropele S. Quantitative susceptibility mapping in multiple sclerosis. Radiology 2013; 267:551-559.
18B. Lotfipour A K, Wharton S, Schwarz S T, Gontu V, Sch€afer A, Peters A M, Bowtell R W, Auer D P, Gowland P A, Bajaj N P S. High resolution magnetic susceptibility mapping of the substantia nigra in Parkinson's disease. J Magn Reson Imaging 2012; 35:48-55.
19B. Nelson S J. Assessment of therapeutic response and treatment planning for brain tumors using metabolic and physiological MRI. NMR Biomed 2011; 24:734-749.
20B. Brown T R, Kincaid B M, Ugurbil K. NMR chemical shift imaging in three dimensions. Proc Natl Acad Sci USA 1982; 79:3523-3526.
21B. Langkammer C, Bredies K, Poser B A, Barth M, Reishofer G, Fan A P, Bilgic B, Fazekas F, Mainero C, Ropele S. Fast quantitative susceptibility mapping using 3D EPI and total generalized variation. Neuroimage 2015; 111:622-630.
22B. Cao P, Wu E X. Accelerating phase-encoded proton MR spectroscopic imaging by compressed sensing. J Magn Reson Imaging 2015; 41:487-495.
23B. Sheikh M, Lam F, Ma C, Clifford B, Liang Z P. Rapid, high-resolution 3D $^1$H-MRSI of the brain based on FID acquisitions. In Proceedings of the 24th Annual Meeting of ISMRM, Singapore, 2016. p. 2353.
24B. Lam F, Li Y, Clifford B, Peng X, Liang Z P. Simultaneous mapping of brain metabolites, macromolecules and tissue susceptibility using SPICE. In Proceedings of the 25th Annual Meeting of ISMRM, Honolulu, Hi., USA, 2017. p. 1249.
25B. Lam F, Liang Z P. A subspace approach to high-resolution spectroscopic imaging. Magn Reson Med 2014; 71:1349-1357.
26B. Lam F, Ma C, Clifford B, Johnson C L, Liang Z P. High-resolution $^1$HMRSI of the brain using SPICE: data acquisition and image reconstruction. Magn Reson Med 2015; 76:1059-1070.
27B. Bydder M, Hamilton G, Yokoo T, Sirlin C B. Optimal phased-array combination for spectroscopy. Magn Reson Imaging 2008; 26:847-850.
28B. Zhou D, Liu T, Spincemaille P, Wang Y. Background field removal by solving the Laplacian boundary value problem. NMR Biomed 2014; 27:312-319.
29B. Golub G, Pereyra V. Separable nonlinear least squares: the variable projection method and its applications. Inverse Probl 2013; 19:R1-R26.
30B. Ma C, Lam F, Johnson C L, Liang Z P. Removal of nuisance signals from limited and sparse $^1$H MRSI data using a union-of-subspaces model. Magn Reson Med 2016; 75:488-497.
31B. Jenkinson M, Smith S. A global optimization method for robust affine registration of brain images. Med Image Anal 2001; 5:143-156.
32B. Sun H, Wilman A H. Quantitative susceptibility mapping using single-shot echo-planar imaging. Magn Reson Med 2015; 73:1932-1938.
33B. Sun H, Seres P, Wilman A H. Structural and functional quantitative susceptibility mapping from standard fMRI studies. NMR Biomed 2017. doi: 10.1002/nbm.3619.
34B. Lin P Y, Chao T C, Wu M L. Quantitative susceptibility mapping of human brain at 3T: a multisite reproducibility study. AJNR Am J Neuroradiol 2015; 36:467-474.
35B. Langkammer C, Schweser F, Krebs N, et al. Quantitative susceptibility mapping (QSM) as a means to measure brain iron? A post mortem validation study. Neuroimage 2012; 62:1593-1599.
36B. Dimov A V, Liu T, Spincemaille P, Ecanow J S, Tan H, Edelman R R, Wang Y. Joint estimation of chemical shift and quantitative susceptibility mapping (chemical QSM). Magn Reson Med 2015; 73:2100-2110.

37B. Xu B, Liu T, Spincemaille P, Prince M, Wang Y. Flow compensated quantitative susceptibility mapping for venous oxygenation imaging. Magn Reson Med 2014; 72:438-445.

38B. Langkammer C, Schweser F, Shmueli K, et al. Quantitative susceptibility mapping: report from the 2016 reconstruction challenge. Magn Reson Med 2017. doi: 10.1002/mrm.26830.

Reference will now be made to various embodiments directed to further accelerating SPICE for ultrafast MRSI using learned spectral features. As described herein is a new method to incorporate machine learning into SPICE (SPectroscopic Imaging by exploiting spatiospectral CorrElation) to further enhance its data acquisition speeds. The method of an embodiment exploits the significant amount of prior knowledge about the spectral variations of biological tissues, e.g., molecular composition and resonance structures, by devising a novel strategy to learn the molecule-specific spectral features from training data, and incorporating the learned features into a subspace representation of the desired spatiospectral distribution for a general MRSI study. Impressive results have been produced by the method of an embodiment from $^1$H-MRSI of the brain without any suppression pulses.

As described herein, SPICE (SPectroscopic Imaging by exploiting spatiospectral CorrElation) has emerged as a potentially powerful tool to achieve fast, high-resolution MRSI[1D-3D]. Key steps within the SPICE framework include the determination of low-dimensional subspaces where high-dimensional spectroscopic signals reside and the use of these subspaces for spatiospectral processing. The current approach is to acquire high-SNR navigators during each experiment, and extract a data-dependent subspace[1C,2C] [references 1C-8C below are referred to herein by a number followed by the letter "C", e.g., 1C, 2C, etc.]. Recognizing that a significant amount of prior information is available to capture the spectral variations of biological tissues, presented herein is a new approach to improve SPICE. Specifically, a novel strategy is designed to learn the molecular-dependent spectral features from training data. Using these learned features, the spectral signatures of individual molecules can be pre-determined and integrated into a subspace representation of a general spatiospectral function. The method of this embodiment has been evaluated using $^1$H-MRSI of the brain without water suppression. High-quality spatiospectral reconstructions have been produced without acquiring experiment-dependent navigator data.

Reference will now be made to certain theory & methods. As described herein, SPICE is characterized by the use of a low-dimensional subspace model to represent the high-dimensional spectroscopic data and special acquisition/processing strategies for subspace estimation and subspace-based spatiospectral reconstruction. To determine the metabolite signal subspace, a key step in the SPICE framework, high-SNR, water/lipid-suppressed navigators are typically acquired for each experiment, and used to estimate a data-dependent subspace (e.g., through SVD analysis) for subsequent processing[1C,2C].

With reference now to an improved SPICE with learned spectral features according to an embodiment, presented is a new strategy to improve SPICE-based MRSI by exploiting the significant amount of prior knowledge about the spectral variations of individual molecules. Specifically, the spectroscopic signal at each voxel with M molecules is represented as[4C-7C]

$$s(t) = \sum_{m=1}^{M} c_m \phi_m(t; \alpha_m) e(t), \quad \text{[Equation 1C]}$$

where $c_m$ denotes the concentration of the mth molecule, $\phi_m(t)$ the corresponding spectral structure, and e(t) the experiment-dependent signal distortion (e.g., due to $B_0$ inhomogeneity or eddy current). It is recognized that 1) the functional form of $\phi_m(t; \alpha_m)$ is determined by quantum mechanics and a few molecular-specific parameters in $\alpha_m$ (e.g., relaxation and frequency shifts); 2) the distributions of $\alpha_m$ are typically in a narrow range for biological tissues and can be learned from specifically acquired training data[7C]; 3) once such "empirical" distributions are learned, the resulting spectral variations can be represented by a low-dimensional subspace model, which can then be used to represent a general spatiospectral function of interest.

To learn the empirical distribution of $\alpha_m$, training datasets were acquired from multiple subjects using low-resolution EPSI. Note that other alternatives can be considered to capture pathology-specific spectral features. These data were fitted using the following model (after water/lipids removal and $B_0$ correction):

$$s(r, t) = \sum_{m=1}^{M} c_m(r) \psi_m(t) e^{-t/T^*_{2,m}(r) + i2\pi \delta f_m(r)t} e_1(r, t), \quad \text{[Equation 2C]}$$

where $\psi_m(t)$ denotes the molecular basis, the values in $\alpha_m = \{T^*_{2,m}, \delta f_m\}$ sample the empirical distribution and $e_1(r, t)$ is obtained from non-water-suppressed data (i.e., data for which water was not suppressed during the acquisition). All the fitted spectra were arranged into a Casorati matrix from which a metabolite basis was estimated. In this work, considered were NAA, creatine, choline, glutamate, glutamine, and myo-inositol to demonstrate the feasibility of the approach, while more molecules can be considered.

Given the subspace, spatiospectral reconstruction for a general MRSI study can be obtained using a union-of-subspaces model[1C-3C]. The water/lipid subspace was determined by performing a Lorentzian fitting to a reconstruction from the original MRSI data (dominated by water/lipid signals). A macromolecule subspace was determined using metabolite-nulled data[8C]. The reconstruction was done by a spatially regularized least-squares fitting[3C].

Reference will now be made to certain results and discussion. In vivo data were acquired using an ultrashort-TE SPICE sequence, without water suppression[3C], on a Siemens Prisma 3T scanner with TR/TE=210/4 ms, matrix size=96×96×24, and FOV=240×240×72 mm³ (2.5×2.5×3 mm³ nominal resolution). Data were acquired in 5 min with ×2 undersampling along the phase encoding directions. MPRAGE images were acquired to obtain tissue segmentations for spatiospectral processing[1C,2C]. All training data were acquired with matrix size=16×16×12.

Figure 16:
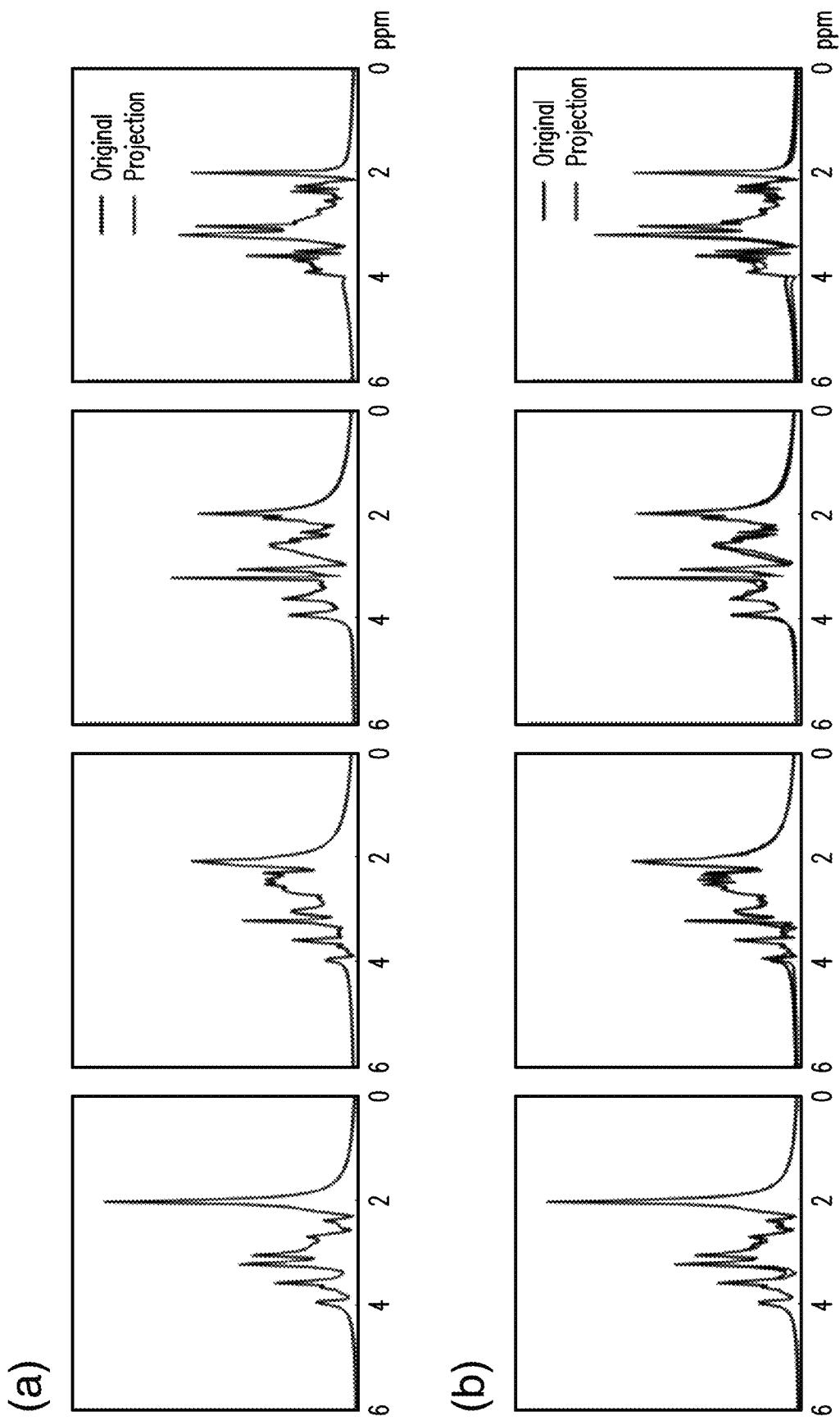
FIG. 16 shows metabolite subspace estimation using learned spectral features. Portion (a) of FIG. 16 shows four dominant spectral basis functions obtained by applying SVD to the fitted spatiospectral distribution for one training data and their projections onto the subspace from another; portion (b) of FIG. 16 shows a similar comparison as in portion (a) but between the subspace from training data and that from 20000 synthesized spectra with uniformly distributed $T_2^*$ and $\delta f$. The subspaces from different training data are very similar (consistent to the $T_2^*$ distributions in FIG. 15), but the subspace from synthesized data can not represent the subspace determined from experimental data well, demonstrating the importance of training data.

FIG. 15 shows the distributions of metabolite $T^*_2$ from three subjects and the singular values for the fitted training data. The rapid decays in portion (a) of FIG. 15 imply that all the spectral functions reside in a low-dimensional subspace. The similar parameter distributions for all subjects support the concept of using training data for subspace estimation. FIG. 16 compares the metabolite bases from different subjects, and the bases from training data to those from synthesized spectra with uniformly distributed $\alpha_m$.

Figure 17:
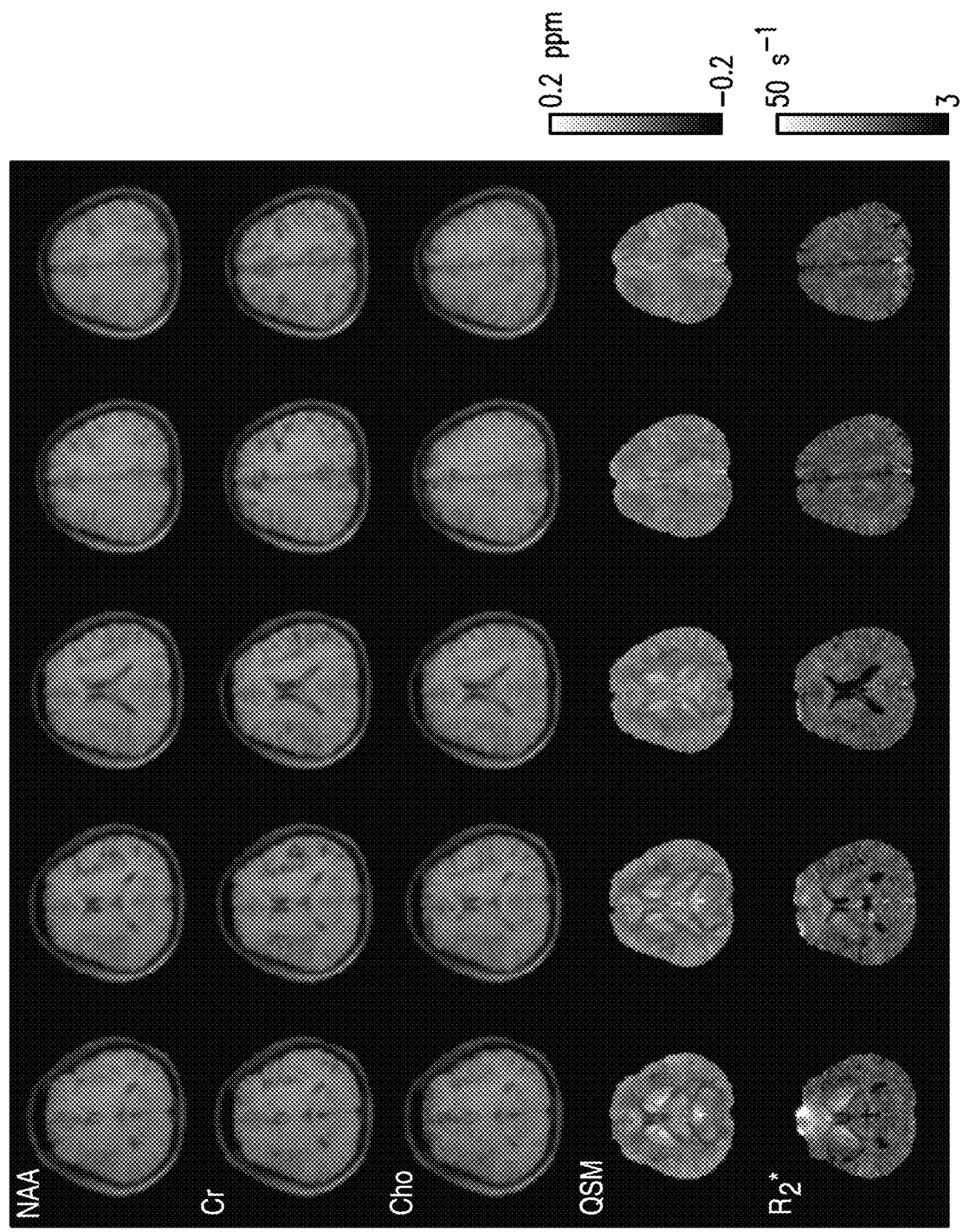
FIG. 17 shows metabolite maps (rows 1-3) obtained by the method of an embodiment from an ultrahigh-resolution, ultrashort-TE $^1$H-MRSI data set (acquired in 5 min with TR/TE=210/4 ms), using the learned metabolite subspace from three subjects. As can be seen, high-SNR, high-resolution metabolite maps were produced (e.g., the clear gray matter/white matter contrast in the Cr maps). QSM and $R_2^*$ maps (rows 4-5) obtained from the unsuppressed water signals are also shown to illustrate joint imaging capability.
Figure 18:
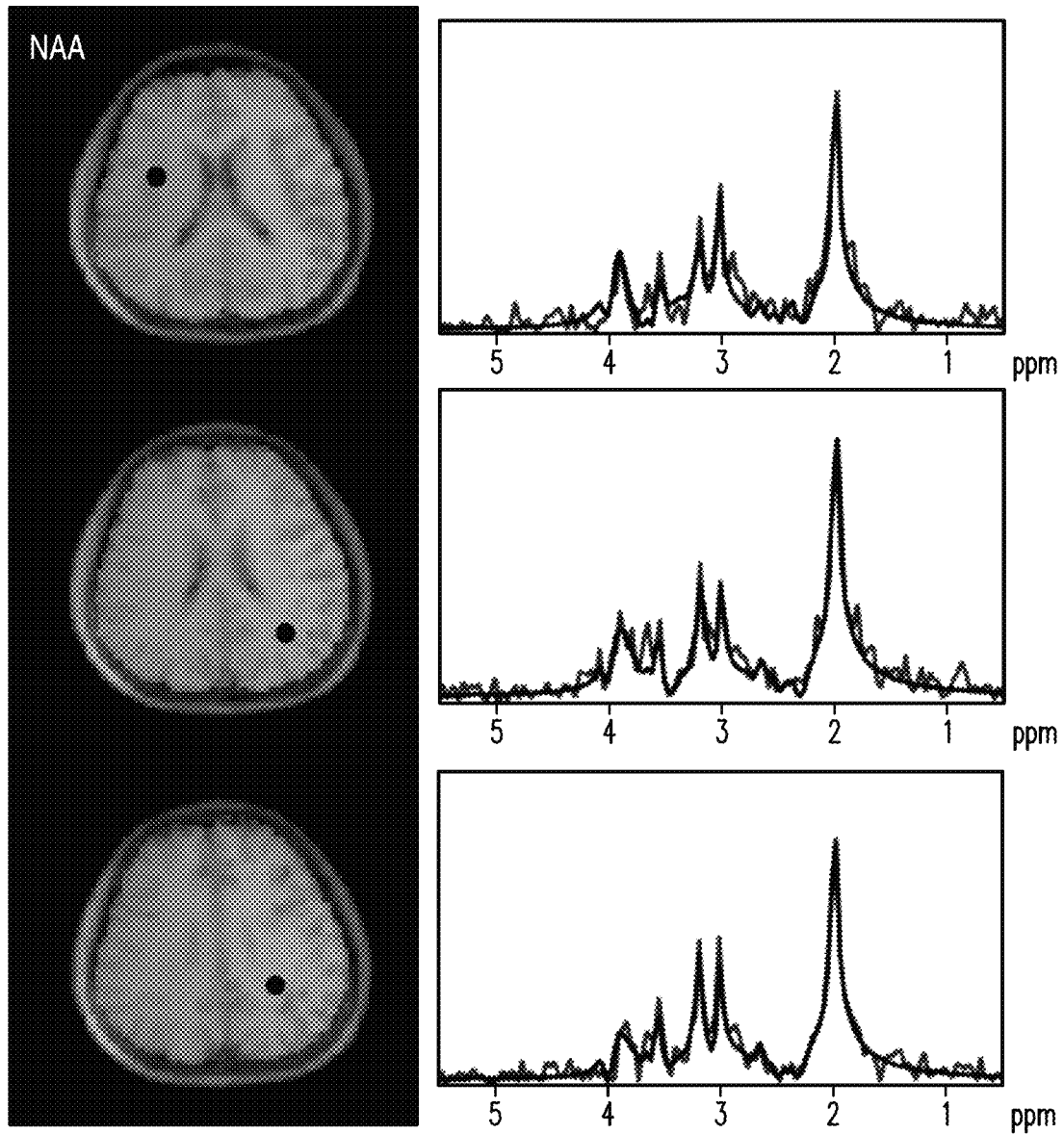
FIG. 18 shows spatially localized spectra from the reconstruction in FIG. 17 (voxel locations indicated by the black dots in the left panel). The spectra in lighter (noisier) lines were produced using a data-dependent metabolite subspace estimated from an extra low-resolution EPSI scan of the same subject (acquired during the same experiment), while the spectra in darker (less noisy) lines were produced using the learned subspace. The clear noise reduction without significant spectral distortion demonstrates the fidelity of the learned subspace.

Consistent subspaces can be observed for different subjects, while the synthesized subspace cannot represent the experimental data accurately, demonstrating the need of training data (determining biologically meaningful parameter distributions). FIGS. 17-18 show the high-quality metabolite spatiospectral reconstructions obtained using the learned subspace. QSM and $R_2^*$ maps from the unsuppressed water signals are also shown.

As described herein is a new approach to improve SPICE, by learning molecular-specific spectral features and incorporating the learned features into a subspace representation of general spatiospectral distributions. Excellent results were produced from volumetric $^1$H-MRSI of the brain without water suppression.

As described herein, in one or more embodiments the training data are acquired with single or multiple TEs.

As described herein, in one or more embodiments an acquisition uses a spatiospectral encoding strategy in which neither water suppression pulses nor lipid suppression pulses are needed.

As described herein, in one or more embodiments the acquisition uses a spatiospectral encoding strategy in which the (k,t)-space is sampled sparsely to generate spatiospectrally encoded data during each short TR period.

References 1C-8C

1C. Lam F et al., High-resolution 1H-MRSI of the brain using SPICE: Data acquisition and image reconstruction, Magn Reson Med, 2016; 76:1059-1070.
2C. Ma C et al., High-resolution 1H-MRSI of the brain using short-TE SPICE, Magn Reson Med, 2017; 77:467-479.
3C. Peng X et al., Simultaneous QSM and metabolic Imaging of the brain using SPICE, Magn Reson Med, 2017, In Press.
4C. Provencher S W, Estimation of metabolite concentrations from localized in vivo proton NMR spectra, Magn Reson Med, 1993; 30:672-679.
5C. Vanhamme L et al., Improved method for accurate and efficient quantification of MRS data with use of prior knowledge, J Magn Reson, 1997; 129:35-43.
6C. Ratiney H et al., Time-domain semi-parametric estimation based on a metabolite basis set, NMR Biomed, 2015; 18:1-13.
7C. Li Y et al., A subspace approach to spectral quantification for MR spectroscopic imaging, IEEE Trans Biomed Eng, 2017; 64:2486-2489.
8C. Lam F et al., Macromolecule mapping of the brain using ultrashort-TE acquisition and reference-based metabolite removal, Magn Reson Med, 2017, In Press.

Figure 19:
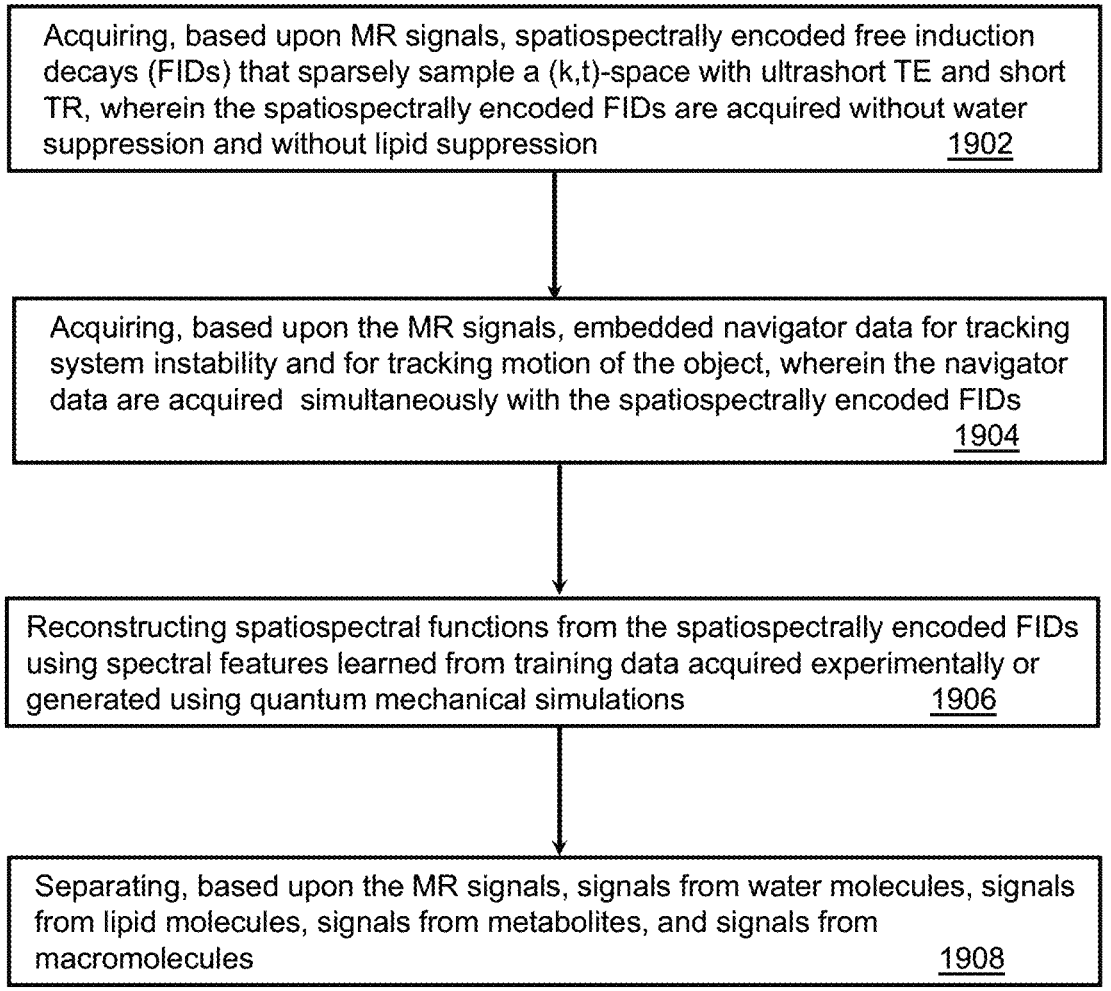
FIG. 19 shows an illustrative method according to an embodiment.

Referring now to FIG. 19, this depicts an illustrative embodiment of a method 1901 in accordance with various aspects described herein. As seen in this FIG. 19, step 1902 comprises acquiring, based upon MR signals, spatiospectrally encoded free induction decays (FIDs) that sparsely sample a (k,t)-space with ultrashort TE and short TR, wherein the spatiospectrally encoded FIDs are acquired without water suppression and without lipid suppression. Next, step 1904 comprises acquiring, based upon the MR signals, embedded navigator data for tracking system instability and for tracking motion of the object, wherein the navigator data are acquired simultaneously with the spatiospectrally encoded FIDs. Next, step 1906 comprises reconstructing spatiospectral functions from the spatiospectrally encoded FIDs using spectral features learned from training data acquired experimentally or generated using quantum mechanical simulations. Next, step 1908 comprises separating, based upon the MR signals, signals from water molecules, signals from lipid molecules, signals from metabolites, and signals from macromolecules. Further, in this method one or more quantitative tissue susceptibility maps, one or more metabolite maps, and one or more macromolecule maps can be obtained from a single MRSI data set that is based upon the MR signals.

While for purposes of simplicity of explanation, the respective processes are shown and described as a series of blocks in FIG. 19, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 20:
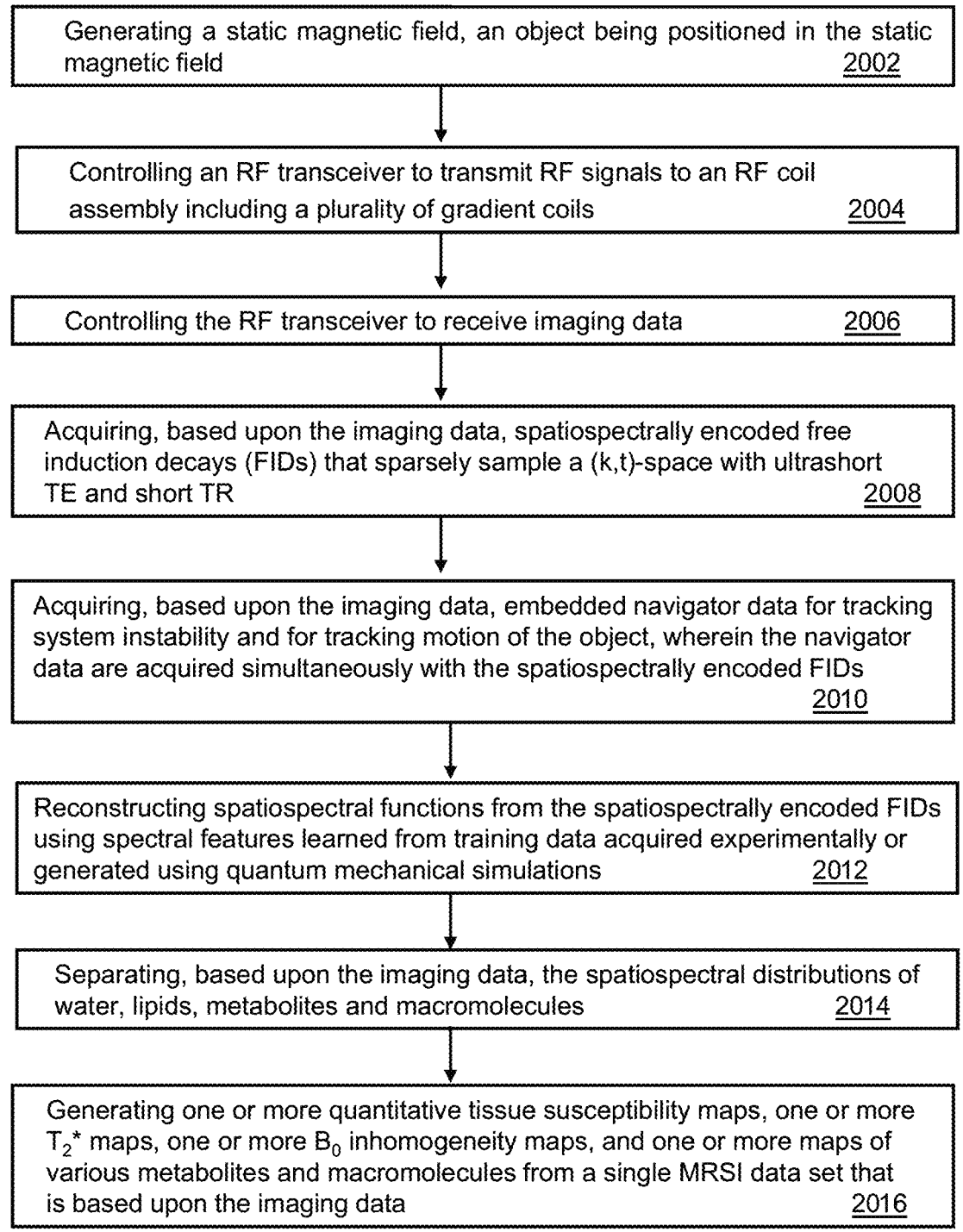
FIG. 20 shows an illustrative method according to an embodiment.

Referring now to FIG. 20, this depicts an illustrative embodiment of a method 2001 in accordance with various aspects described herein. As seen in this FIG. 20, step 2002 comprises generating a static magnetic field, an object being positioned in the static magnetic field. Next, step 2004 comprises controlling an RF transceiver to transmit RF signals to an RF coil assembly including a plurality of gradient coils. Next, step 2006 comprises controlling the RF transceiver to receive imaging data. Next, step 2008 comprises acquiring, based upon the imaging data, spatiospectrally encoded free induction decays (FIDs) that sparsely sample a (k,t)-space with ultrashort TE and short TR. Next, step 2010 comprises acquiring, based upon the imaging data, embedded navigator data for tracking system instability and for tracking motion of the object, wherein the navigator data are acquired simultaneously with the spatiospectrally encoded FIDs. Next, step 2012 comprises reconstructing spatiospectral functions from the spatiospectrally encoded FIDs using spectral features learned from training data acquired experimentally or generated using quantum mechanical simulations. Next, step 2014 comprises separating, based upon the imaging data, spatiospectral distributions of water, lipids, metabolites and macromolecules. Next, step 2016 comprises generating one or more quantitative tissue susceptibility maps, one or more $T_2^*$ maps, one or more $B_0$ inhomogeneity maps, and one or more maps of various metabolites and macromolecules from a single MRSI data set that is based upon the imaging data. Further, the ultrashort TE is less than 4 ms, the short TR is less than 300 ms, and the method does not require a water suppression pulse or a lipid suppression pulse for $^1$H-MRSI.

While for purposes of simplicity of explanation, the respective processes are shown and described as a series of blocks in FIG. 20, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Referring now to FIG. 21, this depicts an illustrative embodiment of a method 2101 in accordance with various aspects described herein. As seen in this FIG. 21, step 2102 comprises acquiring spatiospectrally encoded FID data covering (k, t)-space in variable density with ultrashort-TE and short-TR, without water and lipid suppression, suitable for image reconstruction using a union-of-subspaces model or a linear combination of low-rank matrix/tensor models. Next, step 2104 comprises reconstructing a spatiospectral function from the spatiospectrally encoded FID data that is sparsely sampled using the union-of-subspaces model or the linear combination of low-rank matrix/tensor models. Further, in this method the acquiring of the spatiospectrally encoded FID data is performed utilizing an RF coil assembly including a plurality of gradient coils, and an RF transceiver controlled by a pulse module to transmit RF signals to the RF coil assembly. Further, in this method an ultrashort TE less than 4 ms and a short TR less than 300 ms are utilized and no water suppression pulse is used and no lipid suppression pulse is used.

While for purposes of simplicity of explanation, the respective processes are shown and described as a series of blocks in FIG. 21, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 22:
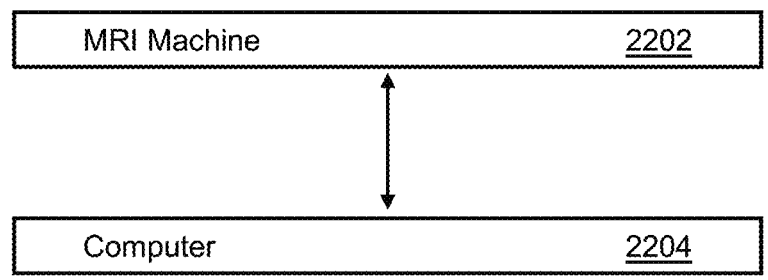
FIG. 22 shows an illustrative diagrammatic representation of a system according to an embodiment.

Referring now to FIG. 22, this depicts an illustrative diagrammatic representation of a system 2201 according to an embodiment. As seen in this FIG. 22, system 2201 includes MRI machine 2202 in operative communication with computer 2204. The MRI machine 2202 can obtain MRI data from a patient (not shown) and can be controlled by and/or provide data to the computer 2204. In one specific example, one or more pulse sequences (such as described herein) can be implemented in MRI machine 2202 and/or computer 2204 by software (and/or by software in combination with firmware/hardware). In one specific example, the MRI machine (which can be referred to as a scanner) comprises several elements: a magnet (usually a superconducting solenoidal magnet) that provides a static magnetic field, as well as gradient coils used to introduce time-varying and spatially-varying magnetic fields. Nuclear Magnetic Resonance active nuclei, such as $^1$H, located in the magnetic field of the main magnet, can be excited by the use of Radio Frequency (RF) transmitters in concert with resonant coils, such as a body coil. These excited nuclei are manipulated via magnetic field gradients induced by the gradient coils and associated hardware to encode imaging data in the nuclear magnetic resonance signals emitted by the object being imaged and sampled by RF receiver hardware in concert with resonant coils. The coordination of RF transmit pulses, magnetic field gradients, and RF receiver sampling are all coordinated by computer systems running a specific program that implements a scheme, called a pulse sequence, to image the object. Once the data is received from the object, using knowledge of the pulse sequence and the received data, the data is reconstructed using Fourier transforms, and other knowledge about the physics of the MR imaging process to generate human readable images. All of this is coordinated via a human interface, often known as a console or host, where users can visualize the results of scans, and prescribe additional scans, often inputting parameters into the pulse sequences to obtain specific types of images.

Figure 23:
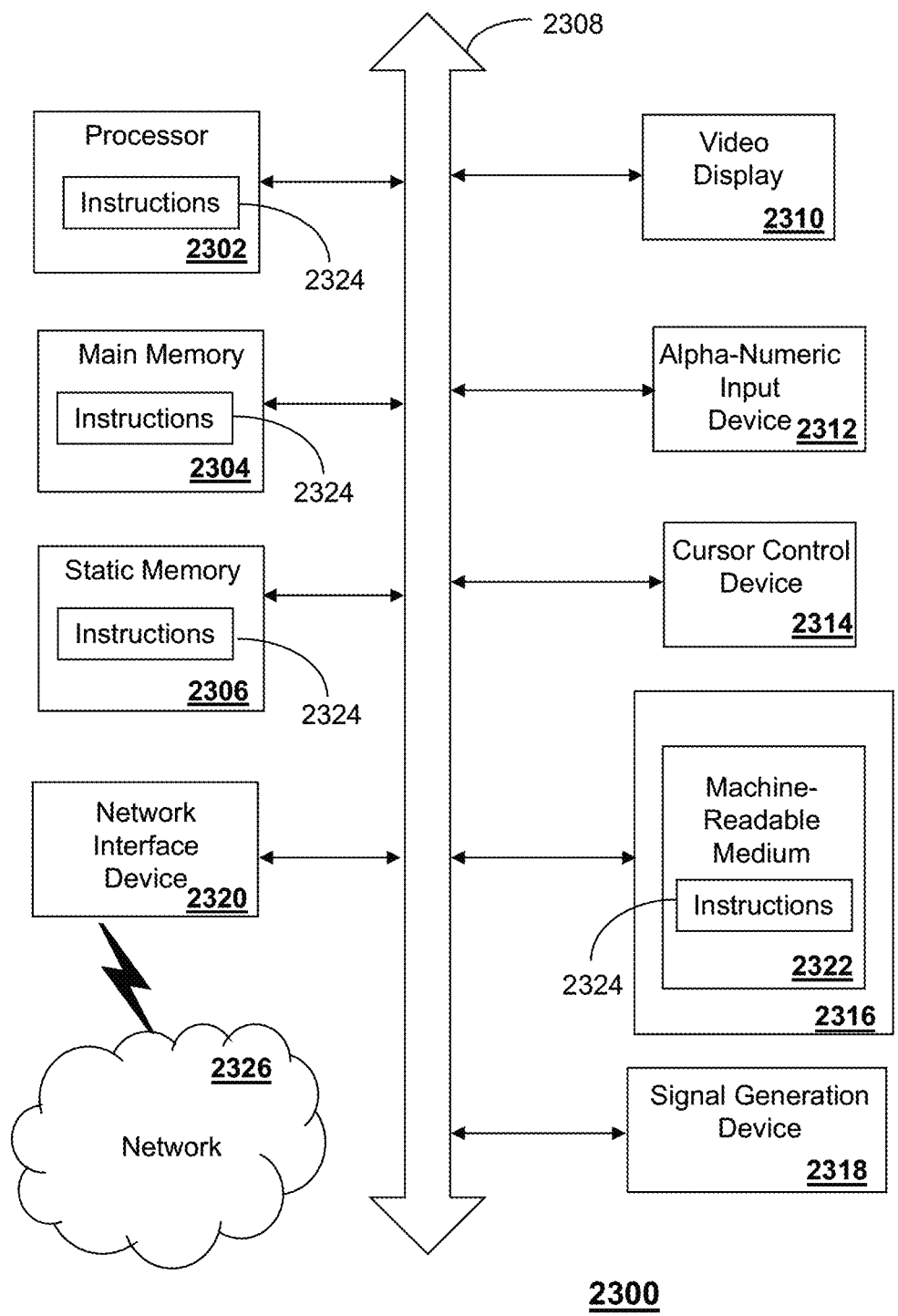
FIG. 23 shows an illustrative diagrammatic representation of a machine in the form of a computer system within which a set of instructions, when executed, may cause the machine to perform any one or more of the methodologies disclosed herein.

Referring now to FIG. 23, this depicts an exemplary diagrammatic representation of a machine in the form of a computer system 2300 within which a set of instructions, when executed, may cause the machine to perform any one or more of the methods discussed above. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 2300 may include a processor 2302 (e.g., a central processing unit (CPU), a graphics processing unit (GPU, or both), a main memory 2304 and a static memory 2306, which communicate with each other via a bus 2308. The computer system 2300 may further include a video display unit 2310 (e.g., a liquid crystal display (LCD), a flat panel, or a solid state display. The computer system 2300 may include an input device 2312 (e.g., a keyboard), a cursor control device 2314 (e.g., a mouse), a disk drive unit 2316, a signal generation device 2318 (e.g., a speaker or remote control) and a network interface device 2320.

The disk drive unit 2316 may include a tangible computer-readable storage medium 2322 on which is stored one or more sets of instructions (e.g., software 2324) embodying any one or more of the methods or functions described herein, including those methods illustrated above. The instructions 2324 may also reside, completely or at least partially, within the main memory 2304, the static memory 2306, and/or within the processor 2302 during execution thereof by the computer system 2300. The main memory 2304 and the processor 2302 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 2322 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to:

solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the discussion herein are intended to be non-limiting, and thus additional numerical values, ranges, and percentages are within the scope of the disclosed embodiments.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable gate array. Furthermore, software implementations (e.g., software programs, instructions, etc.) including, but not limited to, distributed processing or component/object distributed processing, parallel processing, or virtual machine processing can also be constructed to implement the methods described herein. It is further noted that a computing device such as a processor, a controller, a state machine or other suitable device for executing instructions to perform operations or methods may perform such operations directly or indirectly by way of one or more intermediate devices directed by the computing device.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. The exemplary embodiments can include combinations of features and/or steps from multiple embodiments. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

Less than all of the steps or functions described with respect to the exemplary processes or methods can also be performed in one or more of the exemplary embodiments. Further, the use of numerical terms to describe a device, component, step or function, such as first, second, third, and so forth, is not intended to describe an order or function unless expressly stated so. The use of the terms first, second, third and so forth, is generally to distinguish between devices, components, steps or functions unless expressly stated otherwise. Additionally, one or more devices or components described with respect to the exemplary embodiments can facilitate one or more functions, where the facilitating (e.g., facilitating access or facilitating establishing a connection) can include less than every step needed to perform the function or can include all of the steps needed to perform the function.

In one or more embodiments, a processor (which can include a controller or circuit) has been described that performs various functions. It should be understood that the processor can be multiple processors, which can include distributed processors or parallel processors in a single machine or multiple machines. The processor can be used in supporting a virtual processing environment. The virtual processing environment may support one or more virtual machines representing computers, servers, or other computing devices. In such virtual machines, components such as microprocessors and storage devices may be virtualized or logically represented. The processor can include a state machine, application specific integrated circuit, and/or programmable gate array including a Field PGA. In one or more embodiments, when a processor executes instructions to perform "operations", this can include the processor performing the operations directly and/or facilitating, directing, or cooperating with another device or component to perform the operations.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While the disclosure has been described in detail in connection with a limited number of embodiments, it should be readily understood that the invention is not limited to such disclosed embodiments. Rather, that the disclosed embodiments can be modified to incorporate any number of variations, alterations, substitutions or equivalent arrange-

What is claimed is:

1. A device to acquire spatiospectral distributions from an object, the device comprising:
   a magnetic field generator that generates a static magnetic field, the object being positioned in the static magnetic field;
   an RF coil assembly including a plurality of gradient coils;
   an RF transceiver controlled by a pulse module that transmits RF signals to the RF coil assembly and that receives magnetic resonance (MR) signals; and
   a computer which, responsive to executing instructions, performs operations, the operations comprising:
      acquiring, based upon the MR signals, spatiospectrally encoded free induction decays (FIDs) that sparsely sample a (k,t)-space with ultrashort TE and short TR, wherein the spatiospectrally encoded FIDs are acquired without water suppression and without lipid suppression;
      acquiring, based upon the MR signals, embedded navigator data for tracking system instability and for tracking motion of the object, wherein the navigator data are acquired simultaneously with the spatiospectrally encoded FIDs;
      reconstructing spatiospectral functions from the spatiospectrally encoded FIDs using spectral features learned from training data acquired experimentally and generated using quantum mechanical simulations; and
      separating, based upon the MR signals, signals from unsuppressed water molecules, signals from lipid molecules, signals from metabolites, and signals from macromolecules;
      wherein one or more quantitative tissue susceptibility maps, one or more tissue relaxation constant maps, one or more metabolite maps, and one or more macromolecule maps can be obtained from a single MRSI data set that is based upon the MR signals.

2. The device of claim 1, wherein the training data are acquired to learn the spectral features of different molecules in the object, wherein the spectral features that are learned are used to construct subspace representations of individual molecules and wherein the spectral features that are learned are used for general MRSI experiments.

3. The device of claim 2, wherein the training data are acquired using: one or more single voxel spectroscopy scans; one or more ultrashort-TE, 2D or 3D chemical shift imaging sequences; or one or more ultrashort-TE, low-resolution, 2D or 3D echo-planar spectroscopic imaging sequences.

4. The device of claim 1, wherein a FID-based, ultrashort-TE, very-short-TR acquisition is used to generate the spatiospectrally encoded FIDs, wherein the ultrashort-TE is less than 4 ms, wherein the very-short-TR is less than 300 ms, wherein power of the RF transceiver is optimized for a signal-to-noise-ratio (SNR) of a metabolite spatiospectral function, and wherein neither water nor lipid suppression is used.

5. The device of claim 4, wherein the spatiospectral encoding strategy uses different gradient waveforms to generate (k,t)-space sampling trajectories, wherein the (k,t)-space sampling trajectories comprise one or more Cartesian trajectories, one or more echo-planar trajectories, or one or more other non-Cartesian trajectories, and wherein the non-Cartesian trajectories comprises a spiral trajectory, a radial trajectory, or a concentric ring trajectory.

6. The device of claim 4, wherein the spatiospectral encoding strategy uses a corresponding (k,t)-space, with k denoting three spatial frequency dimensions and t denoting an additional temporal dimension, that is sampled sparsely in variable density, wherein a center k-space region is sampled with Nyquist density and the rest of the k-space is sampled below Nyquist density, and wherein the temporal dimension is sampled at or below Nyquist density.

7. The device of claim 4, wherein the acquisition uses a spatiospectral encoding strategy in which acquisition of additional navigator signals with circular trajectories or linear trajectories is interleaved into a total acquisition period.

8. The device of claim 1, wherein the learned spectral features of NMR-detectable molecules are used for processing acquired (k, t)-space data to obtain desired spatiospectral distributions.

9. The device of claim 1, wherein a union-of-subspaces model is used to represent and separate the spatiospectral distributions originating from different types of molecules in the object, including the water molecules, the lipid molecules, the metabolites, and the macromolecules.

10. The device of claim 9, wherein for $^1$H-MRSI, the union-of-subspaces model is expressed as:

$$\rho(r, t) = \sum_{l_w=1}^{L_w} c_{l_w}(r)\phi_{l_w}(t) + \sum_{l_f=1}^{L_f} c_{l_f}(r)\phi_{l_f}(t) + \sum_{l_m=1}^{L_m} c_{l_m}(r)\phi_{l_m}(t) + \sum_{l_b=1}^{L_b} c_{l_b}(r)\phi_{l_b}(t),$$

where r denotes the spatial dimensions, the partially separable functions on the right hand side of the equation represent the water component, lipid component, metabolite component and macromolecule baseline component, respectively, and $L_x$ is the model order for an individual component, wherein x denotes w, f, m, or b.

11. The device of claim 10, wherein basis functions $\{\phi_{l_x}(t)\}$, are determined for individual signal components based on the spectral features learned from the training data acquired experimentally and generated using quantum mechanical simulations.

12. The device of claim 4, wherein the acquisition uses a spatiospectral encoding strategy in which unsuppressed/companion water spectroscopic signals are used to determine $B_0$ field inhomogeneity and coil receiver sensitivity profiles, to estimate and correct $B_0$ field drifts, and to track and correct for head motion during a scan, without a need for acquiring additional auxiliary data for the same purposes.

13. The device of claim 12, wherein the quantitative tissue susceptibility maps are extracted from $B_0$ field maps estimated from the unsuppressed water spectroscopic signals.

14. The device of claim 12, wherein quantitative $T_2^*$ maps are obtained from the unsuppressed water spectroscopic signals.

15. The device of claim 12, where $B_0$ field maps and $T_2^*$ maps are determined using all the temporal samples, or echoes, available.

16. The device of claim 4, wherein the acquisition uses a spatiospectral encoding strategy in which unsuppressed water and lipid signals are removed from sparsely sampled data using a union-of-subspaces model that is expressed as:

$$\rho(r, t) = \sum_{l_w=1}^{L_w} c_{l_w}(r)\phi_{l_w}(t) + \sum_{l_f=1}^{L_f} c_{l_f}(r)\phi_{l_f}(t) + \sum_{l_m=1}^{L_m} c_{l_m}(r)\phi_{l_m}(t) + \sum_{l_b=1}^{L_b} c_{l_b}(r)\phi_{l_b}(t),$$

where r denotes the spatial dimensions, the partially separable functions on the right hand side of the equation represent the water component, lipid component, metabolite component and macromolecule baseline component, respectively, and $L_x$ is the model order for an individual component, wherein x denotes w, f, m, or b, and wherein metabolite and macromolecule spatiospectral distributions are reconstructed and separated from water/lipid-removed MRSI data.

17. The device of claim 16, wherein metabolite and macromolecule reconstructions are determined by solving the following optimization problem $$\hat{C}_m, \hat{C}_b = \arg \min_{C_m, C_b} \|d - \Omega\{FB \odot (C_m\Psi_m + C_b\Psi_b)\}\|_2^2 + \lambda_m R_m(C_m, \Psi_m) + \lambda_b R_b(C_b, \Psi_b),$$

where d is a vector containing all the data with water and lipid signals removed, 12 denotes a (k,t)-space sampling operator, F denotes a Fourier transform operator, B models the $B_0$ inhomogeneity effects including spatially dependent frequency shifts and experiment-dependent spectral distortions, $\psi_m$ and $\psi_b$ are matrix representations of the metabolite basis and macromolecule basis, respectively, $C_m$ and $C_b$ are matrix representations of $\{c_{l_m}(r)\}$ and $\{c_{l_b}(r)\}$, respectively, the $\|\cdot\|_2^2$ term measures data consistency, $R_m(\cdot)$ and $R_b(\cdot)$ impose spatial regularization on the desired spatiospectral reconstruction, and $\lambda_m$ and $\lambda_b$ are the regularization parameters.

18. The device of claim 17, where $R_m(\cdot)$ and $R_b(\cdot)$ are quadratic regularization that enforces edge-preserving smoothness or non-quadratic regularization that enforces sparsity constraints on spatiospectral variations of individual signal components.

19. A method of acquiring spatiospectral distributions from an object, the method comprising:

generating a static magnetic field, the object being positioned in the static magnetic field;
controlling an RF transceiver to transmit RF signals to an RF coil assembly including a plurality of gradient coils;
controlling the RF transceiver to receive imaging data;
acquiring, based upon the imaging data, spatiospectrally encoded free induction decays (FIDs) that sparsely sample a (k,t)-space with ultrashort TE and short TR;
acquiring, based upon the imaging data, embedded navigator data for tracking system instability and for tracking motion of the object, wherein the navigator data are acquired simultaneously with the spatiospectrally encoded FIDs;
reconstructing spatiospectral functions from the spatiospectrally encoded FIDs using spectral features learned from training data acquired experimentally and generated using quantum mechanical simulations;
separating, based upon the imaging data, spatiospectral distributions of water, lipids, metabolites and macromolecules; and
generating one or more quantitative tissue susceptibility maps, one or more $T_2^*$ maps, one or more $B_0$ inhomogeneity maps, and one or more maps of various metabolites and macromolecules from a single MRSI data set that is based upon the imaging data;
wherein the ultrashort TE is less than 4 ms and the short TR is less than 300 ms, and wherein the method does not require a water suppression pulse or a lipid suppression pulse for $^1$H-MRSI.

20. A non-transitory computer-readable storage device comprising executable instructions which, responsive to being executed by a processor, cause the processor to perform operations, the operations comprising:
acquiring spatiospectrally encoded FID data covering (k, t)-space in variable density and variable SNR with ultrashort-TE and short-TR, without water and lipid suppression, suitable for image reconstruction using a union-of-subspaces model or a linear combination of low-rank matrix/tensor models; and
reconstructing a spatiospectral function from the spatiospectrally encoded FID data that is sparsely sampled using the union-of-subspaces model or the linear combination of low-rank matrix/tensor models;
wherein the acquiring of the spatiospectrally encoded FID data is performed utilizing an RF coil assembly including a plurality of gradient coils, and an RF transceiver controlled by a pulse module to transmit RF signals to the RF coil assembly, and
wherein an ultrashort TE less than 4 ms and a short TR less than 300 ms are utilized and no water suppression pulse is used and no lipid suppression pulse is used.

* * * * *